US008719045B2

(12) United States Patent
Yoon et al.

(10) Patent No.: US 8,719,045 B2
(45) Date of Patent: May 6, 2014

(54) PERSONAL ASSESSMENT INCLUDING FAMILIAL RISK ANALYSIS FOR PERSONALIZED DISEASE PREVENTION PLAN

(75) Inventors: Paula W. Yoon, Norcross, GA (US); Maren T. Scheuner, Manhattan Beach, CA (US); Cynthia Jorgensen, Atlanta, GA (US); Muin J. Khoury, Atlanta, GA (US)

(73) Assignee: The United States of America as represented by the Secretary of the Department of Health and Human Services, Centers for Disease Control and Prevention, Washington, DC (US), part interest ( * ) Notice: Subject to any disclaimer, the term of this patent is extended or adjusted under 35 U.S.C. 154(b) by 1155 days.

(21) Appl. No.: 11/815,445

(22) PCT Filed: Feb. 2, 2006

(86) PCT No.: PCT/US2006/003968
§ 371 (c)(1),
(2), (4) Date: May 20, 2008

(87) PCT Pub. No.: WO2006/084195
PCT Pub. Date: Aug. 10, 2006

(65) Prior Publication Data
US 2009/0018863 A1 Jan. 15, 2009

Related U.S. Application Data

(60) Provisional application No. 60/650,076, filed on Feb. 3, 2005.

(51) Int. Cl.
*G06Q 10/00* (2012.01)
*G06Q 50/00* (2012.01)

(52) U.S. Cl.
USPC ............................................................ 705/2

(58) Field of Classification Search
USPC .................................................... 705/2, 3
See application file for complete search history.

(56) References Cited

U.S. PATENT DOCUMENTS 5,692,501 A 12/1997 Minturn
6,322,504 B1 11/2001 Kirshner
(Continued)

FOREIGN PATENT DOCUMENTS

WO  WO 2006/084195 A3  8/2006

OTHER PUBLICATIONS

Chronic Disease Genomics Standing Committee Minutes, Utah Department of Health, Aug. 5, 2004, 2 pages.

(Continued)

*Primary Examiner* — John Pauls
*Assistant Examiner* — Trang Nguyen
(74) *Attorney, Agent, or Firm* — Klarquist Sparkman, LLP

(57) ABSTRACT

Family health history information can be used to assess familial risk for common diseases and determine early detection and prevention medical strategies. Assessed familial risk of disease can then be used to determine recommendations for disease prevention and screening that are targeted to familial risk. Other factors can be included to generate personalized disease prevention recommendations. For example, personal health history information, personal health behavior information, or both can be collected and assessed to generate personalized disease prevention recommendations based on the information collected. Recommendations for disease prevention and screening based at least on familial risk can be used to provide a personalized disease prevention plan that encourages a person to make behavior changes that will reduce the risk of disease and utilize preventive health services.

48 Claims, 59 Drawing Sheets

(56) References Cited

U.S. PATENT DOCUMENTS

| | | | |
|---|---|---|---|
| 6,602,469 | B1 | 8/2003 | Maus et al. |
| 7,951,078 | B2 | 5/2011 | Scheuner |
| 8,357,089 | B2 | 1/2013 | Scheuner |
| 2002/0184055 | A1 | 12/2002 | Naghavi et al. |
| 2003/0040002 | A1* | 2/2003 | Ledley ............................... 435/6 |
| 2003/0120515 | A1 | 6/2003 | Geller |
| 2003/0187688 | A1 | 10/2003 | Fey et al. |
| 2003/0190602 | A1* | 10/2003 | Pressman et al. ................. 435/5 |
| 2003/0204418 | A1 | 10/2003 | Ledley |
| 2003/0208108 | A1 | 11/2003 | Shewmake et al. |
| 2004/0153249 | A1* | 8/2004 | Zhang et al. ..................... 702/19 |
| 2005/0246207 | A1* | 11/2005 | Noonan et al. .................... 705/4 |
| 2005/0255458 | A1* | 11/2005 | Polansky .......................... 435/5 |
| 2006/0073097 | A1* | 4/2006 | Ma et al. ......................... 424/9.1 |
| 2006/0173717 | A1* | 8/2006 | Scheuner ......................... 705/2 |
| 2011/0201903 | A1 | 8/2011 | Scheuner |

OTHER PUBLICATIONS

"Family History," Centers for Disease Control and Prevention, Office of Genomics and Disease Prevention web site, www.cdc.gov/genomics/fHix.htm, Dec. 2007, listing events from 2002 onward, 4 pages.

"Family History for Preventive Medicine and Public Health," Centers for Disease Control and Prevention, Office of Genomics and Disease Prevention, Sep. 2004, 2 pages.

"Family History for Preventive Medicine and Public Health," Poster—Genomics Day Symposium, May 5, 2003, Atlanta, GA, 1 page.

Family History Public Health Initiative, National Office of Public Health Genomics, http://www.cdc.gov/genomics/famhistory/famhist.htm, archived Jun. 29, 2006, recounting events from 2002, 4 pages.

Grundy et al., "Definition of Metabolic Syndrome, Report of the National Heart, Lung, and Blood Institute/American Heart Association Conference on Scientific Issues Related to Definition," *Circulation Journal of the American Heart Association*, vol. 109, Jan. 2004, 7 pages.

"Genomics and Population Health: United States 2003," http://www.cdc.gov/genomics/activities/ogdp/2003.htm, Centers for Disease Control and Prevention, Office of Genomics and Disease Prevention, Atlanta, GA, Mar. 2004, 121 pages.

Hunt et al., "Family History Assessment: Strategies for Prevention of Cardiovascular Disease," *American Journal of Preventive Medicine*, vol. 24, No. 2, 2003, pp. 136-142, 7 pages.

International Search Report, Dec. 19, 2006, 2 pages.

"*James*Link: Personalized Cancer Risk Assessment. Discover your Family's Connection to Cancer Risk," http://www.jamesline.com/patientsandvisitors/prevention/cancergenetics/, The Ohio State University Medical Center, 2005, 61 pages.

McCusker et al., "Family History of Heart Disease and Cardiovascular Disease Risk-Reducing Behaviors," *Genetics in Medicine*, vol. 6, No. 3, May/Jun. 2004, pp. 153-158, 6 pages.

"Proposed Data Collections Submitted for Public Comment and Recommendations," Department of Health and Human Services, Centers for Disease Control and Prevention, *Federal Register*, vol. 69, No. 22, Feb. 3, 2004, 2 pages.

Scheuner, "Clinical application of genetic risk assessment strategies for coronary artery disease: genotypes, phenotypes and family history," *Primary Care; Clinics in Office Practice*, vol. 31, No. 3, Sep. 2004, 21 pages.

Scheuner et al., "Collection of Family History in Epidemiologic Studies of Coronary Artery Disease: Can We Do Better?" Poster presentation at the Annual Clinical Genetics Meeting, Mar. 4-7, 2004, Kissimmee FL, 11 pages.

Scheuner et al., "Contribution of mendelian disorders to common chronic disease: opportunities for recognition, intervention and prevention," *American Journal of Medical Genetics*, vol. 125C, pp. 50-65, Feb. 15, 2004, 16 pages.

Scheuner et al., "Family History: A Comprehensive Genetic Risk Assessment Method for the Chronic Conditions of Adulthood," *American Journal of Medical Genetics*, vol. 71, pp-315-324, 1997, 10 pages.

Scheuner, "Family History: A tool for Medical Genetics and Public Health," American College of Medical Genetics Annual Meeting, Mar. 7, 2004, Orlando, FL, 39 pages.

Scheuner, "Family History as a Tool for Evaluating Cancer Genetic Risk," American Institute for Cancer Research, International Research Conference on Food, Nutrition and Cancer, Washington, DC, Jul. 17, 2003, 28 pages.

Scheuner, "Genetic Evaluation for Coronary Artery Disease," *Genetics in Medicine*, vol. 5, No. 4, Jul./Aug. 2003, pp. 269-285, 17 pages.

Scheuner et al., "Genetic Risk Assessment for Common Disease," Emery and Rimoin's Principles and Practice of Medical Genetics, $4^{th}$ edition, Rimoin DL, Connor JM, Pyeritz, RE, eds., New York: Churchill Livingstone, 2002, pp. 654-674, 21 pages.

Sweet et al., "Identification and Referral of Families at High Risk for Cancer Susceptibility," *Journal of Clinical Oncology*, vol. 20, No. 2, Jan. 15, 2002, pp. 528-537.

Tyagi et al., "Using Decision Analytic Methods to Assess the Utility of Family History Tools," *American Journal of Preventive Medicine*, Vo. 24, No. 2, Feb. 2003, pp. 199-207, 9 pages.

Yoon et al., "Can Family History Be Used as a Tool for Public Health and Preventive Medicine?" *Genetics in Medicine*, vol. 4, No. 4, 2002, 13 pages.

Yoon, "Developing and Evaluating Family History Tools for Public Health and Preventive Medicine," American College of Medical Genetics Annual Meeting, Mar. 6, 2004, Orlando, FL, 34 pages.

Yoon, "Family History for Preventive Medicine—A Bridge from Genetics to Genomics," Marshfield Clinic, May 7, 2004, Wisconsin Dells, WI, 60 pages.

Yoon, "Family History for Public Health and Preventive Medicine," The $17^{th}$ National Conference on Chronic Disease Prevention and Control, Feb. 19-21, 2003, St. Louis, MO, 58 pages.

Yoon, "Family History for Public Health and Preventive Medicine," Family History Work Group, Centers for Disease Control and Prevention, Office of Genomics and Disease Prevention, 2003, 24 pages.

Yoon, "From Gene Discovery to Treatment and Prevention of Disease: Public Health Perspective," Science, Law and Policy, Louisiana State University, Baton Rouge, LA, Feb. 5, 2004, 41 pages.

Yoon, "Genomics and the Public's Health: Translating New Science into Population Health Benefits," Centers for Disease Control and Prevention, Office of Genomics and Disease Prevention, Montreal, Canada, Dec. 4, 2003, 40 pages.

Yoon et al., "Research Priorities for Evaluating Family History in the Prevention of Common Chronic Diseases," *American J Prev Medicine*, vol. 24, No. 2, pp. 128-135, 2003, 8 pages.

Your Disease Risk, Cancer—Bladder, Harvard School of Public Health, Feb. 1, 2006, 15 pages. http://www.yourdiseaserisk.harvard.edu/english/.

Your Disease Risk, Cancer—Breast, Harvard School of Public Health, Feb. 1, 2006, 19 pages. http://www.yourdiseaserisk.hardard.edu/english/.

Your Disease Risk, Cancer—Cervical, Harvard School of Public Health, Feb. 1, 2006, 15 pages. http://www.yourdiseaserisk.harvard.edu/english/.

Your Disease Risk, Cancer—Colon, Harvard School of Public Health, Feb. 1, 2006, 18 pages. http://www.yourdiseaserisk.harvard.edu/english/index.htm.

Your Disease Risk, Cancer—Kidney, Harvard School of Public Health, Feb. 1, 2006, 14 pages. http://www.yourdiseaserisk.harvard.edu/english/.

Your Disease Risk, Cancer—Lung, Harvard School of Public Health, Feb. 1, 2006, 19 pages. http://www.yourdiseaserisk.harvard.edu/english/.

Your Disease Risk, Cancer—Melanoma, Harvard School of Public Health, Feb. 1, 2006, 15 pages. http://www.yourdiseaserisk.harvard.edu/english/.

(56) References Cited

OTHER PUBLICATIONS

Your Disease Risk, Cancer—Ovarian, Harvard School of Public Health, Feb. 1, 2006, 15 pages. http://www.yourdiseaserisk.harvard.edu/english/.

Your Disease Risk, Cancer—Pancreatic, Harvard School of Public Health, Feb. 1, 2006, 15 pages. http://www.yourdiseaserisk.harvard.edu/english/.

Your Disease Risk, Cancer—Prostate, Harvard School of Public Health, Feb. 1, 2006, 15 pages. http://www.yourdiseaserisk.harvard.edu/english/.

Your Disease Risk, Cancer—Stomach, Harvard School of Public Health, Feb. 1, 2006, 14 pages. http://www.yourdiseaserisk.harvard.edu/english/.

Your Disease Risk, Cancer—Uterine, Harvard School of Public Health, Feb. 1, 2006, 16 pages. http://www.yourdiseaserisk.harvard.edu/english/.

Your Disease Risk, Diabetes, Harvard School of Public Health, Feb. 1, 2006, 19 pages. http://www.yourdiseaserisk.harvard.edu/english/.

Your Disease Risk, Heart Disease, Harvard School of Public Health, Feb. 1, 2006, 23 pages. http://www.yourdiseaserisk.harvard.edu/english/.

Your Disease Risk, Osteoporosis, Harvard School of Public Health, Feb. 1, 2006, 21 pages. http://www.yourdiseaserisk.harvard.edu/english/.

Your Disease Risk, Stroke, Harvard School of Public Health, Feb. 1, 2006, 22 pages. http://www.yourdiseaserisk.harvard.edu/english/.

* cited by examiner

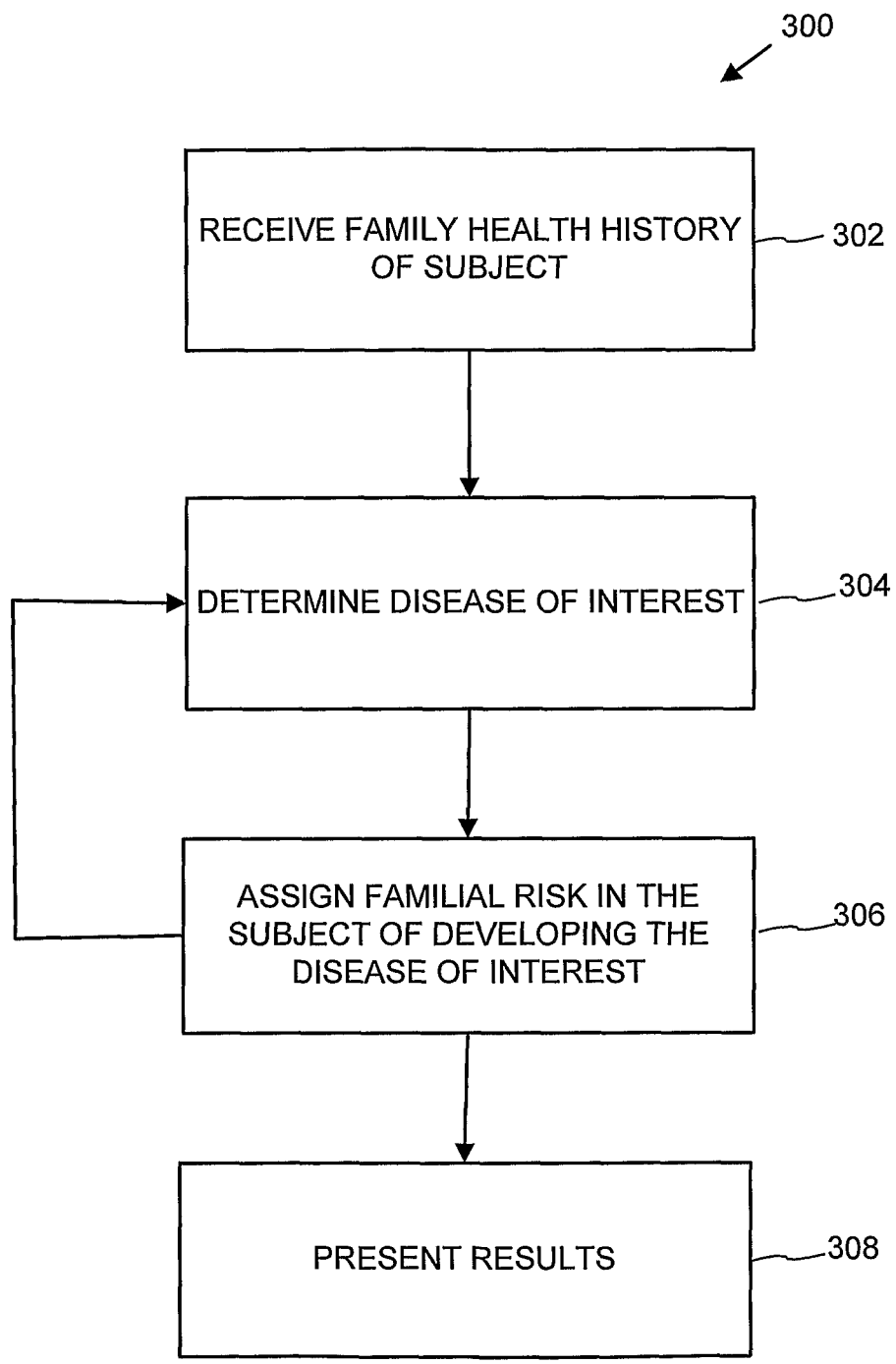

FIG. 9

| | One 1st deg rel w/ early breast ca and ovarian | One 1st deg rel w/ late breast ca and ovarian | One 1st FEMALE rel w/ early breast ca | One 1st deg MALE rel w/ early breast ca | One 1st deg rel w/ ovarian | One 1st deg MALE rel w/ late breast | TWO 1st deg FEMALE rel w/ late breast | One 1st deg FEMALE rel w/ late breast | No 1st deg rel w/ breast |
|---|---|---|---|---|---|---|---|---|---|
| One 1st deg rel w/ early breast and ovarian | 6-1 $H^{a,c,e,f}$ | 6-2 $H^{a,c,e,f}$ | 6-3 $H^{a,e,f}$ | 6-4 $H^{a,d,e,f}$ | 6-5 $H^{a,c,e}$ | 6-6 $H^{a,d,e,f}$ | 6-7 $H^{a,e,i}$ | 6-8 $H^{a,e,f}$ | 6-9 $H^{a,e}$ |
| One 1st deg rel w/ late breast and ovarian | | 6-10 $H^{a,c,f}$ | 6-11 $H^{a,e,f}$ | 6-12 $H^{a,d,e,f}$ | 6-13 $H^{a,c}$ | 6-14 $H^{a,d,f}$ | 6-15 $H^{a,i}$ | 6-16 $H^{a,f}$ | 6-17 $H^{a}$ |
| One 1st deg FEMALE rel w/ early breast ca | | | 6-18 $H^{e,f}$ | 6-19 $H^{d,e,f}$ | 6-20 $H^{b,e}$ | 6-21 $H^{d,e,f}$ | 6-22 $H^{e,i}$ | 6-23 $H^{e,f}$ | 6-24 $H^{e}$ |
| One 1st deg MALE rel w/ early breast ca | | | | 6-25 $H^{d,e,f}$ | 6-26 $H^{b,d,e}$ | 6-27 $H^{d,e,f}$ | 6-28 $H^{d,e,i}$ | 6-29 $H^{d,e,f}$ | 6-30 $H^{d,e}$ |
| One 1st deg rel w/ ovarian | | | | | 6-31 $H^{c}$ | 6-32 $H^{b,d}$ | 6-33 $H^{b,f}$ | 6-34 $M^{b}$ $H^{b}$ if AJ | 6-35 $A$ $H^{h}$ if AJ |
| One 1st deg MALE rel w/ late breast ca | | | | | | 6-36 $H^{d,f}$ | 6-37 $H^{d,i}$ | 6-38 $H^{d,f}$ | 6-39 $M^{d}$ $H^{d}$ if AJ |
| Two 1st deg FEMALE rel w/ late breast ca | | | | | | | 6-40 $H^{i}$ | 6-41 $H^{i}$ | 6-42 $H^{f}$ |
| One 1st deg FEMALE rel w/ late breast ca | | | | | | | | 6-43 $H^{f}$ | 6-44 $M^{g}$ |
| No 1st deg rel with breast | | | | | | | | | 6-45 $A$ |

| | One 2nd deg rel w/ early breast ca and ovarian | One 2nd deg rel w/ late breast ca and ovarian | One 2nd deg FEMALE rel w/ early breast ca | One 2nd deg MALE rel w/ early breast ca | One 2nd deg rel w/ ovarian | One 2nd deg MALE rel w/ late breast ca | TWO 2nd deg FEMALE rel w/ late breast | One 2nd deg FEMALE rel w/ late breast | No 2nd deg rel w/ breast ca |
|---|---|---|---|---|---|---|---|---|---|
| One 1st deg rel w/ early breast ca and ovarian | 6-46 $H^{a,c,e,f}$ | 6-47 $H^{a,c,e,f}$ | 6-48 $H^{a,e,f}$ | 6-49 $H^{a,d,e,f}$ | 6-50 $H^{a,c,e}$ | 6-51 $H^{a,d,e,f}$ | 6-52 $H^{a,e,i}$ | 6-53 $H^{a,e,f}$ | $H^{a,e}$ |
| One 1st deg rel w/ late breast ca and ovarian | 6-54 $H^{a,c,e,f}$ | 6-55 $H^{a,c,f}$ | 6-56 $H^{a,e,f}$ | 6-57 $H^{a,d,e,f}$ | 6-58 $H^{a,c}$ | 6-59 $H^{a,d,f}$ | 6-60 $H^{a,i}$ | 6-61 $H^{a,f}$ | $H^{a}$ |
| One 1st deg FEMALE rel w/ early breast ca | 6-62 $H^{a,e,f}$ | 6-63 $H^{a,e,f}$ | 6-64 $H^{e,f}$ | 6-65 $H^{d,e,f}$ | 6-66 $H^{b,e}$ | 6-67 $H^{d,e,f}$ | 6-68 $H^{e,i}$ | 6-69 $H^{e,f}$ | $H^{e}$ |
| One 1st deg MALE rel w/ early breast ca | 6-70 $H^{a,d,e,f}$ | 6-71 $H^{a,d,e,f}$ | 6-72 $H^{d,e,f}$ | 6-73 $H^{d,e,f}$ | 6-74 $H^{b,d,e}$ | 6-75 $H^{d,e,f}$ | 6-76 $H^{d,e,i}$ | 6-77 $H^{d,e,f}$ | $H^{d,e}$ |
| One 1st deg rel w/ ovarian | 6-78 $H^{a,c,e}$ | 6-79 $H^{a,c}$ | 6-80 $H^{b,e}$ | 6-81 $H^{b,d,e}$ | 6-82 $H^{c}$ | 6-83 $H^{b,d}$ | 6-84 $H^{b,f}$ | 6-85 $M^{b}$ $H^{b}$ if AJ[j] | A $H^{b}$ if AJ[j] |
| One 1st deg MALE rel w/ late breast ca | 6-86 $H^{a,d,e,f}$ | 6-87 $H^{a,d,f}$ | 6-88 $H^{d,e,f}$ | 6-89 $H^{d,e,f}$ | 6-90 $H^{b,d}$ | 6-91 $H^{d,f}$ | 6-92 $H^{d,i}$ | 6-93 $H^{d,f}$ | $M^{d,g}$ |
| TWO 1st deg FEMALE rel w/ late breast ca | 6-94 $H^{a,e,i}$ | 6-95 $H^{a,i}$ | 6-96 $H^{e,i}$ | 6-97 $H^{d,e,i}$ | 6-98 $H^{b,f}$ | 6-99 $H^{d,i}$ | 6-100 $H^{i}$ | 6-101 $H^{i}$ | $H^{f}$ |
| One 1st deg FEMALE rel w/ late breast ca | 6-102 $H^{a,e,f}$ | 6-103 $H^{a,f}$ | 6-104 $M^{e,f}$ $H^{e,f}$ if pat $H^{e,f}$ if AJ[j] | 6-105 $H^{d,e,f}$ | 6-106 $M^{b}$ $H^{b}$ if AJ[j] | 6-107 $H^{d,f}$ | 6-108 $H^{i}$ | 6-109 $M^{f}$ | $M^{y}$ |
| No 1st deg rel with breast | $H^{a,e}$ | $H^{a}$ | A $M^{e}$ if pat | A $M^{d,e}$ if pat | A | A | $M^{f}$ | A | A |

FIG. 11

| | One 2nd deg rel w/ early breast ca and ovarian | One 2nd deg rel w/ late breast ca and ovarian | One 2nd deg FEMALE rel w/ early breast ca | One 2nd deg MALE rel w/ early breast ca | One 2nd deg rel w/ ovarian | One 2nd deg MALE rel w/ late breast ca | TWO 2nd deg FEMALE rel w/ late breast | One 2nd deg FEMALE rel w/ late breast | No 2nd deg rel w/ breast ca |
|---|---|---|---|---|---|---|---|---|---|
| One 2nd deg rel w/ early breast ca and ovarian | | 6-111 $H^{a,c,f}$ | 6-112 $H^{a,e,f}$ | 6-113 $H^{a,d,e,f}$ | 6-114 $H^{a,c,e}$ | 6-115 $H^{a,d,e,f}$ | 6-116 $H^{a,e,i}$ | 6-117 $H^{a,e,f}$ | 6-118 $H^{a,e}$ |
| One 2nd deg rel w/ late breast ca and ovarian | $H^{a,c,e,f}$ | 6-119 $H^{a,c,f}$ | 6-120 $H^{a,e,f}$ | 6-121 $H^{a,d,e,f}$ | 6-122 $H^{a,c}$ | 6-123 $H^{a,d,f}$ | 6-124 $H^{a,i}$ | 6-125 $H^{a,f}$ | 6-126 $H^{a}$ |
| One 2nd deg FEMALE rel w/ early breast ca | $H^{a,e,f}$ | $H^{a,e,f}$ | 6-127 $H^{e,f}$ | 6-128 $H^{d,e,f}$ | 6-129 $H^{b,e}$ | 6-130 $H^{d,e,f}$ | 6-131 $H^{e,i}$ | 6-132 $H^{e,f}$ | 6-133 $A$ |
| One 2nd deg MALE rel w/ early breast ca | $H^{a,d,e,f}$ | $H^{a,d,e,f}$ | $H^{d,e,f}$ | 6-134 $H^{d,e,f}$ | 6-135 $H^{b,d,e}$ | 6-136 $H^{d,e,f}$ | 6-137 $H^{d,e,i}$ | 6-138 $H^{d,e,f}$ | 6-139 $A$ $M^{d,e}$ if pat $M^{d,e}$ if AJ$^j$ |
| One 2nd deg rel w/ ovarian | $H^{a,c,e}$ | $H^{a,c}$ | $H^{b,e}$ | $H^{b,d,e}$ | | 6-140 $H^{c}$ | $H^{b,i}$ | 6-143 $H^{b}$ | 6-144 $A$ $M^{h}$ if AJ$^j$ |
| One 2nd deg MALE rel w/ late breast ca | $H^{a,d,e,f}$ | $H^{a,d,f}$ | $H^{d,e,f}$ | $H^{d,e,f}$ | $H^{b,d}$ | 6-141 $H^{b,d}$ | 6-142 $H^{b,f}$ | | |
| TWO 2nd deg FEMALE rel w/ late breast ca | $H^{a,e,f}$ | $H^{a,f}$ | $H^{e,f}$ | $H^{d,e,f}$ | $H^{b,f}$ | 6-145 $H^{d,f}$ | 6-146 $H^{d,i}$ | 6-147 $H^{d,f}$ | 6-148 $A$ $M^{d}$ if AJ$^j$ |
| One 2nd deg FEMALE rel w/ late breast ca | $H^{a,e,f}$ | $H^{a,f}$ | $M^{e,f}$ $H^{e,f}$ if pat | $M^{d,e,f}$ $H^{d,e,f}$ if pat | $M^{b}$ | $M^{d,f}$ | $M^{f}$ | 6-152 $M^{f}$ | 6-153 $A$ |
| No 2nd deg rel with breast | $H^{a,e}$ | $H^{a}$ | $A$ $M^{e}$ if pat | $A$ $M^{d,e}$ if pat | $A$ | $A$ | $M^{f}$ | $A$ | 6-154 $A$ |

| | One 1st deg ovarian, early breast, early colon | One 1st deg ovarian, early breast, late colon | One 1st deg ovarian, late breast, early colon | One 1st deg ovarian, late breast, late colon | One 1st deg ovarian + early breast | One 1st deg ovarian + late breast | One 1st deg ovarian + early colon | One 1st deg ovarian + late colon | One 1st deg ovarian | One 1st deg male breast | One 1st deg female early breast | Two 1st deg female late breast | One 1st deg female late breast | One 1st deg early colon | One 1st deg late colon | No 1st deg w/ cancer |
|---|---|---|---|---|---|---|---|---|---|---|---|---|---|---|---|---|
| One 1st deg ovarian | | | | | | | | | 14-101 H g | | | | | | | |
| One 1st deg male breast | | | | | | | | | 14-102 H le | 14-109 H jl | | | | | | |
| One 1st deg female early breast | | | | | | | | | 14-103 H ie | 14-110 H ij | 14-116 H ij | | | | | |
| Two 1st deg female late breast | | | | | | | | | 14-104 H je | 14-111 H kl | 14-117 M ik | 14-122 M k | | | | |
| One 1st deg female late breast | | | | | | | | | 14-105 M Hif AJ e | 14-112 M jl | 14-118 A Mif AJ ij | 14-123 M k | 14-127 A | | | |
| One 1st deg early colon | | | | | | | | | 14-106 H fm | 14-113 A Mif AJ - | 14-119 A Mif AJ - | 14-124 A | 14-128 A | 14-131 H mn | | |
| One 1st deg late colon | | | | | | | | | 14-107 M Hif AJ fh | 14-114 A Mif AJ - | 14-120 A Mif AJ - | 14-125 A | 14-129 A | 14-132 A | 14-134 A | |
| No 1st deg w/ cancer | | | | | | | | | 14-108 M Hif AJ h | 14-115 A Mif AJ - | 14-121 A Mif AJ - | 14-126 A | 14-130 A | 14-133 A | 14-135 A | 14-136 A |

| | One 2nd deg ovarian, early breast, early colon | One 2nd deg ovarian, early breast, late colon | One 2nd deg ovarian, late breast, early colon | One 2nd deg ovarian, late breast, late colon | One 2nd deg ovarian + early breast | One 2nd deg ovarian + late breast | One 2nd deg ovarian + early colon | One 2nd deg ovarian + late colon | One 2nd deg ovarian | One 2nd deg male breast | One 2nd deg early female breast | Two 2nd deg female late breast | One 2nd deg female late breast | One 2nd deg early colon | One 2nd deg late colon | No 2nd deg w/ cancer |
|---|---|---|---|---|---|---|---|---|---|---|---|---|---|---|---|---|
| One 1st deg ovarian, early breast, early colon | 14-137 H agij mn | 14-138 H agij mn | 14-139 H agij mn | 14-140 H agijm n | 14-141 H abgij m | 14-142 H abgij m | 14-143 H acgi mn | 14-144 H acgi mn | 14-145 H agi | 14-146 H aijlm | 14-147 H aijm | 14-148 H aikm | 14-149 H aijm | 14-150 H aimn | 14-151 H aim n | |
| One 1st deg ovarian, early breast, late colon | 14-152 H agij mn | 14-153 H agijn mn | 14-154 H agij mn | 14-155 H agijn | 14-156 H abgij | 14-157 H abgij | 14-158 H acgi mn | 14-159 H acgin | 14-160 H agi | 14-161 H aijl | 14-162 H aij | 14-163 H aik | 14-164 H aij | 14-165 H aimn | 14-166 H ain | |
| One 1st deg ovarian, late breast, early colon | 14-167 H agij mn | 14-168 H agij mn | 14-169 H agij mn | 14-170 H agjm n | 14-171 H abgij | 14-172 H abgj m | 14-173 H acgi mn | 14-174 H acgm n | 14-175 H agm | 14-176 H ajlm | 14-177 H aijm | 14-178 H akm | 14-179 H ajm | 14-180 H amn | 14-181 H amn | |
| One 1st deg ovarian, late breast, late colon | 14-182 H agij mn | 14-183 H agijn | 14-184 H agjm n | 14-185 H agjn | 14-186 H abgij | 14-187 H abgj m | 14-188 H acgm n | 14-189 H acgn | 14-190 H ag | 14-191 H ajl | 14-192 H aij | 14-193 H ak | 14-194 H aj | 14-195 H amn | 14-196 H an | |
| One 1st deg ovarian + early breast | 14-197 H abgij m | 14-198 H abgij | 14-199 H abgij | 14-200 H abgij | 14-201 H bgij | 14-202 H bgij | 14-203 H bcgi m | 14-204 H bcgi | 14-205 H bgi | 14-206 H bijl | 14-207 H bij | 14-208 H bik | 14-209 H bij | 14-210 H bfim | 14-211 H bi | |
| One 1st deg ovarian + late breast | 14-212 H abgij | 14-213 H abgij | 14-214 H abgj | 14-215 H abgj | 14-216 H bgij | 14-217 H bgij | 14-218 H bcgi m | 14-219 H bcg | 14-220 H bg | 14-221 H bjl | 14-222 H bij | 14-223 H bk | 14-224 H bj | 14-225 H bfm | 14-226 H b | |
| One 1st deg ovarian + early colon | 14-227 H acgi mn | 14-228 H acgi mn | 14-229 H acgm | 14-230 H acgm n | 14-231 H bcgi | 14-232 H bcgm | 14-233 H cgmn | 14-234 H cgmn | 14-235 H cgm | 14-236 H celm | 14-237 H ceim | 14-238 H cejm | 14-239 H cm | 14-240 H cmn | 14-241 H cmn | |
| One 1st deg ovarian + late colon | 14-242 H acgi mn | 14-243 H acgi n | 14-244 H acgm n | 14-245 H acgn | 14-246 H bcgi | 14-247 H bcg | 14-248 H cgmn | 14-249 H cgn | 14-250 H cg | 14-251 H cel | 14-252 H cel | 14-253 H cej | 14-254 M Hif AJ c | 14-255 H cmn | 14-256 M Hif AJ cn | |

| | One 2nd deg ovarian, early breast, early colon | One 2nd deg ovarian, early breast, late colon | One 2nd deg ovarian, late breast, early colon | One 2nd deg ovarian, late breast, late colon | One 2nd deg ovarian + early breast | One 2nd deg ovarian + late breast | One 2nd deg ovarian + early colon | One 2nd deg ovarian + late colon | One 2nd deg ovarian | One 2nd deg male breast | One 2nd deg early female breast | Two 2nd deg female late breast | One 2nd deg female late breast | One 2nd deg early colon | One 2nd deg late colon | No 2nd deg w/ cancer |
|---|---|---|---|---|---|---|---|---|---|---|---|---|---|---|---|---|
| One 1st deg ovarian | 14-257 H a g i m | 14-258 H a g i | 14-259 H a g m | 14-260 H a g | 14-261 H b g l | 14-262 H b g | 14-263 H c g m | 14-264 H c g | 14-265 H g | 14-266 H e l | 14-267 H e l | 14-268 M HifAJ ej | 14-269 M Hif AJ h | 14-270 M Hif AJ fm | 14-271 M Hif AJ h | |
| One 1st deg male breast | 14-272 H a i j l m | 14-273 H a i j l | 14-274 H a j l m | 14-275 H a j l | 14-276 H b i j l | 14-277 H b j l | 14-278 H c e l m | 14-279 H c e l | 14-280 H e l | 14-281 H j l | 14-282 M Hif pat i j l | 14-283 M k l | 14-284 A Mif AJ j l | 14-285 A Mif AJ – | 14-286 A Mif AJ – | |
| One 1st deg female early breast | 14-287 H a i j m | 14-288 H a l j | 14-289 H a i j m | 14-290 H a l j | 14-291 H b i j | 14-292 H b i j | 14-293 H c e i m | 14-294 H c e i | 14-295 H e i | 14-296 H j l i | 14-297 M Hif pat j i | 14-298 M k l | 14-299 A Mif AJ j l | 14-300 A Mif AJ – | 14-301 A | |
| Two 1st deg female late breast | 14-302 H a i k m | 14-303 H a i k | 14-304 H a k m | 14-305 H a k | 14-306 H b l k | 14-307 H b k | 14-308 H c e j m | 14-309 H c e j | 14-310 H e j | 14-311 H k l | 14-312 M k l | 14-313 M k | 14-314 A | 14-315 A | 14-316 A | |
| One 1st deg female late breast | 14-317 H a i j m | 14-318 H a i j | 14-319 M a j m | 14-320 M a j | 14-321 H b i j | 14-322 M b j | 14-323 M c e m | 14-324 M c e | 14-325 M e | 14-326 A Mif AJ j l | 14-327 A | 14-328 A | 14-329 A | 14-330 A | 14-331 A | |
| One 1st deg early colon | 14-332 H a i m n | 14-333 H a i m n | 14-334 H a m n | 14-335 H a m n | 14-336 H b f i m | 14-337 H b f m | 14-338 H c m n | 14-339 H c m n | 14-340 H f m | 14-341 A | 14-342 A | 14-343 A | 14-344 A | 14-345 M m n | 14-346 A | |
| One 1st deg late colon | 14-347 H a i m n | 14-348 H a i n | 14-349 M HifAJ a m n | 14-350 M HifAJ a n | 14-351 H b f i | 14-352 H b f m | 14-353 M c m n | 14-354 H c m n | 14-355 A MifAJ fh | 14-356 A | 14-357 A | 14-358 A | 14-359 A | 14-360 A | 14-361 A | |
| No 1st deg w/ cancer | | | | | | | | | | | | | | | | |

| | One 2nd deg ovarian, early breast, early colon | One 2nd deg ovarian, early breast, late colon | One 2nd deg ovarian, late breast, early colon | One 2nd deg ovarian, late breast, late colon | One 2nd deg ovarian + early breast | One 2nd deg ovarian + late breast | One 2nd deg ovarian + early colon | One 2nd deg ovarian + late colon | One 2nd deg ovarian | One 2nd deg male breast | One 2nd deg early female breast | Two 2nd deg female late breast | One 2nd deg female late breast | One 2nd deg early colon | One 2nd deg late colon | No 2nd deg w/ cancer |
|---|---|---|---|---|---|---|---|---|---|---|---|---|---|---|---|---|
| One 2nd deg ovarian, early breast, early colon | 14-362 H a g i j m n | 14-363 H a g i j m n | 14-364 H a g i j m n | 14-365 H a g i j m n | 14-366 H a b g i j m | 14-367 H a b g i j m | 14-368 H a c g i m n | 14-369 H a c g i m n | 14-370 H a g i m | 14-371 H a i j l m | 14-372 H a i j m | 14-373 H a i k m | 14-374 H a i j m | 14-375 H a i m n | 14-376 H a i m n | 14-377 H a i m |
| One 2nd deg ovarian, early breast, late colon | | 14-378 H a g i j n | 14-379 H a g i j m n | 14-380 H a g i j m n | 14-381 H a b g i j | 14-382 H a b g i j | 14-383 H a c g i m n | 14-384 H a c g i n | 14-385 H a g i | 14-386 H a i j l | 14-387 H a i j | 14-388 H a i k | 14-389 H a i j | 14-390 H a i m n | 14-391 H a i n | 14-392 H a i n |
| One 2nd deg ovarian, late breast, early colon | | | 14-393 H a g j m n | 14-394 H a g j m n | 14-395 H a b g i j m | 14-396 H a b g j | 14-397 H a c g m n | 14-398 H a c g m | 14-399 H a g m | 14-400 H a j l m | 14-401 H a i j m | 14-402 H a k m | 14-403 H a j m | 14-404 H a m n | 14-405 M Hif pat a m n | 14-406 M Hif pat a m |
| One 2nd deg ovarian, late breast, late colon | | | | 14-407 H a g j n | 14-408 H a b g i j | 14-409 H a b g j | 14-410 H a c g m n | 14-411 H a c g n | 14-412 H a g | 14-413 H a j l | 14-414 H a i j | 14-415 H a k | 14-416 H a j | 14-417 H a m n | 14-418 M Hif pat a n | 14-419 M Hif pat a |
| One 2nd deg ovarian + early breast | | | | | 14-420 H b g i j | 14-421 H b g i j | 14-422 H b c g i m | 14-423 H b c g i | 14-424 H b g i | 14-425 H b i j l | 14-426 H b i j | 14-427 H b i k | 14-428 H b i j | 14-429 H b f i m | 14-430 H b i | 14-431 H b i |
| One 2nd deg ovarian + late breast | | | | | | 14-432 H b g j | 14-433 H b c g m | 14-434 H b c g | 14-435 H b g | 14-436 H b j l | 14-437 H b i j | 14-438 H b k | 14-439 H b j | 14-440 M Hif pat b f m | 14-441 M Hif pat b | 14-442 M Hif pat b |
| One 2nd deg ovarian + early colon | | | | | | | 14-443 H c g m n | 14-444 H c g m n | 14-445 H c g m | 14-446 H c e l m | 14-447 H c e j m | 14-448 H c e j m | 14-449 M c e m | 14-450 H c m n | 14-451 M c m n | 14-452 M c m |

FIG. 17

| | One 2nd deg ovarian, early breast, early colon | One 2nd deg ovarian, early breast, late colon | One 2nd deg ovarian, late breast, early colon | One 2nd deg ovarian, late breast, late colon | One 2nd deg ovarian + early breast | One 2nd deg ovarian + late breast | One 2nd deg ovarian + early colon | One 2nd deg ovarian + late colon | One 2nd deg ovarian | One 2nd deg male breast | One 2nd deg early female breast | Two 2nd deg female late breast | One 2nd deg female late breast | One 2nd deg early colon | One 2nd deg late colon | No 2nd deg w/ cancer |
|---|---|---|---|---|---|---|---|---|---|---|---|---|---|---|---|---|
| One 2nd deg ovarian + late colon | | | | | | | | 14-453 H c g n | 14-454 H c g | 14-455 H c e l | 14-456 H c e i | 14-457 H c e j | 14-458 M c e | 14-459 M c m n | 14-460 M c n | 14-461 A M if AJ h |
| One 2nd deg ovarian | | | | | | | | | 14-462 H g | 14-463 H e l | 14-464 H e i | 14-465 H e j | 14-466 M e | 14-467 M f m | 14-468 A M if AJ h | 14-469 A M if AJ h |
| One 2nd deg male breast | | | | | | | | | | 14-470 H j l | 14-471 M H if pat i j l | 14-472 M H if pat k l | 14-473 A | 14-474 A | 14-475 A | 14-476 A |
| One 2nd deg early female breast | | | | | | | | | | | 14-477 A M if pat i j | 14-478 A M if pat i k | 14-479 A | 14-480 A | 14-481 A | 14-482 A |
| Two 2nd deg female late breast | | | | | | | | | | | | 14-483 A | 14-484 A | 14-485 A | 14-486 A | 14-487 A |
| One 2nd deg female late breast | | | | | | | | | | | | | 14-488 A | 14-489 A | 14-490 A | 14-491 A |
| One 2nd deg early colon | | | | | | | | | | | | | | 14-492 M m n | 14-493 A | 14-494 A |
| One 2nd deg late colon | | | | | | | | | | | | | | | 14-495 A | 14-496 A |
| No 2nd deg w/ cancer | | | | | | | | | | | | | | | | 14-497 A |

| | One 1st deg rel early colon and ovarian | One 1st deg rel late colon and ovarian | One 1st deg rel early colon | Two 1st deg rel late colon | One 1st deg rel late colon | One 1st deg rel ovarian | No 1st deg rel w/ colon and ovarian |
|---|---|---|---|---|---|---|---|
| One 1st deg rel early colon and ovarian | 6-001 H a c d | | | | | | |
| One 1st deg rel late colon and ovarian | 6-002 H a c d | 6-007 H a c | | | | | |
| One 1st deg rel early colon | 6-003 H a c d | 6-008 H a d | | | | | |
| Two 1st deg rel late colon | 6-004 H a c e | 6-009 H a c d | | | | | |
| One 1st deg rel late colon | 6-005 H a c d | 6-010 H a e | 6-014 H c d | | | | |
| One 1st deg rel ovarian | 6-006 H a c f | 6-011 H a d | 6-015 H c e | 6-019 H e | | | |
| No 1st deg rel w/colon and ovarian | 6-007 H a c | 6-012 H a f | 6-016 H c d | 6-020 H e | 6-023 H d | | |
|  | | 6-013 H a | 6-017 H b c | | 6-024 M b | 6-026 A | |
|  | | 6-018 H c | 6-021 H b d | | | | |
|  | | 6-022 H d | 6-025 M g | | | 6-027 A | |
|  | | | | | | | 6-028 A |

FIG. 19  1900

| | One 2nd deg rel early colon and ovarian | One 2nd deg rel late colon and ovarian | One 2nd deg rel early colon | Two 2nd deg rel late colon | One 2nd deg rel late colon | One 2nd deg rel ovarian | No 2nd deg rel w/ colon and ovarian |
|---|---|---|---|---|---|---|---|
| One 1st deg rel early colon and ovarian | 6-029 H a c d | 6-030 H a c d | 6-031 H a c d | 6-032 H a c e | 6-033 H a c d | 6-034 H a c f | |
| One 1st deg rel late colon and ovarian | 6-035 H a c d | 6-036 H a d | 6-037 H a c d | 6-038 H a e | 6-039 H a d | 6-040 H a f | |
| One 1st deg rel early colon | 6-041 H a c d | 6-042 H a c d | 6-043 H c d | 6-044 H c e | 6-045 H c d | 6-046 H b c | |
| Two 1st deg rel late colon | 6-047 H a c e | 6-048 H a e | 6-049 H c e | 6-050 H e | 6-051 H e | 6-052 H b d | |
| One 1st deg rel late colon | 6-053 H a c d | 6-054 H a d | 6-055 H c d | 6-056 H e | 6-057 M d | 6-058 M b | |
| One 1st deg rel ovarian | 6-059 H a c f | 6-060 H a f | 6-061 M b c | 6-062 M b d | 6-063 A | 6-064 A | |
| No 1st deg rel w/colon and ovarian | | | | | | | |

FIG. 21

Table 2100:

| | One 1st deg early or late CHD, late DM, and early or late CVA | One 1st deg early CHD and late DM | One 1st deg late CHD and late DM | One 1st deg early CHD and early or late CVA | One 1st deg late CHD and early or late CVA | One 1st deg early or late CVA and late DM | One 1st deg early CHD | Two 1st deg late CHD | One 1st deg late CHD | One 1st deg early CVA | One 1st deg late CVA | One 1st deg late DM | No 1st deg CHD, late DM or CVA |
|---|---|---|---|---|---|---|---|---|---|---|---|---|---|
| One 1st deg early or late CHD, late DM, and early or late CVA | 12-001 H aikn (h, m) | 12-002 H abhik (m) | 12-003 H abik (h, m) | 12-004 H achin (m) | 12-005 H acin (h, m) | 12-006 H adkn (h, m) | 12-007 H ahi (m) | 12-008 H aj (h, m) | 12-009 H ai (h, m) | 12-010 H amn (h) | 12-011 H an (h, m) | 12-012 H ak (h, m) | 12-013 H a (h) |
| One 1st deg early CHD and late DM | | 12-014 H bhik | 12-015 H bhik | 12-016 H bchip (m) | 12-017 H bchip (m) | 12-018 H bdhk (m) | 12-019 H bhi | 12-020 H bhj | 12-021 H bhi | 12-022 H bhmp | 12-023 H bhp | 12-024 H bhk | 12-025 H bh |
| One 1st deg late CHD and late DM | | | 12-026 H bik | 12-027 H bchip (m) | 12-028 H bcip (m) | 12-029 H bdk (m) | 12-030 H bhi | 12-031 H bj | 12-032 H bi | 12-033 M bmp | 12-034 M bp | 12-035 M bk | 12-036 M b |
| One 1st deg early CHD and early or late CVA | | | | 12-037 H chin (m) | 12-038 H chin (m) | 12-039 H cdhnp (m) | 12-040 H chi (m) | 12-041 H chj (m) | 12-042 H chi | 12-043 H chmn | 12-044 H chn | 12-045 H chp (m) | 12-046 H ch (m) |
| One 1st deg late CHD and early or late CVA | | | | | 12-047 H cin (m) | 12-048 H cdnp (m) | 12-049 H chi (m) | 12-050 H cj (m) | 12-051 H ci (m) | 12-052 M cmn (m) | 12-053 M cn (m) | 12-054 M cp (m) | 12-055 M c (m) |
| One 1st deg early CVA and late DM | | | | | | 12-056 M dkn (m) | 12-057 H dhp (m) | 12-058 H dip (m) | 12-059 M dp (m) | 12-060 M dmn | 12-061 M dn | 12-062 M dk (m) | 12-063 M d (m) |
| One 1st deg early CHD | | | | | | | 12-064 H hi | 12-065 H hj | 12-066 H hi | 12-067 H hmf | 12-068 H hf | 12-069 H eh | 12-070 H h |

FIG. 22  2200 →

| | One 1st deg early or late CHD, late DM and early or late CVA | One 1st deg early CHD and late DM | One 1st deg late CHD and late DM | One 1st deg early CHD and early or late CVA | One 1st deg late CHD and early or late CVA | One 1st deg early or late CVA and late DM | One 1st deg early CHD | Two 1st deg late CHD | One 1st deg late CHD | One 1st deg early CVA | One 1st deg late CVA | One 1st deg LATE DM | No 1st deg CHD, late DM or CVA |
|---|---|---|---|---|---|---|---|---|---|---|---|---|---|
| Two 1st deg late CHD | | | | | | | | 12-071 H j | 12-072 H j | 12-073 H fim | 12-074 H fi | 12-075 H ei | 12-076 H i |
| One 1st deg late CHD | | | | | | | | | 12-077 H i | 12-078 M fm | 12-079 M f | 12-080 M e | 12-081 M o |
| One 1st deg early CVA | | | | | | | | | | 12-082 A | 12-083 A | 12-084 A | 12-085 A |
| One 1st deg late CVA | | | | | | | | | | | 12-086 A | 12-087 A | 12-088 A |
| One 1st deg late DM | | | | | | | | | | | | 12-089 A | 12-090 A |
| No 1st deg CHD, late DM or CVA | | | | | | | | | | | | | 12-091 A |

FIG. 23

| | One 1st deg early or late CHD, late DM and early or late CVA | One 1st deg early CHD and late DM | One 1st deg late CHD and late DM | One 1st deg early CHD and early or late CVA | One 1st deg late CHD and early or late CVA | One 1st deg early or late CVA and late DM | One 1st deg early CHD | Two 1st deg late CHD | One 1st deg late CHD | One 1st deg early CVA | One 1st deg late CVA | One 1st deg LATE DM | No 1st deg CHD, CVA or DM |
|---|---|---|---|---|---|---|---|---|---|---|---|---|---|
| One 2nd deg early or late CHD, late DM and early or late CVA | 12-092 H aikn (h, m) | 12-093 H abhik (m) | 12-094 M abik (h, m) | 12-095 H achin (m) | 12-096 M acin (h, m) | 12-097 M adkn (h, m) | 12-098 H ahi (m) | 12-099 H aj (h, m) | 12-100 M ai (h, m) | 12-101 A | 12-102 A | 12-103 A | |
| One 2nd deg early CHD and late DM | 12-104 H abhik (m) | 12-105 H bhik | 12-106 M bhik | 12-107 H bchip (m) | 12-108 M bchip (m) | 12-109 M bdhk (m) | 12-110 H bhi | 12-111 H bhj | 12-112 M bhi | 12-113 A | 12-114 A | 12-115 A | |
| One 2nd deg late CHD and late DM | 12-116 H abik (h, m) | 12-117 H bhik | 12-118 M bik | 12-119 H bchip (m) | 12-120 M bcip (m) | 12-121 M bdk | 12-122 H bhi | 12-123 H bj | 12-124 M bj | 12-125 A | 12-126 A | 12-127 A | |
| One 2nd deg early CHD and early or late CVA | 12-128 H abik (h, m) | 12-129 H bchip (m) | 12-130 M bchip (m) | 12-131 H chin (m) | 12-132 M chin (m) | 12-133 M cdhnp (m) | 12-134 H chi (m) | 12-135 H chj (m) | 12-136 M chi (m) | 12-137 A | 12-138 A | 12-139 A | |
| One 2nd deg late CHD and early or late CVA | 12-140 H achin (m) | 12-141 H bchip (m) | 12-142 M bcip (m) | 12-143 H chin (m) | 12-144 M cin (m) | 12-145 M cdnp (m) | 12-146 H chi (m) | 12-147 H cj (m) | 12-148 M cj (m) | 12-149 A | 12-150 A | 12-151 A | |
| One 2nd deg early or late CVA and late DM | 12-152 H adkn (h, m) | 12-153 H bdhk (m) | 12-154 M bdk (m) | 12-155 H cdhnp (m) | 12-156 M cdnp (m) | 12-157 M dkn (m) | 12-158 H dhp (m) | 12-159 H dip (m) | 12-160 M dp (m) | 12-161 A | 12-162 A | 12-163 A | |
| One 2nd deg early CHD | 12-164 H ahi (m) | 12-165 H bhi (m) | 12-166 M bhi | 12-167 H chi (m) | 12-168 M chi (m) | 12-169 M dhp (m) | 12-170 H hi | 12-171 H hj | 12-172 M hi | 12-173 A | 12-174 A | 12-175 A | |

Table 2400

| | One 1st deg early or late CHD, late DM and early or late CVA | One 1st deg early CHD and late DM | One 1st deg late CHD and DM | One 1st deg early CHD and late CVA | One 1st deg late CHD and early or late CVA | One 1st deg early or late CVA and late DM | One 1st deg early CHD | Two 1st deg late CHD | One 1st deg late CHD | One 1st deg early CVA | One 1st deg late CVA | One 1st deg late DM | No 1st deg CHD, CVA or DM |
|---|---|---|---|---|---|---|---|---|---|---|---|---|---|
| Two 2nd deg late CHD | 12-176 H aj (h,m) | 12-177 H bhj | 12-178 H bj | 12-179 H chj (m) | 12-180 H cj (m) | 12-181 M dip (m) | 12-182 H hj | 12-183 H j | 12-184 H j | 12-185 A | 12-186 A | 12-187 A | |
| One 2nd deg late CHD | 12-188 H ai (h,m) | 12-189 H bhi | 12-190 M bi | 12-191 H chi (m) | 12-192 M ci (m) | 12-193 M p (m) | 12-194 H hi | 12-195 H j | 12-196 M i | 12-197 A | 12-198 A | 12-199 A | |
| One 2nd deg early CVA | 12-200 H amn (h) | 12-201 H bhmp | 12-202 M bm | 12-203 H chmn | 12-204 M cmn | 12-205 M dmn | 12-206 H fhm | 12-207 H fim | 12-208 M fm | 12-209 A | 12-210 A | 12-211 A | |
| One 2nd deg late CVA | 12-212 H an (h,m) | 12-213 H bhp | 12-214 M b | 12-215 H chn (m) | 12-216 M cn (m) | 12-217 M d | 12-218 H fh | 12-219 H fi | 12-220 M f | 12-221 A | 12-222 A | 12-223 A | |
| One 2nd deg late DM | 12-224 H ak (h,m) | 12-225 H bhk | 12-226 M bk | 12-227 H ch (m) | 12-228 M cp (m) | 12-229 M dk (m) | 12-230 H eh | 12-231 H ei | 12-232 M e | 12-233 A | 12-234 A | 12-235 A | |
| No 2nd deg CHD, CVA or DM | | | | | | | | | | | | | |

FIG. 25

| | One 2nd deg early or late CHD, late DM, and early or late CVA | One 2nd deg early CHD and late DM | One 2nd deg late CHD and late DM | One 2nd deg early CHD and early or late CVA | One 2nd deg late CHD and early or late CVA | One 2nd deg early CHD and early or late CVA and late DM | One 2nd deg early CHD | Two 2nd deg late CHD | One 2nd deg late CHD | One 2nd deg early CVA | One 2nd deg late CVA | One 2nd deg late DM | No 2nd deg CHD CVA or DM |
|---|---|---|---|---|---|---|---|---|---|---|---|---|---|
| One 2nd deg early or late CHD, late DM, and early or late CVA | 12-236 M a i k n (h, m) | 12-237 M a b h i k (m) | 12-238 M a b i k (h, m) | 12-239 M a c h i n (m) | 12-240 M a c i n (h, m) | 12-241 M a d k n (h, m) | 12-242 M a h i (m) | 12-243 M a j (h, m) | 12-244 A | 12-245 A | 12-246 A | 12-247 A | 12-248 A |
| One 2nd deg early CHD and late DM | | 12-249 M b h i k | 12-250 M b h i k | 12-251 M b c h i p (m) | 12-252 M b c i p (m) | 12-253 M b d h k (m) | 12-254 M b h i (m) | 12-255 M b h j | 12-256 A | 12-257 A | 12-258 A | 12-259 A | 12-260 A |
| One 2nd deg late CHD and late DM | | | 12-261 M b i k | 12-262 M b c h i p (m) | 12-263 M b c i p (m) | 12-264 M b d k (m) | 12-265 M b h i (m) | 12-266 M b j | 12-267 A | 12-268 A | 12-269 A | 12-270 A | 12-271 A |
| One 2nd deg early CHD and early or late CVA | | | | 12-272 M c h i n (m) | 12-273 M c h i n (m) | 12-274 M c d h n p (m) | 12-275 M c h i (m) | 12-276 M c h j (m) | 12-277 A | 12-278 A | 12-279 A | 12-280 A | 12-281 A |
| One 2nd deg late CHD and early or late CVA | | | | | 12-282 M c i n (m) | 12-283 M c d n p (m) | 12-284 M c h i (m) | 12-285 M c j (m) | 12-286 A | 12-287 A | 12-288 A | 12-289 A | 12-290 A |
| One 2nd deg early or late CVA and late DM | | | | | | 12-291 M d k n (m) | 12-292 M d h p (m) | 12-293 M d i p (m) | 12-294 A | 12-295 A | 12-296 A | 12-297 A | 12-298 A |
| One 2nd deg early CHD | | | | | | | 12-299 M h i | 12-300 M h j | 12-301 A | 12-302 A | 12-303 A | 12-304 A | 12-305 A |

| | One 2nd deg early or late CHD, late DM, and early or late CVA | One 2nd deg early CHD and late DM | One 2nd deg late CHD and late DM | One 2nd deg early CHD and early or late CVA | One 2nd deg late CHD and early or late CVA | One 2nd deg early or late CVA and late DM | One 2nd deg early CHD | Two 2nd deg late CHD | One 2nd deg late CHD | One 2nd deg early CVA | One 2nd deg late CVA | One 2nd deg late DM | No 2nd deg CHD, CVA or DM |
|---|---|---|---|---|---|---|---|---|---|---|---|---|---|
| Two 2nd deg late CHD | | | | | | | | 12-306 M j | 12-307 M j | | | | 12-311 A |
| One 2nd deg late CHD | | | | | | | | | 12-312 A | 12-308 A | | | 12-316 A |
| One 2nd deg early CVA | | | | | | | | | | 12-313 A | 12-317 A | | 12-320 A |
| One 2nd deg late CVA | | | | | | | | | | | 12-318 A | 12-321 A | 12-323 A |
| One 2nd deg late DM | | | | | | | | | | | | 12-322 A | 12-325 A |
| No 2nd deg CHD, CVA or DM | | | | | | | | | | | | 12-324 A | 12-326 A |

| | One 1st deg early or late CVA, late DM and early or late CHD | One 1st deg early CVA and early or late CHD | One 1st deg late CVA and early or late CHD | One 1st deg early CVA and late DM | One 1st deg late CVA and late DM | One 1st deg early or late CHD and late DM | One 1st deg early CVA | Two 1st deg late CVA | One 1st deg late CVA | One 1st deg early CHD | One 1st deg late CHD | One 1st deg late DM | No 1st deg CHD late DM or CVA |
|---|---|---|---|---|---|---|---|---|---|---|---|---|---|
| One 1st deg early or late CVA, late DM and early or late CHD | 12-001 H aikn (h, l) | | | | | | | | | | | | |
| One 1st deg early CVA and early or late CHD | | 12-002 H achik (l) | 12-003 H acik (h, l) | 12-004 H abhin (l) | 12-005 H abin (h, l) | 12-006 H adkn (h, l) | 12-007 H ahi (l) | 12-008 H aj (h, l) | 12-009 H ai (h, l) | 12-010 H akl (h) | 12-011 H ak (h, l) | 12-012 H an (h, l) | 12-013 H a (h, l) |
| One 1st deg late CVA and early or late CHD | | 12-014 H chik (l) | 12-015 H chik (l) | 12-016 H bchip (l) | 12-017 H bchip (l) | 12-018 H cdhkp (l) | 12-019 H chi (l) | 12-020 H chj (l) | 12-021 H chi (l) | 12-022 H chkl (l) | 12-023 H chk (l) | 12-024 H chp (l) | 12-025 H ch (l) |
| One 1st deg early CVA and late DM | | | 12-026 H cik (l) | 12-027 H bchip (l) | 12-028 H bcip (l) | 12-029 H cdkp (l) | 12-030 H chi (l) | 12-031 H cj (l) | 12-032 H ci (l) | 12-033 H ckl (l) | 12-034 M ck (l) | 12-035 M cp (l) | 12-036 M c (l) |
| One 1st deg late CVA and late DM | | | | 12-037 H bhin | 12-038 H bhin | 12-039 H bdhn (l) | 12-040 H bhi (l) | 12-041 H bhj (l) | 12-042 H bhi (l) | 12-043 H bhlp (l) | 12-044 H bhp (l) | 12-045 H bhn (l) | 12-046 H bh (l) |
| One 1st deg early or late CHD and late DM | | | | | 12-047 H bin | 12-048 H bdn (l) | 12-049 H bhi (l) | 12-050 H bj | 12-051 H bi | 12-052 H blp | 12-053 M bp | 12-054 M bn | 12-055 M b |
| One 1st deg early CVA | | | | | | 12-056 M dkn (l) | 12-057 H dhp (l) | 12-058 H dip | 12-059 H dp | 12-060 H dkl | 12-061 M dk | 12-062 M dn | 12-063 M d |
| | | | | | | | 12-064 H hi | 12-065 H hi | 12-066 H hi | 12-067 H fhl | 12-068 H fh | 12-069 H eh | 12-070 H h |

| | One 1st deg early or late CVA, late DM and early or late CHD | One 1st deg early CVA and early or late CHD | One 1st deg late CVA and early or late CHD | One 1st deg early CVA and late DM | One 1st deg late CVA and late DM | One 1st deg early or late CHD and late DM | One 1st deg early CVA | Two 1st deg late CVA | One 1st deg late CVA | One 1st deg early CHD | One 1st deg late CHD | One 1st deg DM | No 1st deg CHD, late DM and CVA |
|---|---|---|---|---|---|---|---|---|---|---|---|---|---|
| Two 1st deg late CVA | | | | | | | | 12-071 H j | 12-072 H j | 12-073 H fil | 12-074 H fim | 12-075 H ei | 12-076 H i |
| One 1st deg late CVA | | | | | | | | | 12-077 H i | 12-078 H fl | 12-079 M f | 12-080 M e | 12-081 M o |
| One 1st deg early CHD | | | | | | | | | | 12-082 M kl | 12-083 M kl | 12-084 M gl | 12-085 A |
| One 1st deg late CHD | | | | | | | | | | | 12-086 A | 12-087 A | 12-088 A |
| One 1st deg late DM | | | | | | | | | | | | 12-089 A | 12-090 A |
| No 1st deg CVA, late DM or CHD | | | | | | | | | | | | | 12-091 A |

FIG. 29

| | One 1st deg early CVA, late DM and early or late CHD | One 1st deg early CVA and early or late CHD | One 1st deg late CVA and early or late CHD | One 1st deg early CVA and late DM | One 1st deg late CVA and late DM | One 1st deg early or late CHD and late DM | One 1st deg early CVA | Two 1st deg late CVA | One 1st deg late CVA | One 1st deg early CHD | One 1st deg late CHD | One 1st deg late DM | No 1st deg CHD, late DM or CVA |
|---|---|---|---|---|---|---|---|---|---|---|---|---|---|
| One 2nd deg early or late CVA, late DM and early or late CHD | 12-092<br>H<br>a i k n<br>(h,l) | 12-093<br>H<br>a c h i k<br>(l) | 12-094<br>M<br>a c i k<br>(h,l) | 12-095<br>H<br>a b h i n<br>(l) | 12-096<br>M<br>a b i n<br>(h,l) | 12-097<br>M<br>a d k n<br>(h,l) | 12-098<br>H<br>a h i<br>(l) | 12-099<br>H<br>a j<br>(h,l) | 12-100<br>M<br>a i<br>(h,l) | 12-101<br>M<br>a k l<br>(h) | 12-102<br>A | 12-103<br>A | |
| One 2nd deg early CVA and early or late CHD | 12-104<br>M<br>a c h i k<br>(l) | 12-105<br>H<br>c h i k<br>(l) | 12-106<br>M<br>c h i k<br>(l) | 12-107<br>H<br>b c h i p<br>(l) | 12-108<br>M<br>b c h i p<br>(l) | 12-109<br>M<br>c d h k p<br>(l) | 12-110<br>H<br>c h i<br>(l) | 12-111<br>H<br>c h j<br>(l) | 12-112<br>M<br>c h i<br>(l) | 12-113<br>M<br>c h k l | 12-114<br>A | 12-115<br>A | |
| One 2nd deg late CVA and early or late CHD | 12-116<br>H<br>a c i k<br>(h,l) | 12-117<br>H<br>c h i k<br>(l) | 12-118<br>M<br>c i k<br>(l) | 12-119<br>H<br>b c h i p<br>(l) | 12-120<br>M<br>b c i p<br>(l) | 12-121<br>M<br>c d k p<br>(l) | 12-122<br>H<br>c h i<br>(l) | 12-123<br>H<br>c j<br>(l) | 12-124<br>M<br>c i<br>(l) | 12-125<br>M<br>c k l | 12-126<br>A | 12-127<br>A | |
| One 2nd deg early CVA and late DM | 12-128<br>H<br>a b h i n<br>(l) | 12-129<br>H<br>b c h i p<br>(l) | 12-130<br>M<br>c i k<br>(l) | 12-131<br>H<br>b h i n<br>(l) | 12-132<br>M<br>b c h i n<br>(l) | 12-133<br>M<br>b d h n<br>(l) | 12-134<br>H<br>b h i<br>(l) | 12-135<br>H<br>c j<br>(l) | 12-136<br>M<br>b h i<br>(l) | 12-137<br>M<br>b h l p | 12-138<br>A | 12-139<br>A | |
| One 2nd deg late CVA and late DM | 12-140<br>H<br>a b i n<br>(h,l) | 12-141<br>H<br>b c h i p<br>(l) | 12-142<br>M<br>b c i p<br>(l) | 12-143<br>H<br>b h i n<br>(l) | 12-144<br>M<br>b i n<br>(l) | 12-145<br>M<br>b d n<br>(l) | 12-146<br>H<br>b h i<br>(l) | 12-147<br>H<br>b j<br>(l) | 12-148<br>M<br>b i<br>(l) | 12-149<br>M<br>b i p | 12-150<br>A | 12-151<br>A | |
| One 2nd deg late CHD and late DM | 12-152<br>H<br>a d k n<br>(h,l) | 12-153<br>H<br>c d h p<br>(l) | 12-154<br>M<br>c d k p<br>(l) | 12-155<br>H<br>b d h n<br>(l) | 12-156<br>M<br>b d n<br>(l) | 12-157<br>M<br>d k n<br>(l) | 12-158<br>H<br>d h p<br>(l) | 12-159<br>H<br>d i p<br>(l) | 12-160<br>M<br>d p<br>(l) | 12-161<br>M<br>d k l | 12-162<br>A | 12-163<br>A | |
| One 2nd deg early CVA | 12-164<br>H<br>a h i<br>(l) | 12-165<br>H<br>c h i<br>(l) | 12-166<br>M<br>c h i<br>(l) | 12-167<br>H<br>b h i<br>(l) | 12-168<br>M<br>b h i<br>(l) | 12-169<br>M<br>d h p<br>(l) | 12-170<br>H<br>h i<br>(l) | 12-171<br>H<br>h j<br>(l) | 12-172<br>M<br>h i | 12-173<br>M<br>f h l | 12-174<br>A | 12-175<br>A | |

| | One 1st deg early CVA, late DM and early or late CHD | One 1st deg early CVA and early or late CHD | One 1st deg late CVA and early or late CHD | One 1st deg early CVA and late DM | One 1st deg late CVA and late DM | One 1st deg early or late CHD and late DM | One 1st deg early CVA | Two 1st deg late CVA | One 1st deg late CVA | One 1st early deg CHD | One 1st deg late CHD | One 1st deg late DM | No 1st deg CHD, late DM or CVA |
|---|---|---|---|---|---|---|---|---|---|---|---|---|---|
| Two 2nd deg late CVA | 12-176 H a j (h, l) | 12-177 H c h j (l) | 12-178 H c j (l) | 12-179 H b h j | 12-180 H b j | 12-181 M d j p (l) | 12-182 H h j | 12-183 H j | 12-184 H j | 12-185 M f j l | 12-186 M f l | 12-187 A | |
| One 2nd deg late CVA | 12-188 H a i (h, l) | 12-189 H c h i (l) | 12-190 M c i (l) | 12-191 H b h i | 12-192 M b i | 12-193 M d i p (l) | 12-194 H h i | 12-195 H j | 12-196 M i | 12-197 M f l | 12-198 A | 12-199 A | |
| One 2nd deg early CHD | 12-200 H a k l (h) | 12-201 H c h k l (l) | 12-202 M c k l | 12-203 H b h l p | 12-204 M b l p | 12-205 M d l g | 12-206 H f h l | 12-207 H f l l | 12-208 M f l | 12-209 M k l | 12-210 A | 12-211 A | |
| One 2nd deg late CHD | 12-212 H a k (h, l) | 12-213 H c h k (l) | 12-214 M c k (l) | 12-215 H b h p | 12-216 M b p | 12-217 M d (l) | 12-218 H h | 12-219 H i | 12-220 M o | 12-221 A | 12-222 A | 12-223 A | |
| One 2nd deg late DM | 12-224 H a n (h, l) | 12-225 H c h p (l) | 12-226 M c p (l) | 12-227 H b h n | 12-228 M b n | 12-229 M d (l) | 12-230 H h e | 12-231 H i e | 12-232 M o e | 12-233 A | 12-234 A | 12-235 A | |
| No 2nd deg CVA, CHD and or DM | | | | | | | | | | | | | |

FIG. 31

| | One 2nd deg early or late CVA, late DM and early or late CHD | One 2nd deg early CVA and early or late CHD | One 2nd deg late CVA and early or late CHD | One 2nd deg early CVA and late DM | One 2nd deg late CVA and late DM | One 2nd deg early or late CHD and late DM | One 2nd deg early CVA | Two 2nd deg late CVA | One 2nd deg late CVA | One 2nd deg early CHD | One 2nd deg late CHD | One 2nd deg late DM | No 2nd deg CHD, late DM or CVA |
|---|---|---|---|---|---|---|---|---|---|---|---|---|---|
| One 2nd deg early or late CVA, late DM and early or late CHD | 12-236 M a l k n (h,l) | 12-237 M a c h i k (l) | 12-238 M a c i k (h,l) | 12-239 M a b h i n (l) | 12-240 M a b i n (h,l) | 12-241 M a d k n (h,l) | 12-242 M a h i (l) | 12-243 M a j (h,l) | 12-244 M a i (h,l) | 12-245 M a k l (h) | 12-246 A | 12-247 A | 12-248 A |
| One 2nd deg early CVA and early or late CHD | | 12-249 M c h i k (l) | 12-250 M c h i k (l) | 12-251 M b c h i p (l) | 12-252 M b c h i p (l) | 12-253 M c d h k p (l) | 12-254 M c h i (l) | 12-255 M c h j (l) | 12-256 M c h i (l) | 12-257 M c h k l (h) | 12-258 A | 12-259 A | 12-260 A |
| One 2nd deg late CVA and early or late CHD | | | 12-261 M c l k (l) | 12-262 M b c h i p (l) | 12-263 M b c l p (l) | 12-264 M c d k p (l) | 12-265 M c h i (l) | 12-266 M c j (l) | 12-267 M c i (l) | 12-268 M c k l | 12-269 A | 12-270 A | 12-271 A |
| One 2nd deg early CVA and late DM | | | | 12-272 M b h i n | 12-273 M b h i n | 12-274 M b d h n | 12-275 M b h i | 12-276 M b h j | 12-277 M b h i | 12-278 M b h l p | 12-279 A | 12-280 A | 12-281 A |
| One 2nd deg late CVA and late DM | | | | | 12-282 M b i n | 12-283 M b d n | 12-284 M b h i | 12-285 M b j | 12-286 M b i | 12-287 M b l p | 12-288 A | 12-289 A | 12-290 A |
| One 2nd deg early or late CHD and late DM | | | | | | 12-291 M d k n | 12-292 M d h p | 12-293 M d i p | 12-294 M d p | 12-295 M d k l | 12-296 A | 12-297 A | 12-298 A |
| One 2nd deg early CVA | | | | | | | 12-299 M h i | 12-300 M h j | 12-301 M h i | 12-302 M f h l | 12-303 A | 12-304 A | 12-305 A |

| | One 2nd early or late CVA, late DM and early or late CHD | One 2nd deg early CVA and early or late CHD | One 2nd deg late CVA and early or late CHD | One 2nd deg early CVA and late DM | One 2nd deg late CVA and late DM | One 2nd deg early or late CHD and late DM | One 2nd deg early CVA | Two 2nd deg late CVA | One 2nd deg late CVA | One 2nd deg early CHD | One 2nd deg late CHD | One 2nd deg DM | No 2nd deg CHD, late DM or CVA |
|---|---|---|---|---|---|---|---|---|---|---|---|---|---|
| Two 2nd deg late CVA | | | | | | | | 12-306 M j | 12-307 M j | 12-308 M f i l | 12-309 M f i | 12-310 M e i | 12-311 M i |
| One 2nd deg late CVA | | | | | | | | | 12-312 A | 12-313 A | 12-314 A | 12-315 A | 12-316 A |
| One 2nd deg early CHD | | | | | | | | | | 12-317 A | 12-318 A | 12-319 A | 12-320 A |
| One 2nd deg late CHD | | | | | | | | | | | 12-321 A | 12-322 A | 12-323 A |
| One 2nd deg late DM | | | | | | | | | | | | 12-324 A | 12-325 A |
| No 2nd deg CVA, CHD and late DM | | | | | | | | | | | | | 12-326 A |

|  | Two 1st deg late DM | One 1st deg late DM | No 1st deg DM |
|---|---|---|---|
| Two 1st deg late DM | 1-001 H a | 1-002 H a | 1-003 H b |
| One 1st deg late DM |  | 1-004 H b | 1-005 M c |
| No 1st deg DM |  |  | 1-006 A |

|  | Two 1st deg late DM | One 1st deg late DM | No 1st deg DM |
|---|---|---|---|
| Two 2nd deg late DM | 1-007 H a | 1-008 H a |  |
| One 2nd deg late DM | 1-009 H a | 1-0010 M b |  |
| No 2nd deg DM |  |  |  |

|  | Two 2nd deg late DM | One 2nd deg late DM | No 2nd deg DM |
|---|---|---|---|
| Two 2nd deg late DM | 1-011 H a | 1-012 H a | 1-013 M b |
| One 2nd deg late DM |  | 1-014 M b | 1-015 A |
| No 2nd deg DM |  |  | 1-016 A |

FIG. 37

Welcome to Family Healthware

Family Healthware is a free tool that collects information on your:
- lifestyle behaviors
- use of screening tests
- family history of six major diseases and produces a personalized report that:
- analyzes your family history as a risk factor for disease
- recommends screening, lifestyle and other changes to improve your health.

Click to learn about:

Family Healthware

Family History & Health

Returning Users

Username:

Password:

Go

Forgot your username or password?

New Users

Begin your Family Healthware assessment today...

Create My Account

Family Healthware is not designed to replace medical advice and discussions with a health professional. You should talk to your health professional before making a decision about your medical care.

FIG. 38

*FamilyHealthware*
*Using Family History to Promote Health*

Glossary  Logout

☐ My Profile
  Username/Password
  Personal Information
  Health Behaviors
  Screening Tests ☐ My Family Profile
  Family Profile Introduction
  Create Family Tree
  Add Family Member ☐ My Report

3800

My Profile – Username/Password

This information will allow you to access your account in the future and keep your information secure.

Username and Password

Username: [         ]  Needs at least 4 characters

Password: [         ]  Needs at least 6 characters

Re-enter password: [         ]

Study Code: [         ]

Password Reminder

Select a question prompt: [PLEASE SELECT ▼]

Enter the answer to your question prompt: [         ]

If you forget your password, we will ask you to provide this answer to verify your identity.

[Save & Continue]

Privacy Policy: We will not share information collected, when you use Family Healthware, with anyone outside this research project.

FIG. 40

Logo

My Profile
1 Username/Password
2 Personal Information
3 My Health History
4 Health Behaviors
5 Screening Tools

My Family Profile

My Report

My Profile – My Health History

Health History for Jane Smith

Please enter information about your personal health history. It is important that you indicate whether you have had each disease and at what age. Complete and accurate information will provide you with a more accurate assessment and the most appropriate prevention plan.

What is your current height? [ ] feet [ ] inches

What is your current weight? [ ] lbs.
(pregnant women should indicate weight prior to pregnancy)

| Disease | Did you ever have this disease? |
|---|---|
| Coronary Heart Disease ? | Please select one: ▼ |
| Stroke ? | Please select one: ▼ |
| Diabetes ? | Please select one: ▼ |
| Colon Cancer ? | Please select one: ▼ |
| Breast Cancer ? | Please select one: ▼ |
| Ovarian Cancer ? | Please select one: ▼ |

[Previous Screen]　　[Save & Continue]

Logout

Family Healthcare
*Using Family History to Promote Health*

Glossary  Logout

☐ My Profile
- Username/Password
- Personal Information
- Health Behaviors
- Screening Tests ☐ My Family Profile
- Family Profile Introduction
- Create Family Tree
- Add Family Member ☐ My Report

My Profile – My Screening Tests

Question 1 of 8

Cholesterol

Blood cholesterol is a fatty substance found in the blood. Have you had your blood cholesterol checked by a health professional?

PLEASE SELECT:

PLEASE SELECT:
Never
Yes, within the past year
Yes, 1 to 2 years ago
Yes, 3 to 5 years ago
Yes, 6 to 10 years ago
Yes, more than 10 years ago
Don't know/Not sure Previous Screen    Save & Continue

My Profile
Username/Password
Personal Information
Health Behaviors
Screening Tests My Family Profile
Family Profile Introduction
Create Family Tree
Add Family Member
Mother: Paula
Mother's Mother
Mother's Father
Father
Father's Mother
Father's Father My Report
Introduction
Family Tree
Assessment Summary
Coronary Heart Disease
Stroke
Diabetes
Colon Cancer
Screening Tests
Lifestyle Changes

4300

My Profile – Username/Password

This information will allow you to access your account in the future and keep your information secure.

Username and Password

Username: cancer

Password: ******   Needs at least 6 characters

Re-enter password: ******

Study Code:

Password Reminder

Select a question prompt: Favorite pet's name?

Enter the answer to your question prompt: Nikki

If you forget your password, we will ask you to provide this answer to verify your identity.

Privacy Policy: We will not share information collected, when you use Family Healthware, with anyone outside this research project.

Save & Continue

FIG. 45

*Family Healthware*
Using Family History to Promote Health

Glossary Logout

[+] My Profile

[−] My Family Profile
  Family Profile Introduction
  Create Family Tree
  Add Family Member
  *Edits*
  Mother's Mother
  Mother's Father
  Father
  Father's Mother
  Father's Father

[+] My Report

My Family Profile
Health History of My Mother

Please enter a name for your Mother: [ ]

Delete Member

☐ Check if you don't know if this relative had any of these diseases.

Did your mother ever have...?

| | Yes | No | Don't Know | Age at first diagnosis (estimate if not sure) |
|---|---|---|---|---|
| Coronary Heart Disease | ○ | ○ | ○ | |
| Stroke | ○ | ○ | ○ | |
| Diabetes | ○ | ○ | ○ | |
| Colon Cancer | ○ | ○ | ○ | |
| Breast Cancer | ○ | ○ | ○ | |
| Ovarian Cancer | ○ | ○ | ○ | |

4500

Previous Screen    Save & Continue

Family Healthcare
*Using Family History to Promote Health*

Glossary  Logout

[+] My Profile
[+] My Family Profile
[−] My Report
  Introduction
  Family Tree
  Assessment Summary
  Coronary Heart Disease
  Stroke
  Diabetes
  Colon Cancer
  Breast Cancer
  Ovarian Cancer
  Screening Tests
  Lifestyle Changes
  Print My Report Disease Resources
  Lifestyle Resources
  Family History Resources

My Report – Assessment Summary

Learn more about family history as a risk factor for disease.

| Disease: | Family history's impact on risk: |
|---|---|
| Coronary Heart Disease | STRONG |
| Stroke | WEAK |
| Diabetes | WEAK |
| Colon Cancer | WEAK |
| Breast Cancer | WEAK |
| Ovarian Cancer | WEAK |

[Print My Report]  [Previous Screen]  [Continue]

Family Healthware
Using Family History to Promote Health

Glossary  Logout

⊞ My Profile
⊞ My Family Profile
⊟ My Report
  Introduction
  Family Tree
  Assessment Summary
  Coronary Heart Disease
  Stroke
  Diabetes
  Colon Cancer
  Breast Cancer
  Ovarian Cancer
  Screening Tests
  Lifestyle Changes
  Print My Report Disease Resources
  Lifestyle Resources
  Family History Resources

My Report – Coronary Heart Disease

The impact of your family history on Coronary Heart Disease risk is: STRONG

Why your family history is a risk factor:
- At least one family member with coronary heart disease at a young age. Early-onset disease is a sign of a greater number of cardiovascular risk factors.

The following can help reduce your overall risk:

Screening Tests
- You may benefit from blood sugar testing because of your family history. Talk to your health professional.
- Get your blood pressure checked.
- Continue cholesterol testing.

Lifestyle Changes
- Maintain a healthy weight.
- Continue to avoid smoking.
- Increase your physical activity.
- Continue to eat at least 5 servings of fruits and vegetables a day.

PERSONAL ASSESSMENT INCLUDING FAMILIAL RISK ANALYSIS FOR PERSONALIZED DISEASE PREVENTION PLAN

CROSS-REFERENCE TO RELATED APPLICATIONS

This application is a U.S. national stage application of International Application No. PCT/US2006/003968, filed Feb. 2, 2006, which was published in English under PCT Article 21(2), which in turn claims the benefit of U.S. Provisional Application No. 60/650,076 to Scheuner et al., filed Feb. 3, 2005, entitled, "FAMILIAL RISK ANALYSIS FOR DETERMINING A DISEASE PREVENTION PLAN," all of which are hereby incorporated herein by reference.

FIELD

The field relates to preventive medicine and risk analysis of disease.

BACKGROUND

Determining risk factors for disease can be helpful for assessing an individual's overall risk for a disease and in creating a plan to modify an individual's risk of developing a disease. Medical providers are under increasing pressure from governments, medical specialty organizations, managed care, and patients to practice preventive medicine. Similarly, health organizations and insurance companies are beginning to recognize that risk analysis of disease and preventive medicine can be a very cost effective strategy for providing care. Medical screening and prevention guidelines for many chronic disorders have been developed by governments and medical organizations to facilitate risk analysis of disease and preventive medicine practice. However, such guidelines can be slow to be adopted, sometimes poorly understood, counter to historical practice, and can be perceived as cumbersome, difficult to use, not readily accessible or confusing by both medical providers and patients. Similarly, the guidelines do not incorporate comprehensive personal health behaviors or family health history information to determine a patient-specific or personalized risk of disease and disease prevention plan. Accordingly, there remains a need to better assess disease risk and communicate risk to patients.

SUMMARY

Family health history information can be used to assess familial risk for common diseases of adulthood and determine early detection and prevention medical strategies. Along with familial risk, other factors can be included to generate personalized disease prevention recommendations. For example, personal health history information, personal health behavior information (e.g., information about health-related personal practices, information about whether the subject has had one or more screening tests performed, or both), or both can be collected and assessed to generate personalized disease prevention recommendations based on the information collected. Such recommendations can be based on risk scenarios. Combining and personalizing such information can encourage preventive health care.

In addition, information can be collected about the disease history of a person and the person's first and second degree relatives (e.g., mother, father, children, siblings, grandparents, aunts and uncles) and then analyzed to determine familial risk for developing common chronic diseases (e.g., coronary heart disease, stroke, type 2 diabetes, and colorectal, breast, and ovarian cancer). Assessed familial risk of disease can then be used to determine recommendations for disease prevention and screening that are targeted to familial risk.

Recommendations for disease prevention and screening based on familial risk (e.g., combined with personal health behavior information) can be used to provide a disease prevention plan that encourages a person to make behavior changes that reduce the risk of disease and utilize preventive health services.

The techniques described herein can be applied to any number of diseases where determining familial risk of disease and a disease prevention plan based on family history, as well as personal characteristics, health history and behaviors are desired.

Additional features and advantages of the technologies described herein will be made apparent from the following detailed description of illustrated embodiments, which proceeds with reference to the accompanying drawings.

BRIEF DESCRIPTION OF THE DRAWINGS

FIG. 3 is a flowchart showing an exemplary method for determining familial risk of one or more diseases of interest for a subject.

FIGS. 9, 10, and 11 are exemplary familial risk matrices for determining familial risk of breast cancer.

Figure 12:
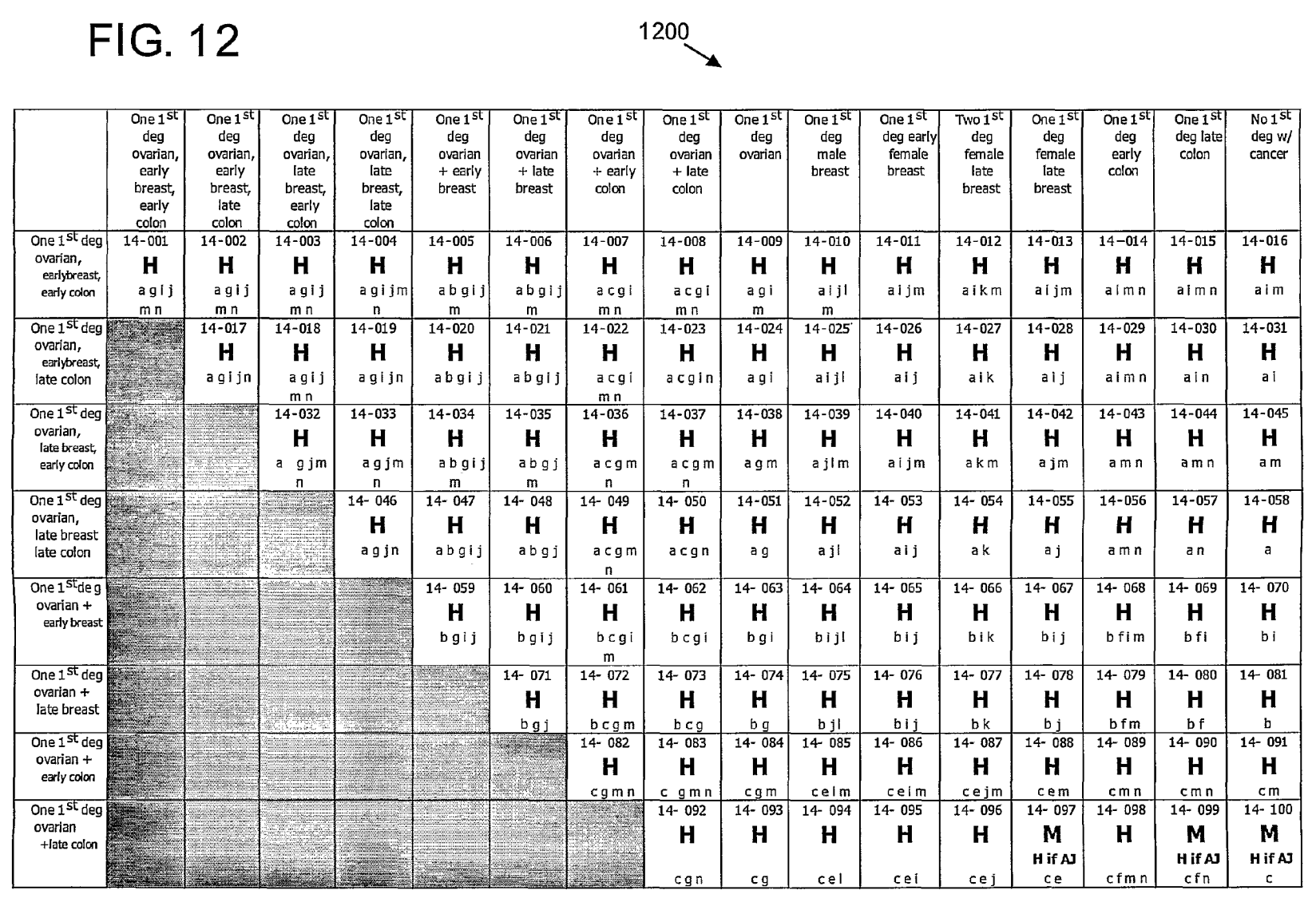

FIGS. 12, 13, 14, 15, 16, and 17 are exemplary familial risk matrices for determining familial risk of ovarian cancer.

FIGS. 18, 19, and 20 are exemplary familial risk matrices for determining familial risk of colon cancer.

FIGS. 21, 22, 23, 24, 25, and 26 are exemplary familial risk matrices for determining familial risk of coronary heart disease.

FIGS. 27, 28, 29, 30, 31, and 32 are exemplary familial risk matrices for determining familial risk of stroke.

FIGS. 33, 34, and 35 are exemplary familial risk matrices for determining familial risk of type 2 diabetes.

FIGS. 37-58 are screen shots from an exemplary implementation of a computer-implemented method for both determining the behavioral and familial risk of one or more diseases of interest in a subject and determining a disease prevention plan for a subject.

DETAILED DESCRIPTION

Overview of Technologies

Figure 1A:
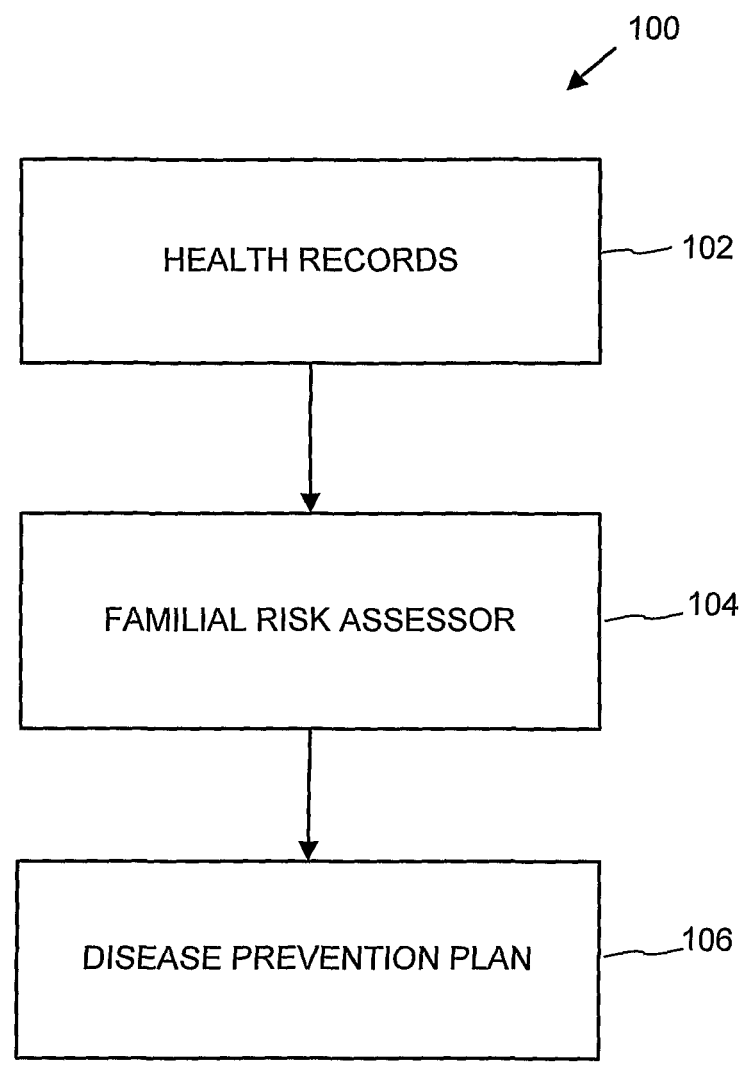
FIG. 1A is a block diagram of an exemplary system for determining a disease prevention plan for a subject based on familial risk.

The technologies described herein can be used in any of a variety of scenarios in which determination of familial risk of one or more diseases of interest and/or determination of a disease prevention plan based on familial risk of disease is useful. Personal behaviors can be included in the assessment, resulting in a determination of personal risk.

A disease prevention plan includes any general or specific prevention recommendations for reducing the risk of developing one or more diseases of interest. For example, recommendations can include screening for early detection of a disease of interest and/or screening for indicators of additional risk (e.g., specialized tests, genetic evaluations, and genetic testing). The plan can include recommendations for continuation or modification of behavior (e.g., increase consumption of fruits and vegetables).

A disease of interest includes any disease for which familial risk is assessed for a subject. In practice, diseases of interest include common diseases that result from complex interactions of multiple genes with multiple behavioral environmental factors. For example, heart disease (e.g., coronary heart disease), stroke, diabetes, colorectal cancer, breast cancer, and ovarian cancer can be diseases of interest.

An indicator disease includes any disease associated with indicating or otherwise correlating with an increased risk of developing a disease of interest. For example, ovarian cancer can be an indicator disease for breast cancer. In some cases, a disease can be an indicator disease for itself.

A first degree relative includes blood relatives, such as parents, siblings, or children. First degree relatives share one half of their genes in common.

A second degree relative includes aunts, uncles, nieces, nephews, and grandparents. Second degree relatives share one quarter of their genes in common.

Family health history information includes disease history of a subject's biological relatives. For example, family health history information can include disease history of first and second degree relatives, as well as disease history of more distant relatives. Disease history, for example, can include the number of first and second degree relatives, whether a relative has a disease of interest or indicator disease, gender of affected relatives, lineage of affected relatives (e.g., maternal or paternal side of the family), and the age of the relative at time of diagnosis of disease of interest or indicator disease.

Personal health history information includes name, date of birth, gender, age, race/ethnicity, height, weight, whether the subject currently has any disease of interest or indicator disease, personal health behavior information, or any combination thereof.

Personal health behavior information includes information related to health-related personal practices. Such practices can include smoking or other tobacco use, body mass index (BMI), level of physical activity (e.g., exercise), diet (e.g., daily servings of fruits and vegetables), alcohol use, aspirin use, and the like. Personal health behavior information can also include whether the subject has had one or more screening tests performed. Information about any one or more of these can be collected from the subject.

Familial risk (e.g., of disease) includes a likelihood of developing a disease (e.g., a disease of interest) based on family history. In any of the examples herein, a metric of familial risk of disease can be determined and expressed quantitatively. In any of the examples herein, a metric of familial risk of disease can be determined and expressed qualitatively (e.g., as a risk assessment category out of three or more categories). For example, familial risk of a disease can be categorized as high (e.g., strong), moderate, or low (e.g., weak) based at least on the number of first and second degree relatives having an indicator disease, the relatives' age of onset of the indicator disease, and the like. Alternatively, another measure can be presented (e.g., a numerical rating, a percentage rating, or the like).

Screening tests include any test that screens for disease or risk factors associated with disease. For example, screening tests can include clinical breast exams, mammograms, fecal occult blood tests, sigmoidoscopy, colonoscopy, blood cholesterol test, blood pressure test, blood sugar test, and the like.

A predetermined familial disease history scenario includes any family health history information of any relative that may be associated with familial risk. For example, the scenario in which a first degree relative has a disease of interest can be a predetermined familial disease history scenario. Other scenarios include how many relatives of a particular degree of relationship developed one or more indicator diseases, as well as age of onset of disease (e.g., early or late onset) for such relatives.

Intersection of two predetermined familial disease history scenarios includes situations in which a subject has two predetermined familial disease history scenarios. When the information is referenced with a disease matrix, the two predetermined familial health history scenarios meet in a risk-indicating familial history matrix cell, and the familial risk assessment is assigned based on the intersection of the two scenarios. A disease prevention plan can also be constructed based on the matrix cell.

Familial risk clarifiers include qualifying statements which clarify or further explain the assignment of familial risk of disease. For example, familial risk clarifiers can be used in the explanation of familial risk to subjects, and as part of a disease prevention plan.

Adoption status can indicate whether the subject was adopted and can be included in any of the information, such as in the personal health history information.

Example 1

Exemplary System for Determining a Disease Prevention Plan for a Subject Based on Familial Risk FIG. 1A shows an exemplary system 100 for determining a disease prevention plan for a subject based on familial risk.

Health records 102 of a subject are obtained and input into a familial risk assessor 104 to assess the familial risk of one or more diseases and determine a disease prevention plan 106.

The familial risk assessor 104 can employ any combination of technologies, such as those, described herein, to determine the disease prevention plan 106 for the subject.

Methods for determining familial risk and a disease prevention plan for a subject are described in detail below.

Example 2

Exemplary Ages

In any of the examples herein, an age of onset of disease or age of diagnosis of disease can be an age range, particular age, age category (e.g., early, late, or the like), or other indication of age.

Although particular ages are shown in some examples (e.g., in age ranges), other age groupings can be used.

Example 3

Exemplary Method for Determining Familial Risk of Disease for a Subject

Figure 1B:
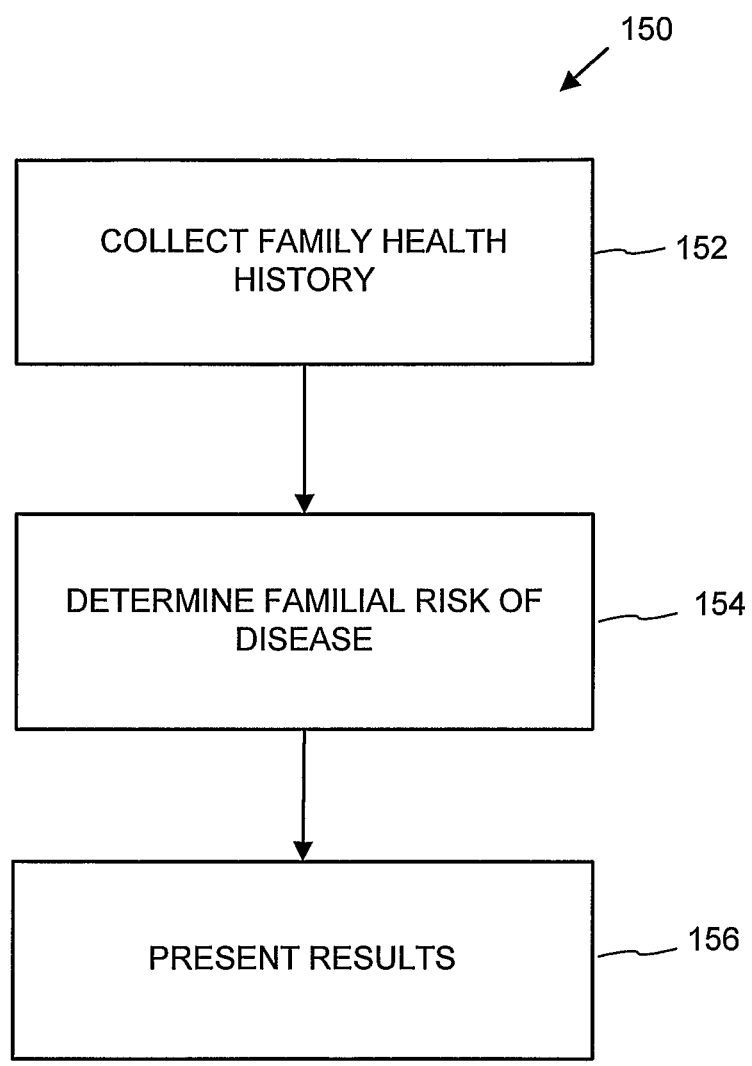
FIG. 1B is a flowchart showing an exemplary method for determining familial risk of disease for a subject.

FIG. 1B shows an exemplary method 150 for determining familial risk of disease for a subject.

At 152, family health history is collected. For example, disease history of a subject's first and second degree biological relatives including the number of first and second degree relatives, the lineage and gender of the first and second degree relatives, whether a relative has the disease of interest or an indicator disease, and the age of the relative at time of diagnosis of the disease of interest or indicator disease can be collected.

At 154, familial risk of disease is determined by analyzing family health history. For example, predetermined family disease history scenarios can be analyzed.

At 156, results of the determination of familial risk of disease are presented. For example, familial risk of disease for one or more diseases of interest can be presented as high (e.g., strong), moderate, or low (e.g., weak). Familial risk clarifiers can also be presented.

The method described in this or any of the other examples can be a computer-implemented method performed via computer-executable instructions in one or more computer-readable media. Any of the actions shown can be performed by software incorporated within an electronic medical record system or any other health information system.

Example 4

Figure 2A:
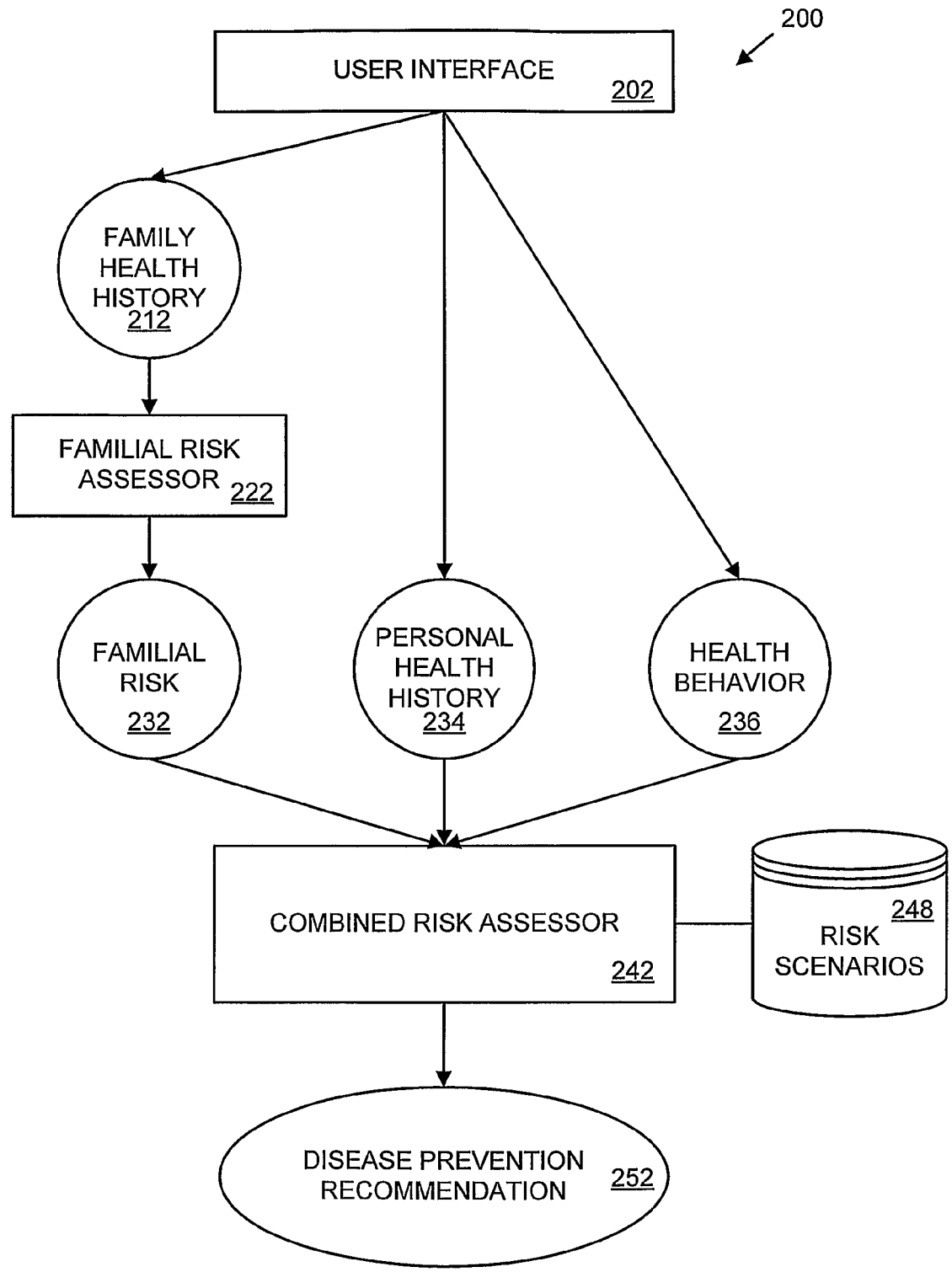
FIG. 2A is a block diagram of an exemplary system for providing personalized disease prevention recommendations for a subject.

Exemplary System for Providing a Personalized Disease Prevention Recommendations for a Subject FIG. 2A shows an exemplary system 200 for providing one or more personalized disease prevention recommendations for a subject. In the example, a user interface 202 collects information from a subject. Such information can include family health history information 212 for a subject, personal health history information 234 for a subject, and personal health behavior information 236 for a subject.

A familial risk assessor 222 is configured to analyze the family health history 212 and output a measure (e.g., any of the metrics described herein) of familial risk of disease 232 for one or more diseases.

A combined risk assessor 242 is configured to analyze the familial risk of disease 232, the personal health history information 234, the personal health behaviors history information 236, or some combination thereof to generate a disease prevention recommendation 252. The combined risk assessor 242 can comprise various sub-assessors (e.g., a personal health behavior assessor and the like). In some cases, the combined risk assessor 242 may detect that additional information can be gathered to provide a superior recommendation. Responsive to such detection, the assessor 242 can direct collection of the additional information from the subject.

The combined risk assessor 242 can consult one or more risk scenarios 248 to generate and provide one or more personalized disease prevention recommendations 252. The disease prevention recommendations 252 can be included as part of a disease prevention plan as described herein.

Example 5

Figure 2B:
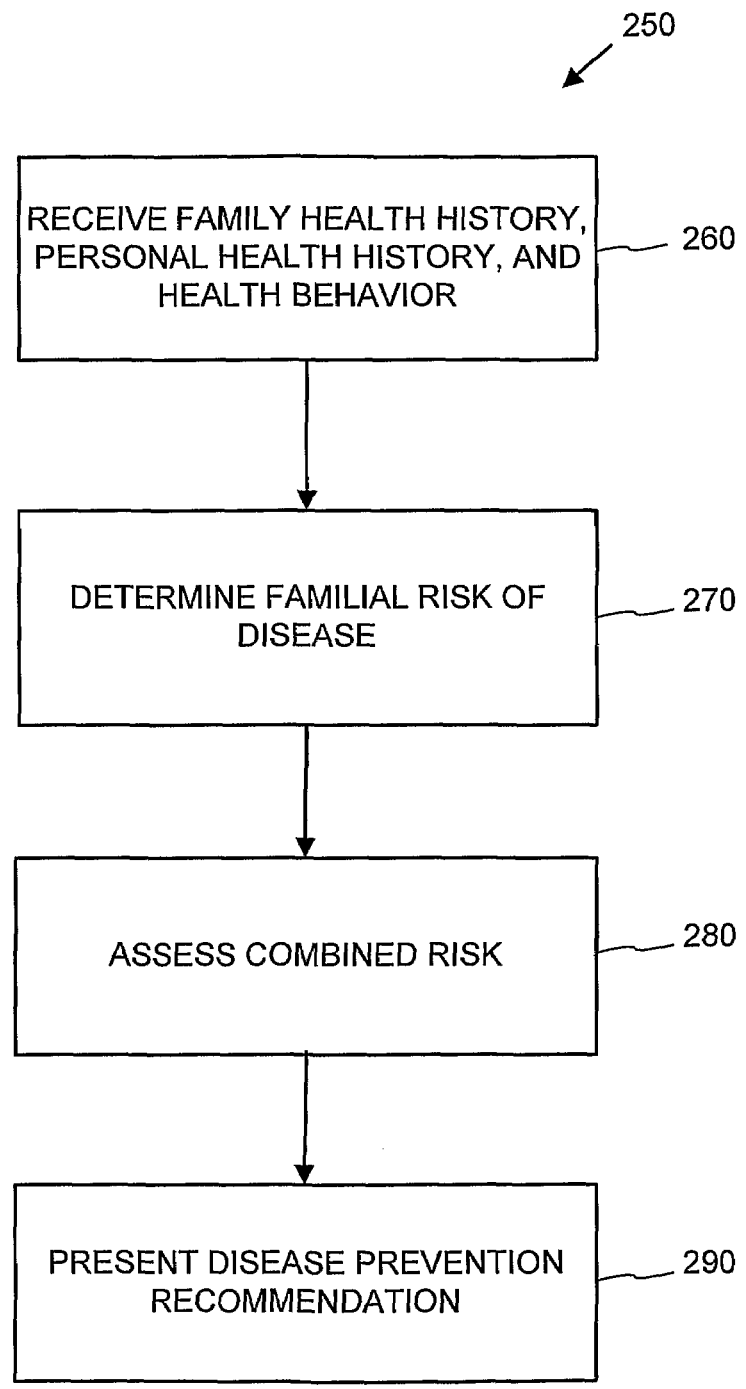
FIG. 2B is a flowchart showing an exemplary method of providing personalized disease prevention recommendations for a subject.

Exemplary Method for Providing Personalized Disease Prevention Recommendations for a Subject FIG. 2B shows an exemplary method 250 of providing a personalized disease prevention recommendation for a subject and can be performed on a system such as that shown in FIG. 2A.

In the example, the family health history information, personal health history information, and personal health behavior information for a subject are received at 260. For example, such information can be collected via any of the user interface techniques described herein.

Then, at 270, familial risk for one or more diseases is determined. For example, one or more metrics of familial risk for one or more diseases for the subject can be determined based at least on the family health history information of the subject.

At 280, combined assessment (e.g., based on the metrics of familial risk, family health history information, personal health history information, personal health behavior information, or some combination thereof) is performed. For example, one or more personalized disease prevention recommendations for the subject can be generated during the combined assessment. Risk scenarios can be consulted as described herein.

At 290, one or more disease prevention recommendations are presented. The disease prevention recommendations can be included as part of a disease prevention plan (e.g., a personalized disease prevention plan) as described herein. The recommendations and plan can be provided via the user interfaces described herein (e.g., in a single web-based session responsive to the information entered by the subject).

Example 6

Exemplary User Interface

In any of the examples herein, any number of user interfaces can be presented to a user for collecting information such as family health history information, personal health history information, personal health behavior information, or some combination thereof. For example, a software-presented user interface can include a set of forms that are presented (e.g., to a subject user) and completed (e.g., by the subject user) via a computerized device.

In any of the examples herein, forms can be presented via a networked device. For example, web pages can be presented via the HTTP protocol or some other technique. Access can be controlled via username and password techniques.

Example 7

Exemplary Risk Scenarios

In any of the examples described herein, information provided by a subject can be analyzed to determine whether the information falls within one or more risk scenarios. For example, any of the information in the family health history, familial risk of disease, personal health history, health behavior, or combination thereof can be used as criteria for determining whether the subject satisfies one or more risk scenarios.

In practice, such risk scenarios can be specified as a set of criteria that can be stored in data structures (e.g., in a table, database, or the like) on one or more computer-readable media. Such criteria can include whether a certain disease appears in the family health history, whether the subject is at risk (e.g., high risk, at least medium risk, and the like) for one or more diseases, whether the subject has ever had one or more diseases, whether the subject engages in certain health behaviors (e.g., engages or has engaged in one or more health-related personal practices, has had one or more screening tests performed), and the like.

Example 8

Exemplary Personalized Disease Prevention Recommendations

Based on whether a subject meets one or more risk scenarios, a set of one or more personalized disease prevention recommendations can be presented as part of a disease prevention plan for the subject (e.g., a personalized disease prevention plan). The personalized disease prevention recommendations can include information appearing in or derived from any of the information provided by the subject.

Recommendations can include recommendations to continue (e.g., affirm) or modify behaviors or conditions indicated in information collected from the subject. For example, recommendations can be directed to personal health history such as screening tests (e.g., "Schedule an appointment today.") or health-related personal practices (e.g., "Stop smoking now." "Continue to eat <number> servings of fruit a day." or "Increase your level of physical activity.").

Factors that led to the recommendation can be included in the recommendation. For example, one or more of the criteria for the risk scenario can be included. In practice, such factors can be expressed as a plain language (e.g., textual) description of the criteria (e.g., "Your Body Mass Index is over <number>, and at least one or your first degree relatives had <disease> therefore . . . ").

Example 9

Exemplary Method for Determining Familial Risk of One or More Diseases of Interest for a Subject FIG. 3 shows an exemplary method 300 for determining familial risk of one or more diseases of interest for a subject.

At 302, family health history of a subject is received. For example, disease history of a subject's first and second degree biological relatives including the number, lineage, and gender of first and second degree relatives, whether a relative has a disease of interest or an indicator disease, and the age of the relative at time of diagnosis of the disease of interest or indicator disease can be received.

At 304, a disease of interest is determined. For example, heart disease, stroke, diabetes, colorectal cancer, breast cancer, and ovarian cancer can be diseases of interest that are determined.

At 306, familial risk for a subject of the determined disease of interest can be assigned. For example, the family health history of a subject's first and second degree biological relatives can be analyzed to assign familial risk. Following the assignment of familial risk for the determined disease of interest, one or more additional diseases of interest can be determined at 304, and familial risk for the one or more additional diseases of interest can be assigned.

At 308, results of the assignment of familial risk for the one or more diseases of interest can be presented. For example, familial risk can be categorized as low (e.g., weak), moderate, or high (e.g., strong) and presented to the subject with accompanying familial risk clarifiers and recommendations for reducing the level of risk and/or recommended preventive medical strategies or exams (e.g., screenings).

Example 10

Figure 4:
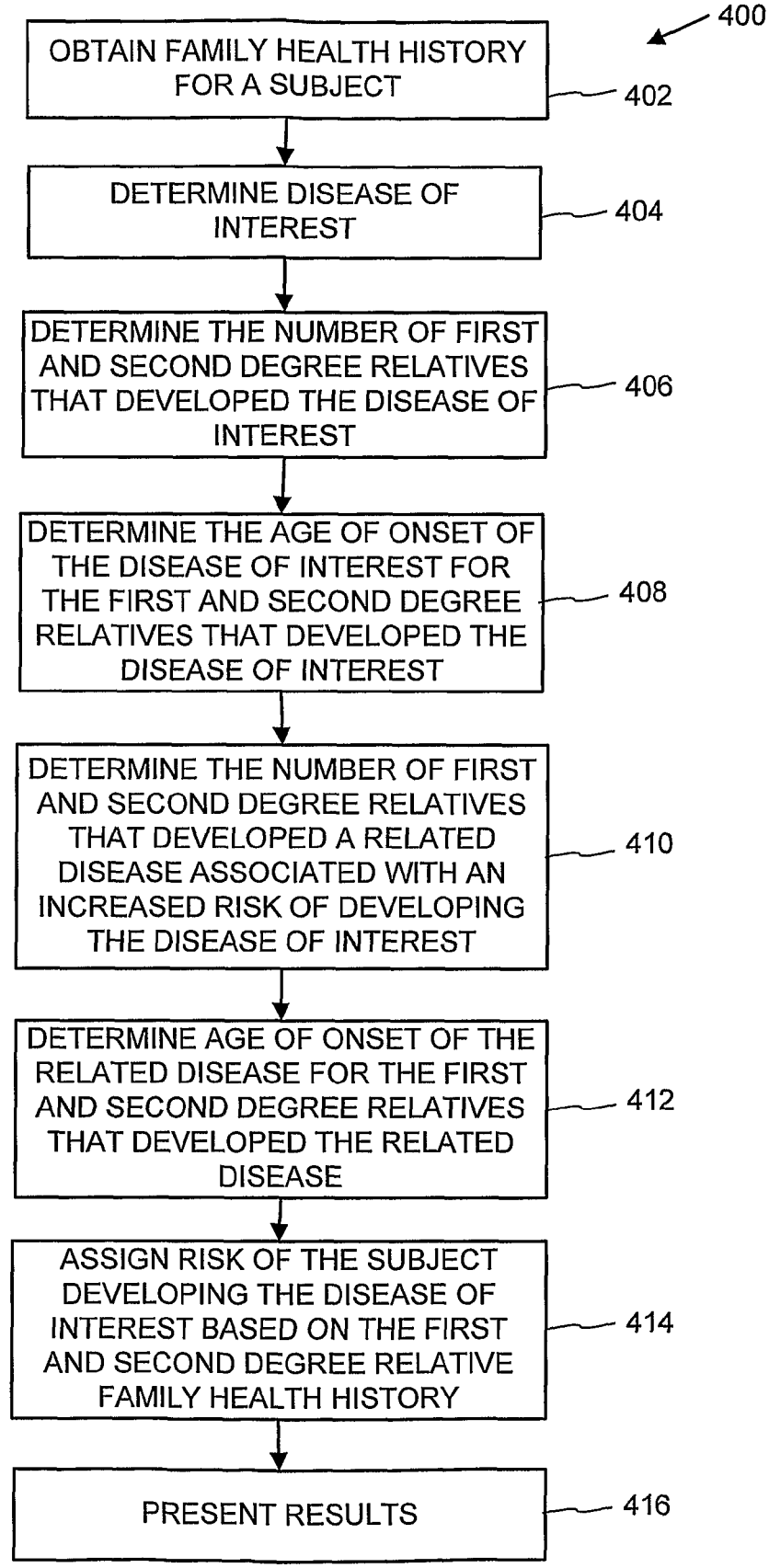
FIG. 4 is a flowchart showing an exemplary method for determining a subject's familial risk of a disease of interest based on first and second degree relative family health history.

Exemplary Method for Determining a Subject's Familial Risk of a Disease of Interest Based on First and Second Degree Relative Family Health History FIG. 4 shows an exemplary method 400 for determining a subject's familial risk of a disease of interest based on first and second degree relative family health history.

At 402, family health history for a subject is obtained. Family health history can be obtained via the subject, paper or electronic health records. For example, family health history for a subject can be obtained via questionnaires in an electronic or paper format.

At 404, a disease of interest is determined from the family health history. For example, heart disease, stroke, diabetes, colorectal cancer, breast cancer, and ovarian cancer can be diseases of interest that are determined.

In the example, the disease of interest is treated as an indicator disease. Accordingly, at 406, the number of first and second degree relatives that developed the disease of interest is determined from the family health history.

At 408, the age of onset of the disease of interest for the first and second degree relatives that developed the disease of interest is determined from the family health history. Lineage and gender of the first and second degree relatives that developed the disease of interest can also be determined.

At 410, the number of first and second degree relatives that developed a different disease associated with an increased risk of developing the disease of interest (e.g., a different indicator disease) is determined from the family health history.

At 412, the age of onset of the indicator disease for the first and second degree relatives that developed the different disease is determined from the family health history. Lineage and gender of the first and second degree relatives that developed the different disease can also be determined.

At 414, a subject's familial risk of the disease of interest based on the first and/or second degree relative family health history is assigned. For example, familial risk can be assigned as low (e.g., weak), moderate, or high (e.g., strong) based on the family health history (e.g., detection of predetermined familial disease history scenarios).

At 416, results of the assignment of familial risk for the one or more diseases of interest can be presented. For example, familial risk can be categorized as low (e.g., weak), moderate, or high (e.g., strong) and presented to the subject with accompanying familial risk clarifiers and recommendations for reducing the level of risk and/or recommended preventive medical strategies or exams (e.g., screenings).

Example 11

Figure 5:
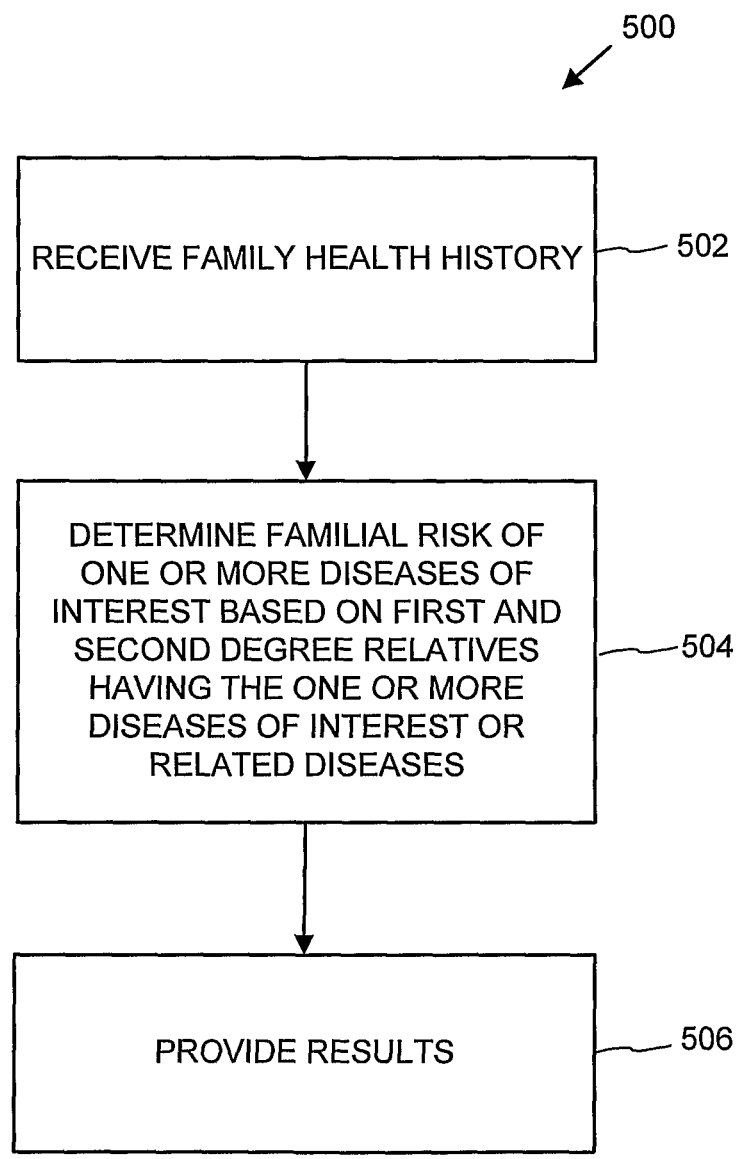
FIG. 5 is a flowchart showing an exemplary computer-implemented method for determining familial risk of one or more diseases of interest.

Exemplary Computer-Implemented Method for Determining Familial Risk of One or More Diseases of Interest FIG. 5 shows an exemplary computer-implemented method 500 for determining familial risk of one or more diseases of interest.

At 502, family health history is received. For example, disease history of a subject's first and second degree biological relatives including the number, gender, and lineage of first and second degree relatives, whether a relative has a disease of interest or an indicator disease, and the age of the relative at time of diagnosis of disease of interest or indicator disease can be received.

At 504, familial risk of one or more diseases of interest is determined based on first and/or second degree relatives having the one or more diseases of interest or indicator diseases.

At 506, results of the assignment of familial risk for the one or more diseases of interest can be presented. For example, familial risk can be categorized as low (e.g., weak), moderate, or high (e.g., strong) and presented with accompanying familial risk clarifiers and recommendations for reducing the level of risk and/or recommended preventive medical strategies or exams (e.g., screenings).

Example 12

Figure 6:
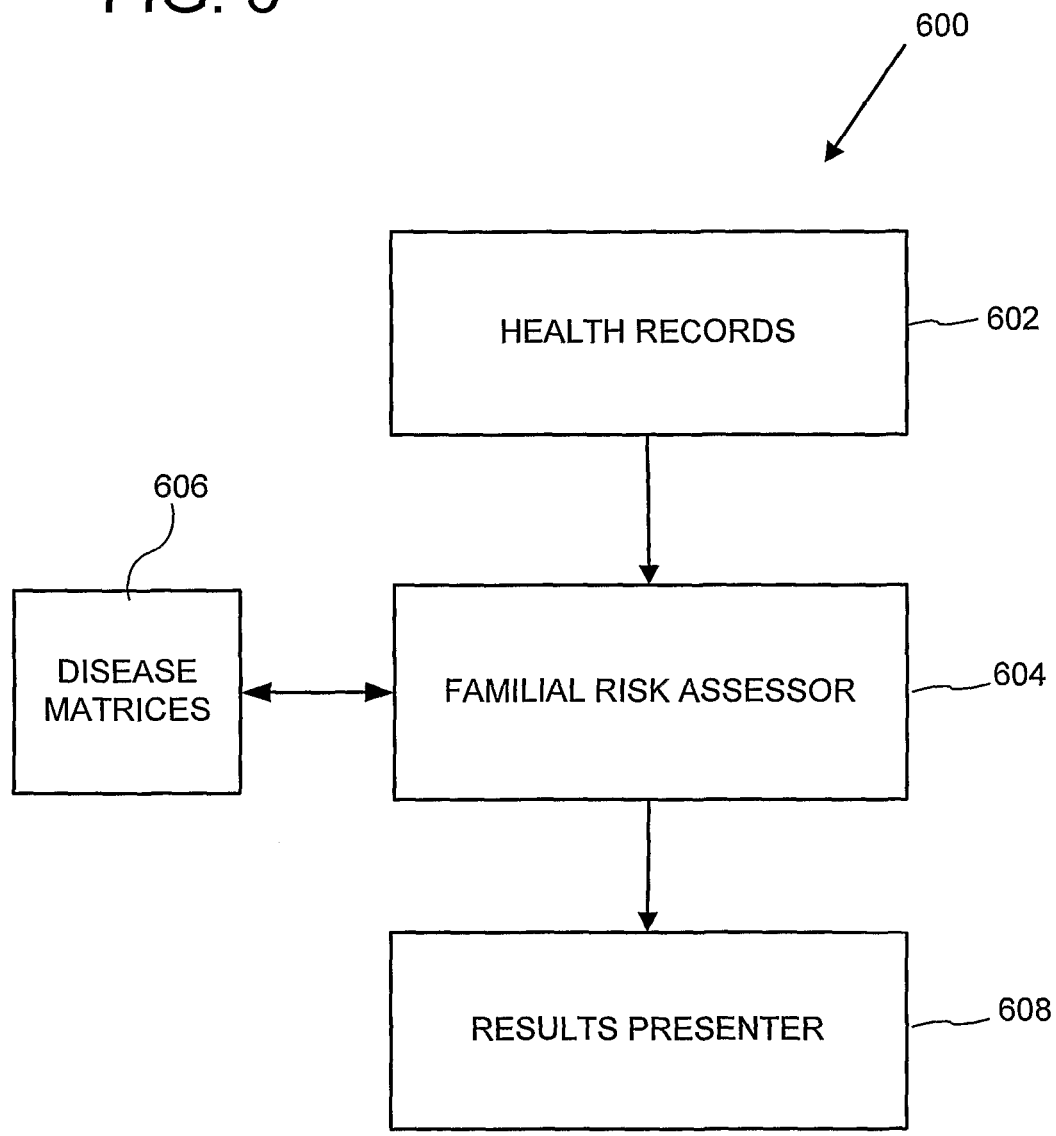
FIG. 6 is a block diagram showing another exemplary system for determining a disease prevention plan for a subject based on familial risk.

Exemplary System for Determining a Disease Prevention Plan for a Subject Based on Familial Risk FIG. 6 shows an exemplary system 600 for determining a disease prevention plan for a subject based on familial risk.

Health records 602 of a subject are obtained and input into a familial risk assessor 604 to assess the familial risk of one or more diseases.

The familial risk assessor 604 can employ one or more disease matrices 606 to determine familial risk of one or more diseases. For example, a disease matrix can include a two-dimensional table with various predetermined familial disease health scenarios on both the x axis and y axis. The intersection of two predetermined familial disease history scenarios in a disease matrix can result in a familial risk assessment being assigned based on the intersection of the two scenarios. Furthermore, familial risk clarifiers (e.g., qualifying statements which clarify or further explain the assignment of familial risk of disease based on the intersection of two predetermined familial disease history scenarios) can be incorporated into one or more disease matrix intersections.

Familial risk assessment, familial risk classifiers, and a disease prevention plan based on familial risk, personal health history information, and/or personal health behavior information can be presented as results by a results presenter 608.

A disease prevention plan can be determined for a subject as described in detail below.

Example 13

Figure 7:
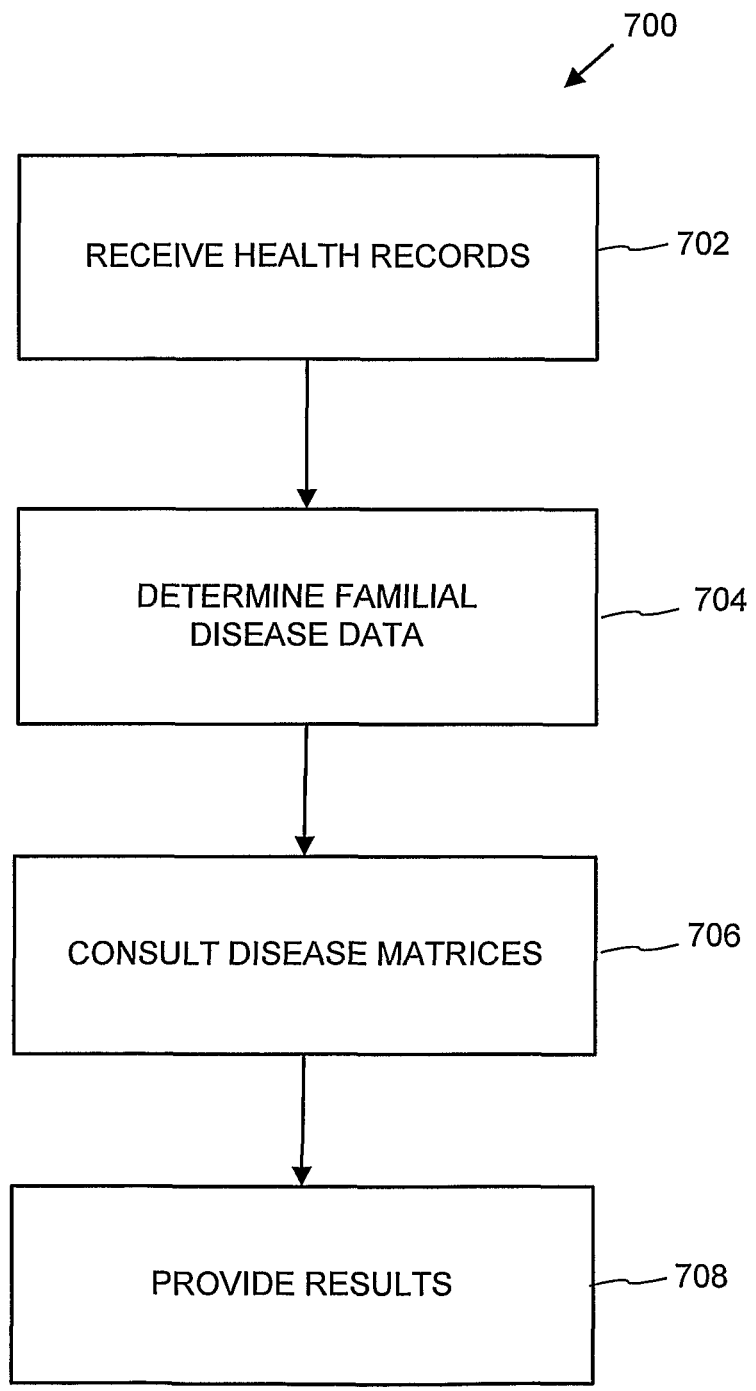
FIG. 7 is a flowchart showing yet another exemplary method for determining familial risk of disease for a subject.

Another Exemplary Method for Determining Familial Risk of Disease of a Subject FIG. 7 shows another method 700 for determining familial risk of disease of a subject. For example, system 600 can be implemented to perform method 700.

At 702, health records are received. For example, personal health history records and health records of one or more relatives can be received. The health records can include disease history of a subject's first and second degree biological relatives including the number, gender, and lineage of first and second degree relatives, whether a relative has a disease of interest or an indicator disease, and the age of the relative at time of diagnosis of disease of interest or indicator disease can be received. Additionally, health records can include personal health history information such as name, date of birth, gender, age, race/ethnicity, height, weight, whether a subject currently has any disease of interest or indicator disease, personal health behavior information, or any combination thereof. Personal health behavior information can include information related to smoking, exercise, diet, screening tests, and the like.

At 704, familial disease data can be determined from the health records received. For example, disease history of a subject's first and second degree biological relatives including the number, gender, and lineage of first and second degree relatives, whether a relative has an indictor disease, and the age of the relative at time of diagnosis of the indicator disease can be determined.

At 706, one or more familial risk matrices can be consulted to determine familial risk of disease of the subject based on determined familial disease data. For example, predetermined familial disease health scenarios (e.g., disease data on first and second degree relatives) can be compared to familial risk matrices (e.g., matrices that assign a categorization of familial risk of disease) to determine if an intersection of two predetermined familial disease history scenarios is present.

At 708, results of the consultation of the one or more familial risk matrices can be provided as results of the determination of familial risk of disease (e.g., as part of a disease prevention plan or to select a disease prevention plan). For example, an intersection of two predetermined familial disease history scenarios can result in a risk assessment being assigned. Additionally, familial risk clarifiers can be provided with the results to clarify or further explain the determination of familial risk of disease.

Example 14

Figure 8:
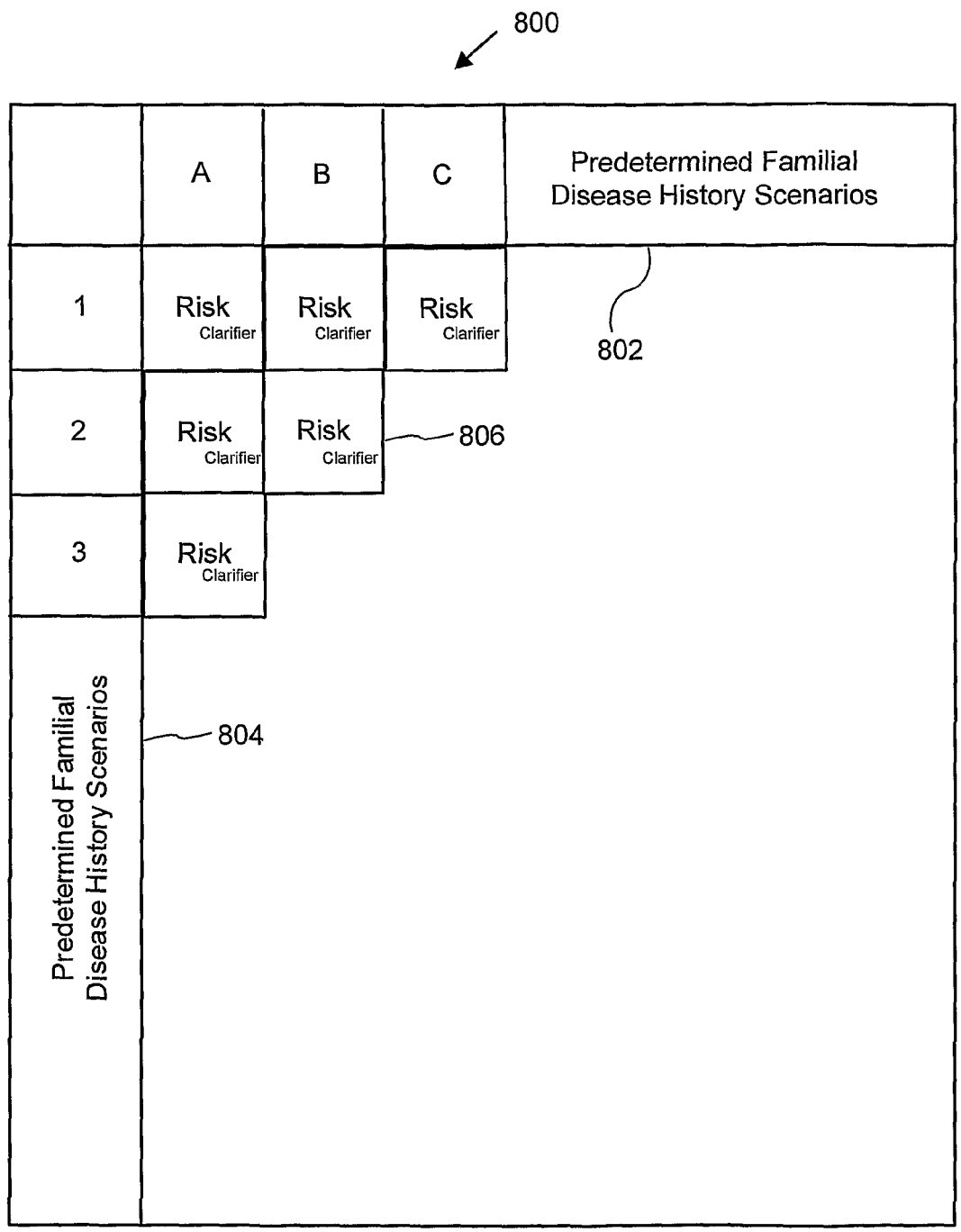
FIG. 8 illustrates an exemplary familial risk matrix for determining familial risk of disease based on family health history.

Exemplary Familial Risk Matrix for Determining Familial Risk of Disease Based on Family Health History FIG. 8 illustrates an exemplary familial risk matrix 800 for determining familial risk of disease based on family health history. Such a matrix can be used to assess a subject's risk of developing a disease of interest in any of the examples herein.

The x-axis of the matrix includes predetermined familial disease history scenarios 802 (e.g. A, B, C . . . ) and the y-axis of the matrix includes predetermined familial disease history scenarios 804 (e.g. 1, 2, 3 . . . ). For example, scenarios based on the number of first and second degree relatives from one lineage (e.g., nuclear, maternal or paternal) having a disease of interest or an indicator disease, the age of the relative at time of diagnosis of the disease of interest or the indicator disease, and the gender of the relative can be predetermined familial disease scenarios 802 and 804. In matrices in which breast cancer or ovarian cancer is the disease of interest, for example, Ashkenazi Jewish ancestry can also be a predetermined familial disease scenario.

The intersection of two predetermined familial disease history scenarios in a disease matrix results in a cell 806 which includes a risk assessment category (e.g. "Risk") being assigned based on the intersection of the two scenarios. Risk can be assigned one of three levels of risk for a disease represented by uppercase letters: low or weak familial risk (A), moderate familial risk (M), or strong or high familial risk (H). Furthermore, familial risk clarifiers (e.g. "Clarifiers") can be included with the assignment of risk, thereby incorporating references to qualifying statements which clarify or further explain the assignment of familial risk of disease based on the intersection of two predetermined familial disease history scenarios (e.g., based on a familial or hereditary syndrome). Such familial risk clarifiers can be represented by lower case letter in the matrix and the references incorporated into the providing and presentation of results. Such familial risk clarifiers can be provided according to a general or disease-specific hierarchy as described in detail below.

Analysis of multiple intersections of two predetermined familial disease history scenarios can result in an overall familial risk level determination for the disease of interest. For example, the highest risk level determined can be selected as the overall familial risk level determination for the disease of interest.

Familial risk matrices for select diseases of interest are described in detail below.

Example 15

Exemplary Familial Risk Matrices for Determining Familial Risk of Breast Cancer Based on Family Health History FIGS. 9-11 illustrate exemplary familial risk matrices 900, 1000, and 1100 (according to the form of exemplary familial risk matrix 800) for determining familial risk of breast cancer based on family health history. Shaded areas of the matrices are duplicative cells within each matrix.

In the example, the definition of age of onset of breast cancer is defined as:

Breast cancer: early <age 50; late > or =age 50

There are up to six familial/hereditary syndromes that feature breast cancer. A listing of single gene disorders that feature breast cancer can be found in: Scheuner M T, Yoon P, Khoury M J. "Contribution of mendelian disorders to chronic disease: opportunities for recognition, intervention, and prevention." Am J Med Genet 2004; 125C:50-65, hereby incorporated by reference herein. The two most common forms are hereditary breast-ovarian cancer (HBOC) and hereditary site-specific breast cancer. Both are associated with germline BRCA1 and BRCA2 mutations. Most families with HBOC have BRCA mutations, and about half of families with hereditary site-specific breast cancer have BRCA mutations. The breast cancer familial risk matrices 900, 1000, and 1100 recognize familial characteristics that are associated with an increased risk of breast cancer, as well as the two common familial syndromes that feature breast cancer. Pattern recognition for families with HBOC/BRCA gene mutations is based on the NCCN Practice Guidelines in Oncology—v. 1.2004.

One of three levels of familial risk for a disease is assigned. The three levels of familial risk can be represented by uppercase letters: low or weak familial risk (A), moderate familial risk (M), or strong or high familial risk (H)

Familial risk clarifiers for the breast cancer matrices 900, 1000, and 1100 include:

a=At least one family member with both breast and ovarian cancer. The combination of these cancers is a risk factor for breast cancer and can be a sign of an inherited form of breast cancer called hereditary breast-ovarian cancer.

b=Closely related family members with breast and ovarian cancer. The combination of these two cancers is a risk factor for breast cancer and can be a sign of an inherited form of breast cancer called hereditary breast-ovarian cancer.

c=Two or more closely related family members with ovarian cancer. Although a different cancer, a family history of ovarian cancer is a risk factor for breast cancer and can be a sign of an inherited form of breast cancer called hereditary breast-ovarian cancer.

d=At least one family member with male breast cancer, which can be a sign of an inherited form of breast cancer.

e=At least one family member with breast cancer at a young age.

f=Two or more closely related family members with breast cancer.

g=A family member with breast cancer at a later age.

h=A family member with ovarian cancer, which can be a risk factor for breast cancer.

i=Three or more closely related family members with breast cancer.

j=Some inherited forms of breast and ovarian cancer are more common in Ashkenazi Jewish families, and this is noted if personal health information collected included ethnicity.

Example 16

Exemplary Hierarchy of Presentation of Familial Risk Clarifiers in Familial Risk Matrices for Determining Familial Risk of Breast Cancer Based on Family Health History Familial risk clarifiers in familial risk matrices for determining familial risk of breast cancer (according to example 10) based on family health history can be provided according to a hierarchy. For example, a hierarchy utilizing familial risk clarifiers described in example 10 can be as follows:

Familial risk clarifier "a" can be presented;
Familial risk clarifier "b" can be presented;
Familial risk clarifier "c" can be presented;
Familial risk clarifier "d" can be presented;
Familial risk clarifier "e" can be presented;
Familial risk clarifier "f" can be presented when familial risk clarifier "i" is not presented;
Familial risk clarifier "g" can be presented if:
Familial risk clarifier "a" is not presented; or Familial risk clarifier "b" is not presented; or Familial risk clarifier "d" is not presented; or Familial risk clarifier "e" is not presented; or Familial risk clarifier "f" is not presented; or Familial risk clarifier "i" is not presented;
Familial risk clarifier "h can be presented if:
Familial risk clarifier "a" is not presented; or Familial risk clarifier "b" is not presented;
or Familial risk clarifier "c" is not presented;
Familial risk clarifier "i" can be presented; and
Familial risk clarifier "j" can be presented.

Example 17

Exemplary Familial Risk Matrices for Determining Familial Risk of Ovarian Cancer Based on Family Health History FIGS. 12-17 illustrate exemplary familial risk matrices 1200, 1300, 1400, 1500, 1600, and 1700 (according to the form of exemplary familial risk matrix 800) for determining familial risk of ovarian cancer based on family health history. Shaded areas of the matrices are duplicative cells within each matrix.

In the example, the definition of age of onset of breast cancer is defined as:
Breast cancer: early <age 50; late > or =age 50.

In the example, the definition of early age of onset of colon cancer is defined as:
Colon cancer: early <age 50; late > or =age 50.

There are several familial/hereditary syndromes that feature ovarian cancer, including hereditary site-specific ovarian cancer, hereditary breast-ovarian cancer (HBOC) and hereditary nonpolyposis colon cancer (HNPCC). A listing of single gene disorders that feature ovarian cancer can be found in: Scheuner M T, Yoon P, Khoury M J. "Contribution of mendelian disorders to common chronic disease: opportunities for recognition, intervention and prevention." Am J Med Genet 2004; 125C:50-65. Hereditary breast-ovarian cancer (HBOC) is associated with germline BRCA1 and BRCA2 mutations, and most families with HBOC have BRCA mutations. HNPCC is associated with germline mutations in mismatch repair genes (most commonly MSH2 and MLH1). The ovarian cancer familial risk matrices 1200, 1300, 1400, 1500, 1600, and 1700 recognize familial characteristics that are associated with an increased risk of ovarian cancer, as well as the common familial syndromes that feature ovarian cancer. Pattern recognition for families with HBOC/BRCA gene mutations was based on the NCCN Practice Guidelines in Oncology—v. 1.2004. Pattern recognition for families with HNPCC is based on the Amsterdam Criteria and the Revised Bethesda Guidelines.

One of three levels of familial risk for a disease is assigned. The three levels of risk for a disease can be represented by uppercase letters: low or weak familial risk (A), moderate familial risk (M), or strong or high familial risk (H).

Familial risk clarifiers for the ovarian cancer familial risk matrices 1200, 1300, 1400, 1500, 1600, and 1700 include:

a≤At least one family member with ovarian, breast, and colon cancer. The combination of these cancers can be a sign of an inherited form of ovarian cancer—either hereditary breast-ovarian cancer or hereditary nonpolyposis colon cancer.

b=At least one family member with both ovarian and breast cancer. The combination of these cancers is a risk factor for ovarian cancer and can be a sign of an inherited form of ovarian cancer called hereditary breast-ovarian cancer.

c=At least one family member with both ovarian and colon cancer. The combination of these cancers can be a sign of an inherited form of ovarian cancer called hereditary nonpolyposis colon cancer.

e=Closely related family members with both ovarian and breast cancer. The combination of these cancers is a risk factor for ovarian cancer and can be a sign of an inherited form of ovarian cancer called hereditary breast-ovarian cancer.

f=Closely related family members with both ovarian and colon cancer. The combination of these cancers can be a sign of an inherited form of ovarian cancer called hereditary nonpolyposis colon cancer.

g=Two or more close family members with ovarian cancer.

h=A family member with ovarian cancer.

i=At least one family member with breast cancer at a young age. Although a different cancer, early-onset breast cancer can be a risk factor for ovarian cancer and can be a sign of an inherited form of ovarian cancer called hereditary breast-ovarian cancer.

j=Two or more closely related family members with breast cancer. Although a different cancer, breast cancer can be a risk factor for ovarian cancer and can be a sign of an inherited form of ovarian cancer called hereditary breast-ovarian cancer.

k=Three or more closely related family members with breast cancer. Although a different cancer, breast cancer can be a risk factor for ovarian cancer and can be a sign of an inherited form of ovarian cancer called hereditary breast-ovarian cancer.

l=At least one male family member with breast cancer, which can be a sign of an inherited form of ovarian cancer called hereditary breast-ovarian cancer.

m=At least one family member with colon cancer at a young age. Early-onset colon cancer can be a sign of an inherited form of ovarian cancer called hereditary nonpolyposis colon cancer.

n=Two or more closely related family members with colon cancer. Although a different cancer, a family history of colon cancer can be a sign of an inherited form of ovarian cancer called hereditary nonpolyposis colon cancer.

o=Some inherited forms of breast and ovarian cancer are more common in Ashkenazi Jewish families, and this is noted if personal health information collected included ethnicity.

Example 18

Exemplary Hierarchy of Presentation of Familial Risk Clarifiers in Familial Risk Matrices for Determining Familial Risk of Ovarian Cancer Based on Family Health History Familial risk clarifiers in familial risk matrices for determining familial risk of ovarian cancer (according to example 12) based on family health history can be provided according to a hierarchy. For example, a hierarchy utilizing familial risk clarifiers described in example 12 can be as follows:
Familial risk clarifier "a" can be presented;
Familial risk clarifier "b" can be presented;
Familial risk clarifier "c" can be presented;
Familial risk clarifier "e" can be presented;
Familial risk clarifier "f" can be presented;
Familial risk clarifier "g" can be presented;
Familial risk clarifier "i" can be presented;
Familial risk clarifier "j" can be presented if familial risk clarifier "k" is not presented;
Familial risk clarifier "k" can be presented;
Familial risk clarifier "l" can be presented;
Familial risk clarifier "m" can be presented;
Familial risk clarifier "n" can be presented; and
Familial risk clarifier "o" can be presented.

Example 19

Figure 20:
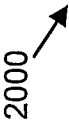

Exemplary Familial Risk Matrices for Determining Familial Risk of Colon Cancer Based on Family Health History FIGS. 18-20 illustrate exemplary familial risk matrices 1800, 1900, and 2000 (according to the form of exemplary familial risk matrix 800) for determining familial risk of colon cancer based on family health history. Shaded areas of the matrices are duplicative cells within each matrix.

In the example, the definition of age of onset of colon cancer is defined as:

Colon cancer: early <age 50; late > or =age 50.

There are several familial/hereditary syndromes that feature colon cancer, including polyposis and nonpolyposis syndromes. A listing of single gene disorders that feature colon cancer can be found in: Scheuner M T, Yoon P, Khoury M J. "Contribution of mendelian disorders to common chronic disease: opportunities for recognition, intervention and prevention." Am J Med Genet 2004; 125C:50-65. The most common familial syndrome is hereditary nonpolyposis colon cancer (HNPCC), which is associated with germline mutations in mismatch repair genes (most commonly MSH2 and MLH1). These matrices recognize familial characteristics that are associated with an increased risk of colon cancer, as well as HNPCC. Pattern recognition for families with HNPCC is based on the Amsterdam Criteria and the Revised Bethesda Guidelines.

One of three levels of familial risk for a disease is assigned. The three levels of risk for a disease can be represented by uppercase letters: low or weak familial risk (A), moderate familial risk (M), or strong or high familial risk (H).

Familial risk clarifiers for the colon cancer familial risk matrices 1800, 1900, and 2000 include:

a=At least one family member with both colon and ovarian cancer. The combination of these cancers can be a sign of an inherited form of colon cancer called hereditary nonpolyposis colon cancer.
b=Closely related family members with colon and ovarian cancer. The combination of these cancers can be a sign of an inherited form of colon cancer called hereditary nonpolyposis colon cancer.
c=At least one family member with colon cancer at a young age.
d=Two or more closely related family members with colon cancer.
e=Three or more closely related family members with colon cancer.
f=Two or more closely related family members with ovarian cancer. Although a different cancer, a family history of ovarian cancer can be a sign of an inherited form of colon cancer called hereditary nonpolyposis colon cancer.
g=A family member with colon cancer.

Example 20

Exemplary Hierarchy of Presentation of Familial Risk Clarifiers in Familial Risk Matrices for Determining Familial Risk of Colon Cancer Based on Family Health History Familial risk clarifiers in familial risk matrices for determining familial risk of colon cancer (according to example 14) based on family health history can be provided according to a hierarchy.

For example, a hierarchy utilizing familial risk clarifiers described in example 14 can be as follows:

For example, a hierarchy can be as follows:
Familial risk clarifier "a" can be presented;
Familial risk clarifier "b" can be presented;
Familial risk clarifier "c" can be presented;
Familial risk clarifier "d" can be presented if familial risk clarifier "e" is not presented;
Familial risk clarifier "e" can be presented;
Familial risk clarifier "f" can be presented; and
Familial risk clarifier "g" can be presented if:
Familial risk clarifier "a" is not presented; or Familial risk clarifier "b" is not presented;
or Familial risk clarifier "c" is not presented; or Familial risk clarifier "d" is not presented; or Familial risk clarifier "e" is not presented.

Example 21

Exemplary Familial Risk Matrices for Determining Familial Risk of Coronary Heart Disease Based on Family Health History FIGS. 21-26 illustrate exemplary familial risk matrices 2100, 2200, 2300, 2400, 2500, and 2600 (according to the form of exemplary familial risk matrix 800) for determining familial risk of coronary heart disease based on family health history. Shaded areas of the matrices are duplicative cells within each matrix.

In the example, the definition of age of onset of coronary heart disease is defined as:

Coronary heart disease: Men, early <age 55; late > or =age 55.

Women, early <age 65; late > or =age 65.

In the example, the definition of age of onset of stroke is defined as:

Stroke: early <age 60; late > or =age 60.

In the example, the definition of age of onset of diabetes is defined as:

Diabetes: Early (type 1)<age 20; late (Type 2)> or =age 20.

Familial "syndromes" or phenotypes that feature coronary heart disease (CHD) include: Metabolic syndrome which can feature CHD, type 2 diabetes (DM) and stroke (CVA); CHD and stroke; and CHD-specific families.

A listing of single gene disorders that feature coronary heart disease or myocardial infarction can be found in: Scheuner M T, Yoon P, Khoury M J. "Contribution of mendelian disorders to common chronic disease: opportunities for recognition, intervention and prevention." Am J Med Genet 2004; 125C:50-65. Definitions of metabolic syndrome have been proposed by three national organizations: 1) NCEP ATPIII, 2) WHO (World Health Organization) and the 3) American Association of Clinical Endocrinologists (AACE). Although the metabolic syndrome is a familial disease and genetic factors are associated with the phenotype, only the AACE considers family history of type 2 diabetes, hypertension or cardiovascular disease in their definition. For a review of the definitions see Grundy S M, Brewer H B, Cleeman J I, Smith S C, Lenfant C et al., "Definition of the metabolic syndrome." Report of the National Heart, Lung, and Blood Institute/American Heart Association Conference on Scientific Issues Related to Definition. Circulation 2004; 109:433-438, hereby incorporated herein by reference.

One of three levels of familial risk for a disease is assigned. The three levels of risk for a disease can be represented by uppercase letters: low or weak familial risk (A), moderate familial risk (M), or strong or high familial risk (H).

Familial risk clarifiers for the coronary heart disease familial risk matrices 2100, 2200, 2300, 2400, 2500, and 2600 include:

a=At least one family member with coronary heart disease, diabetes and stroke. The combination of these conditions can be a sign of the metabolic syndrome.
b=At least one family member with coronary heart disease and diabetes. The combination of these conditions can be a sign of the metabolic syndrome.
c=At least one family member with coronary heart disease and stroke. The combination of these conditions is a risk factor for coronary heart disease.

d=At least one family member with stroke and diabetes. The combination of these conditions can be a sign of the metabolic syndrome.

e=Closely related family members with coronary heart disease and diabetes. The combination of these conditions can be a sign of the metabolic syndrome.

f=Closely related family members with coronary heart disease and stroke. The combination of these conditions is a risk factor for coronary heart disease.

g=Closely related family members with stroke and diabetes. The combination of these conditions can be a sign of the metabolic syndrome.

h=At least one family member with coronary heart disease at a young age. Early-onset disease is a sign of a greater number of cardiovascular risk factors.

i=Two or more closely related family members with coronary heart disease.

j=Three or more closely related family members with coronary heart disease.

k=Two or more closely related family members with diabetes, which can be a sign of the metabolic syndrome.

l=A family member with diabetes, which can be a sign of the metabolic syndrome.

m=At least one family member with stroke at a young age. Stroke and coronary heart disease share many risk factors. Early-onset disease is a sign of a greater number of cardiovascular risk factors.

n=Two or more closely related family members with stroke. Stroke and coronary heart disease share many risk factors.

o=A family member with coronary heart disease.

p=Closely related family members with coronary heart disease, diabetes and stroke. The combination of these conditions can be a sign of the metabolic syndrome.

Example 22

Exemplary Hierarchy of Presentation of Familial Risk Clarifiers in Familial Risk Matrices for Determining Familial Risk of Coronary Heart Disease Based on Family Health History Familial risk clarifiers in familial risk matrices for determining familial risk of coronary heart disease (according to example 16) based on family health history can be provided according to a hierarchy. For example, a hierarchy utilizing familial risk clarifiers described in example 16 can be as follows:

Familial risk clarifier "a" can be presented;
Familial risk clarifier "b" can be presented;
Familial risk clarifier "c" can be presented;
Familial risk clarifier "d" can be presented if familial risk clarifier "e" is not presented;
Familial risk clarifier "e" can be presented if familial risk clarifier "p" is not presented;
Familial risk clarifier "f" can be presented if familial risk clarifier "p" is not presented;
Familial risk clarifier "g" can be presented if familial risk clarifier "p" is not presented;
Familial risk clarifier "h" can be presented;
Familial risk clarifier "i" can be presented if familial risk clarifier "j" is not presented;
Familial risk clarifier "j" can be presented;
Familial risk clarifier "k" can be presented;
Familial risk clarifier "l" can be presented if:
Familial risk clarifier "a" is not presented; or Familial risk clarifier "b" is not presented;
or Familial risk clarifier "d" is not presented; or Familial risk clarifier "e" is not presented; or Familial risk clarifier "g" is not presented; or Familial risk clarifier "k" is not presented; or Familial risk clarifier "p" is not presented;
Familial risk clarifier "m" can be presented;
Familial risk clarifier "n" can be presented;
Familial risk clarifier "o" can be presented if:
Familial risk clarifier "a" is not presented; or Familial risk clarifier "b" is not presented;
or Familial risk clarifier "c" is not presented; or Familial risk clarifier "e" is not presented; or Familial risk clarifier "f" is not presented; or Familial risk clarifier "h" is not presented; or Familial risk clarifier "i" is not presented; or Familial risk clarifier "j" is not presented; or Familial risk clarifier "p" is not presented; and
Familial risk clarifier "p" can be presented if:
Familial risk clarifier "a" is not presented; or Familial risk clarifiers "b" and "d" are not presented.

Example 23

Exemplary Familial Risk Matrices for Determining Familial Risk of Stroke Based on Family Health History FIGS. 27-32 illustrate exemplary familial risk matrices 2700, 2800, 2900, 3000, 3100, and 3200 (according to the form of exemplary familial risk matrix 800) for determining familial risk of stroke based on family health history. Shaded areas of the matrices are duplicative cells within each matrix.

In the example, the definition of age of onset of stroke is defined as:

Stroke: early <age 60; late > or =age 60.

In the example, the definition of age of onset of coronary heart disease is defined as:

Coronary heart disease: Men, early <age 55; late > or =age 55.

Women, early <age 65; late > or =age 65.

In the example, the definition of age of onset of diabetes is defined as:

Diabetes: Early (type 1)<age 20; late (Type 2)> or =age 20.

Familial "syndromes" or phenotypes that feature stroke (CVA) include:

Metabolic syndrome which can feature CHD, type 2 diabetes (DM) and stroke (CVA);

Stroke and CHD; and

Stroke-specific families

A listing of single gene disorders that feature stroke can be found in: Scheuner M T, Yoon P, Khoury M J. "Contribution of mendelian disorders to common chronic disease: opportunities for recognition, intervention and prevention." Am J Med Genet 2004; 125C:50-65. Definitions of metabolic syndrome have been proposed by three national organizations: 1) NCEP ATPIII, 2) WHO and the 3) American Association of Clinical Endocrinologists (AACE). Although the metabolic syndrome is a familial disease and genetic factors are associated with the phenotype, only the AACE considers family history of type 2 diabetes, hypertension or cardiovascular disease in their definition. For a review of the definitions see Grundy S M, Brewer H B, Cleeman J I, Smith S C, Lenfant C et al., "Definition of the metabolic syndrome." Report of the National Heart, Lung, and Blood Institute/American Heart Association Conference on Scientific Issues Related to Definition. Circulation 2004; 109:433-438.

One of three levels of familial risk for a disease is assigned. The three levels of risk for a disease can be represented by uppercase letters: low or weak familial risk (A), moderate familial risk (M), or strong or high familial risk (H).

Familial risk clarifiers for the stroke familial risk matrices 2700, 2800, 2900, 3000, 3100, and 3200 include:

a=At least one family member with stroke, coronary heart disease and diabetes. The combination of these conditions can be a sign of the metabolic syndrome.

b=At least one family member with stroke and diabetes. The combination of these conditions can be a sign of the metabolic syndrome.

c=At least one family member with stroke and coronary heart disease. The combination of these conditions is a risk factor for stroke.

d=At least one family member with coronary heart disease and diabetes. The combination of these conditions can be a sign of the metabolic syndrome.

e=Closely related family members with stroke and diabetes. The combination of these conditions can be a sign of the metabolic syndrome.

f=Closely related family members with stroke and coronary heart disease. The combination of these conditions is a risk factor for stroke.

g=Closely related family members with coronary heart disease and diabetes. The combination of these conditions can be a sign of the metabolic syndrome.

h=At least one family member with stroke at a young age. Early-onset disease is a sign of a greater number of cardiovascular risk factors.

i=Two or more closely related family members with stroke.

j=Three or more closely related family members with stroke.

k=Two or more closely related family members with coronary heart disease. Although a different type of disease, coronary heart disease is a risk factor for stroke.

l=At least one family member with coronary heart disease at a young age. Although a different disease, coronary heart disease is a risk factor for stroke. Early-onset disease is a sign of a greater number of cardiovascular risk factors.

m=A family member with coronary heart disease. Although a different disease, coronary heart disease is a risk factor for stroke.

n=Two or more closely related family members with diabetes, which can be a sign of the metabolic syndrome.

o=A family member with stroke.

p=Closely related family members with stroke, coronary heart disease and diabetes. The combination of these conditions can be a sign of the metabolic syndrome.

Example 24

Exemplary Hierarchy of Presentation of Familial Risk Clarifiers in Familial Risk Matrices for Determining Familial Risk of Coronary Heart Disease Based on Family Health History Familial risk clarifiers in familial risk matrices for determining familial risk of coronary heart disease (according to example 18) based on family health history can be provided according to a hierarchy. For example, a hierarchy utilizing familial risk clarifiers described in example 18 can be as follows:

Familial risk clarifier "a" can be presented;
Familial risk clarifier "b" can be presented;
Familial risk clarifier "c" can be presented;
Familial risk clarifier "d" can be presented;
Familial risk clarifier "e" can be presented if familial risk clarifier "p" is not presented;
Familial risk clarifier "f" can be presented if familial risk clarifier "p" is not presented;
Familial risk clarifier "g" can be presented if familial risk clarifier "p" is not presented;
Familial risk clarifier "h" can be presented;
Familial risk clarifier "i" can be presented if familial risk clarifier "j" is not presented;
Familial risk clarifier "j" can be presented;
Familial risk clarifier "k" can be presented;
Familial risk clarifier "l" can be presented;
Familial risk clarifier "m" can be presented if:
Familial risk clarifier "a" is not presented; or Familial risk clarifier "c" is not presented;
or Familial risk clarifier "d" is not presented; or Familial risk clarifier "f" is not presented; or Familial risk clarifier "g" is not presented; or Familial risk clarifier "k" is not presented; or Familial risk clarifier "l" is not presented; or Familial risk clarifier "p" is not presented;
Familial risk clarifier "p" can be presented if:
Familial risk clarifier "a" is not presented; or Familial risk clarifiers "b" and "d" are not presented.

Example 25

Exemplary Familial Risk Matrices for Determining Familial Risk of Type 2 Diabetes Based on Family Health History FIGS. 33-35 illustrate exemplary familial risk matrices 3300, 3400, and 3500, (according to the form of exemplary familial risk matrix 800) for determining familial risk of type 2 diabetes based on family health history. Shaded areas of the matrices are duplicative cells within each matrix.

In the example, the definition of age of onset of diabetes is defined as:

Diabetes: Early (type 1)<age 20; late (Type 2)> or =age 20.

Type 2 diabetes aggregates in families, and family history of type 2 diabetes is a significant risk factor for type 2 diabetes. Type 1 diabetes (usually diagnosed before age 20) is an autoimmune disorder. Type 1 diabetes typically does not aggregate in families and thus family history is not a significant risk factor for this disorder. Additionally, a history of type 1 diabetes is not a significant risk factor for type 2 diabetes. Therefore, when assessing familial risk for type 2 diabetes, the familial risk matrices only consider diabetes diagnosed at or after age 20.

These algorithms within the familial risk matrices 3300, 3400, and 3500 are designed to assess familial risk of type 2 diabetes (also known as adult-onset diabetes and non-insulin dependent diabetes). Type 2 diabetes accounts for more then 90% of all diabetes in adults. Most type 2 diabetes is due to insulin resistance and these patients are at high risk for the conditions associated with the metabolic syndrome (e.g., diabetes, coronary heart disease, stroke, hypertension and dyslipidemia).

A listing of single gene disorders that feature diabetes can be found in: Scheuner M T, Yoon P, Khoury M J. "Contribution of mendelian disorders to common chronic disease: opportunities for recognition, intervention and prevention." Am J Med Genet 2004; 125C:50-65.

One of three levels of familial risk for a disease is assigned. The three levels of risk for a disease can be represented by uppercase letters: low or weak familial risk (A), moderate familial risk (M), or strong or high familial risk (H).

Familial risk clarifiers for the type 2 diabetes familial risk matrices 3300, 3400, and 3500 include:

a=Three or more closely related family members with adult-onset diabetes.
b=Two or more closely related family members with adult-onset diabetes.
c=A family member with adult-onset diabetes.

Example 26

Exemplary Hierarchy of Presentation of Familial Risk Clarifiers in Familial Risk Matrices for Determining Familial Risk of Type 2 Diabetes Based on Family Health History Familial risk clarifiers in familial risk matrices for determining familial risk of diabetes (according to example 20) based on family health history can be provided according to a hierarchy. For example, a hierarchy utilizing familial risk clarifiers described in example 20 can be as follows:

Familial risk clarifier "a" can be presented;
Familial risk clarifier "b" can be presented if familial risk clarifier a is not presented;
Familial risk clarifier "c" can be presented if:
Familial risk clarifier "a" is not presented; or Familial risk clarifier "b" is not presented.

Example 27

Exemplary System for Determining a Disease Prevention Plan

Figure 36:
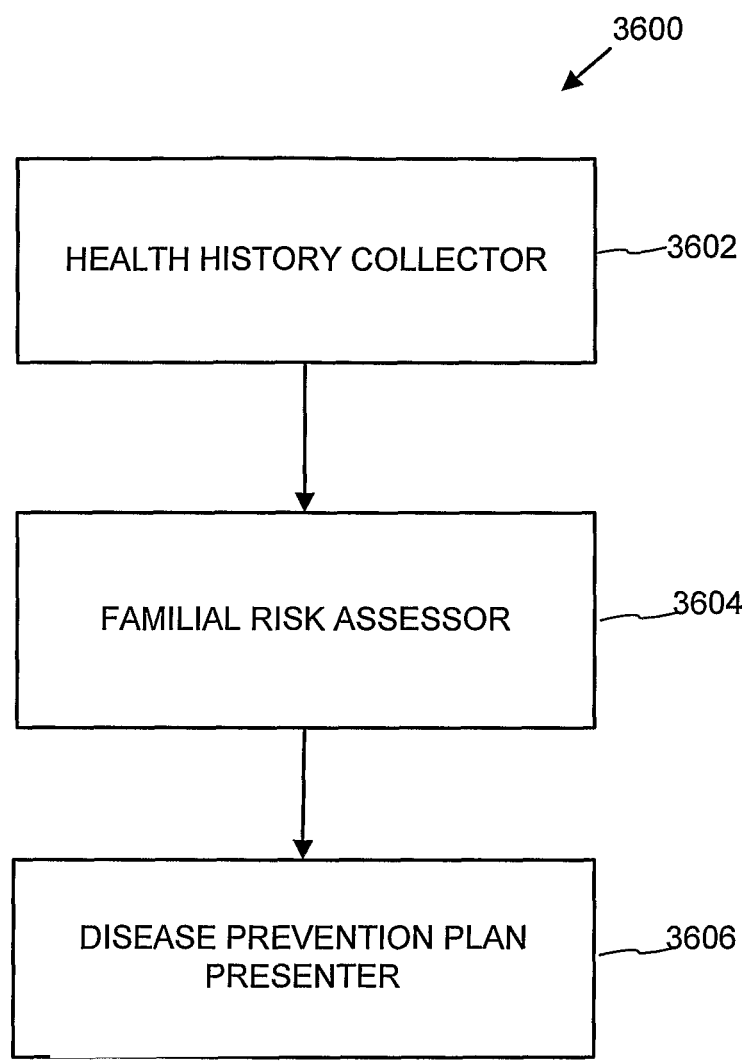
FIG. 36 is a block diagram showing an exemplary system for determining a disease prevention plan.

FIG. 36 shows an exemplary system 3600 for determining a disease prevention plan.

Health history collector 3602 can collect health history information and input the information into a familial risk assessor 3604 to assess the familial risk of one or more diseases. For example, electronic or paper-based questionnaires can be health history collectors and familial risk matrices (as described in the above examples) can be familial risk assessors. The familial risk assessor 3604 can employ any of the methods described above.

A disease prevention plan presenter 3606 can receive information from the health history information (e.g., demographic information, health history information, behavior information, participation in screening tests, and the like) and familial risk assessor and present a disease prevention plan. An electronic or paper-based report can be a disease prevention plan presenter. Such reports can include familial disease risk, familial risk clarifiers, pedigree presentation (e.g., a family tree display indicating disease in family members) and recommendations for screening tests, behavioral recommendations (e.g., changes or affirmations), and the like. Exemplary health collectors and disease prevention plan reports are shown in the examples below.

Example 28

Exemplary Risk Scenarios

In any of the examples herein, risk scenarios can be developed based on familial risk (e.g., as assessed by the disease matrices described above) and personal health history information collected. Recommendations can be made based on exemplary risk scenarios to be included as part of a personalized disease prevention plan for a subject.

Example 29

Exemplary Breast Cancer Disease Prevention Recommendations

An exemplary disease prevention plan (e.g., for use with system 3600) based on breast cancer familial risk assessment and screening questions is shown below. Screening questions can include the following questions:

1) A clinical breast exam is when a doctor or other health professional examines your breasts and feels for lumps and other changes. Have you had a clinical breast exam?
_____ Never
_____ Yes, within the past year
_____ Yes, 1 to 2 years ago
_____ Yes, 3 to 5 years ago
_____ Yes, 6 to 10 years ago
_____ Yes, more than 10 years ago
_____ Don't know/Not sure 2) A mammogram is an x-ray of each breast to look for early signs of breast cancer. Have you had a mammogram?
_____ Never
_____ Yes, within the past year
_____ Yes, 1 to 2 years ago
_____ Yes, 3 to 5 years ago
_____ Yes, 6 to 10 years ago
_____ Yes, more than 10 years ago
_____ Don't know/Not sure The following risk scenarios are examples of exemplary disease prevention plan recommendations based on answers to the above questions and familial risk assessment. The following six risk scenarios can occur if a subject has no prior history of breast cancer and has not had screenings.

Risk Scenario 1.

If a female subject has not had either screening test, and if the subject has weak familial risk for breast cancer and age=21 and has not had clinical breast exam within the past year, or user age=22 and <40 and has not had clinical breast exam within past 1 to 2 years, then the following recommendation is provided:

Talk to your health professional about a breast exam and when to get breast cancer screening.

A clinical breast exam is a breast cancer screening test that may help detect breast cancer early, when it is most treatable. Clinical breast exams are used in combination with mammograms when you reach age 40 and older. Talk to your health professional about breast cancer screening tests, and when and how often you should be screened.

Risk Scenario 2.

If a female subject has not had a mammogram within the past year and if the subject has weak familial risk for breast cancer and age=or >41, then the following recommendation is provided:

Schedule breast cancer screening today.

Mammograms and clinical breast exams are screening tests that can help detect breast cancer early, when it is most treatable. Talk to your health professional about scheduling breast cancer screening at least every one to two years.

Risk Scenario 3.

If a female subject has moderate familial risk for breast cancer and no personal history of breast cancer or ovarian cancer, and age=21 and has not had a clinical breast exam or mammogram within the past year, or subject age=22 or <40 and has not had clinical breast exam or mammogram within the past 1 to 2 years, then the following recommendation is provided:

You may benefit from breast cancer screening at a younger age than is usually recommended. Talk to your health professional about your family history, how it affects your breast cancer risk, and your options for screening and prevention.

Clinical breast exams and mammograms are screening tests that can help detect breast cancer early, when it is most treatable. Mammograms are most effective and reliable when performed in women age 40 and older. Due to your family history, a mammogram at an earlier age or another type of screening test or prevention option may be helpful. Talk to your health professional about your risk of breast cancer, the best tests for you, and when and how often you should be screened.

Risk Scenario 4.

If a female subject has moderate familial risk for breast cancer and no personal history of breast cancer or ovarian cancer, and age=or >41 and the subject has not had mammogram within past year, then the following recommendation is provided:

Schedule breast cancer screening today. Talk to your health professional about your family history, how it affects your breast cancer risk, and your options for screening and prevention.

Mammograms and clinical breast exams are screening tests that can help detect breast cancer early, when it is most treatable. Due to your family history, other screening tests or prevention options may be helpful. Talk to your health professional about your risk of breast cancer, the best tests for you, and how often you should be screened.

Risk Scenario 5.

If a female subject has high familial risk for breast cancer and no personal history of breast cancer or ovarian cancer, and age=or >21 and <40 and has not had a clinical breast exam within the past year or has not had a mammogram within past year, then the following recommendation is provided:

You may benefit from breast cancer screening at a younger age than is usually recommended. Talk to your health professional about your family history, how it affects your breast cancer risk, and your options for screening and prevention.

Mammograms and clinical breast exams are screening tests that can help detect breast cancer early, when it is most treatable. Mammograms are most effective and reliable when performed in women age 40 and older. Due to your family history, a mammogram at an earlier age may be helpful. There are also other ways to screen for and prevent breast cancer among women with the highest risk. Talk to your health professional about your breast cancer risk, the best tests for you, and when and how often you should be screened.

Risk Scenario 6.

If a female subject has high familial risk for breast cancer and no personal history of breast cancer or ovarian cancer, and age=or >41 and has not had mammogram within past year, then the following recommendation is provided:

Schedule breast cancer screening today. Talk to your health professional about your family history, how it affects your breast cancer risk, and your options for screening and prevention.

Mammograms and clinical breast exams are screening tests that help detect breast cancer early, when it is most treatable. There are also other ways to screen for and prevent breast cancer among women with the highest risk. Talk to your health professional about your risk of breast cancer, the best tests for you, and how often you should be screened.

The following four risk scenarios can occur if a subject has had screenings:

Risk Scenario 1.

If a female subject has moderate familial risk for breast cancer and no personal history of breast cancer or ovarian cancer, and age=21 and has had clinical breast exam or mammogram within the past year, or user age=22 or <40 and has had clinical breast exam or mammogram within past 1 to 2 years, then the following recommendation is provided:

Continue breast cancer screening. Talk to your health professional about your family history, how it affects your breast cancer risk, and your options for screening and prevention.

Clinical breast exams and mammograms are screening tests that can help detect breast cancer early, when it is most treatable. Mammograms are most effective and reliable when performed in women age 40 and older. Due to your family history, a mammogram at an earlier age or another type of screening test or prevention option may be helpful. Talk to your health professional about your risk of breast cancer, the best tests for you, and how often you should be screened.

Risk Scenario 2.

If a female subject has moderate familial risk for breast cancer and no personal history of breast cancer or ovarian cancer, and age=or >41 and has had mammogram within past year, then the following recommendation is provided:

Continue breast cancer screening. Talk to your health professional about your family history, how it affects your breast cancer risk, and your options for screening and prevention.

Mammograms and clinical breast exams are screening tests that can help detect breast cancer early, when it is most treatable. Due to your family history, other screening tests or prevention options may be helpful. Talk to your health professional about your risk of breast cancer, the best tests for you, and how often you should be screened.

Risk Scenario 3.

If a female subject has high familial risk for breast cancer and no personal history of breast cancer or ovarian cancer, and age=or >21 and <40 and has had clinical breast exam within the past year or has had mammogram within past year, then the following recommendation is provided:

Continue breast cancer screening. Talk to your health professional about your family history, how it affects your breast cancer risk, and your options for screening and prevention.

Mammograms and clinical breast exams are screening tests that can help detect breast cancer early, when it is most treatable. Mammograms are most effective and reliable when performed in women age 40 and older. Due to your family history, a mammogram at an earlier age may be helpful. There are also other ways to screen for and prevent breast cancer among women with the highest risk. Talk to your health professional about your risk of breast cancer, the best tests for you, and how often you should be screened.

Risk Scenario 4.

If a female subject has high familial risk for breast cancer and no personal history of breast cancer or ovarian cancer, and age=or >41 and has had mammogram within past year, then the following recommendation is provided:

Continue breast cancer screening. Talk to your health professional about your family history, how it affects your breast cancer risk, and your options for screening and prevention.

Mammograms and clinical breast exams are screening tests that can help detect breast cancer early, when it is most treatable. There are also other ways to screen for and prevent breast cancer among women with the highest risk. Talk to your health professional about your risk of breast cancer, the best tests for you, and how often you should be screened.

Example 30

Exemplary Ovarian Cancer Disease Prevention Recommendations

An exemplary disease prevention plan (according to system 3600) based on familial risk assessment is shown below.

The following risk scenarios are examples of exemplary disease prevention plan recommendations based ovarian familial risk assessment. The following two risk scenarios can occur if a female subject has not had screenings.

Risk Scenario 1.

If a female subject has a moderate familial risk for ovarian cancer and age=or >20 and no personal history of ovarian cancer or breast cancer, then the following recommendation is provided:

Screening tests are sometimes offered to women with an increased risk of ovarian cancer. Talk to your health professional about your family history, how it affects your ovarian cancer risk, and your options for screening and prevention.

Available tests for ovarian cancer screening include a blood test called CA-125 and ultrasound of the ovaries. These tests can be used alone or in combination. Talk to your health professional about your risk of ovarian cancer, the benefits and limits of the available tests, and which prevention and screening options are best for you.

Risk Scenario 2.

If a female subject has a high familial risk for ovarian cancer and age=or >20 and no personal history of ovarian cancer or breast cancer, then the following recommendation is provided:

Screening tests are sometimes offered to women with an increased risk of ovarian cancer. Talk to your health professional about your family history, how it affects your ovarian cancer risk, and your options for screening and prevention.

Available tests for ovarian cancer screening include a blood test called CA-125 and ultrasound of the ovaries. These tests can be used alone or in combination. Because your family history is a strong risk factor for ovarian cancer, these tests may be recommended. Talk to your health professional about your risk of ovarian cancer, the benefits and limits of the available tests, and which prevention and screening options are best for you.

Example 31

Exemplary Colon Cancer Disease Prevention Recommendations

An exemplary disease prevention plan (according to system 3600) based on colon cancer familial risk assessment and screening questions is shown below. Screening questions can include the following questions:

1) A fecal occult blood test ("FOBT") is a test kit that you receive from your health professional. At home, you put a small piece of stool on a test card. You do this for three bowel movements in a row. Then you return the test cards to the health professional or lab. The stool samples are checked for blood. Have you had a fecal occult blood test?

_____ Never
_____ Yes, within the past year
_____ Yes, 1 to 2 years ago
_____ Yes, 3 to 5 years ago
_____ Yes, 6 to 10 years ago
_____ Yes, more than 10 years ago
_____ Don't know/Not sure 2) A colonoscopy is an examination that checks the entire colon. A tube is inserted in the rectum to view the bowel for signs of cancer or other health problems. Heavy sedation or pain medication usually is required. Have you had a colonoscopy?

_____ Never
_____ Yes, within the past year
_____ Yes, 1 to 2 years ago
_____ Yes, 3 to 5 years ago
_____ Yes, 6 to 10 years ago
_____ Yes, more than 10 years ago
_____ Don't know/Not sure 3) A sigmoidoscopy is an examination that checks the lower part of the colon. A tube is inserted in the rectum to view the bowel for signs of cancer or other health problems. Heavy sedation or pain medication usually is not required. Have you had a sigmoidoscopy?

_____ Never
_____ Yes, within the past year
_____ Yes, 1 to 2 years ago
_____ Yes, 3 to 5 years ago
_____ Yes, 6 to 10 years ago
_____ Yes, more than 10 years ago
_____ Don't know/Not sure The following risk scenarios are examples of exemplary disease prevention plan recommendations based on answers to the above questions and colon cancer familial risk assessment.

The following six risk scenarios can occur if a subject has not had screenings.

Risk Scenario 1.

If a subject has average familial risk for colon cancer and age=51 and has not had FOBT or sigmoidoscopy or colonoscopy within past year; or age=52 and has not had FOBT within past year, or sigmoidoscopy or colonoscopy; or within past 1 to 2 years; or age=53 and has not had FOBT within past year, or sigmoidoscopy or colonoscopy within past 3 to 5 years; or age=54 and has not had FOBT within past year, or sigmoidoscopy or colonoscopy within past 3 to 5 years; or age=55 and has not had FOBT within past year, or sigmoidoscopy or colonoscopy within past 3 to 5 years; or age=56 and has not had FOBT within past year, or sigmoidoscopy in past 3 to 5 years, or colonoscopy in past 6 to 10 years; or age=57 and has not had FOBT within past year, or sigmoidoscopy within past 3 to 5 years, or colonoscopy within past 6 to 10 years; or age=58 and has not had FOBT within past year, or sigmoidoscopy within past 3 to 5 years, or colonoscopy within past 6 to 10 years; or age=59 and has not had FOBT within past year, or sigmoidoscopy within past 3 to 5 years, or colonoscopy within past 6 to 10 years; or age=or >60 and has not had FOBT within past year, or sigmoidoscopy within past 3 to 5 years, or colonoscopy within past 6 to 10 years, then the following recommendation is provided:

Schedule a colon cancer screening test today.

Colon cancer screening can help find colon cancer early, when it is most treatable. It also can detect polyps (small growths), which can be removed to prevent colon cancer. Colon cancer screening can involve a home stool test kit, sigmoidoscopy, double-contrast barium enema, and/or colonoscopy. These tests can be done alone or in combination. Usually, a home stool test is done every year, sigmoidoscopy at least every 5 years, double-contrast barium enema at least every 5 years, and colonoscopy at least every 10 years. Talk to your health professional about your risk of colon cancer, the tests that are best for you, and when and how often you should be screened.

Risk Scenario 2.

If a subject has moderate familial risk for colon cancer and no personal history of colon cancer and age=20 and <41, then the following recommendation is provided:

You may benefit from colon cancer screening tests at a younger age than usually is recommended. Talk to your health professional about your family history, how it affects your colon cancer risk, and your options for screening and prevention.

Colon cancer screening can help find colon cancer early, when it is most treatable. It also can detect polyps (small growths), which can be removed to prevent colon cancer. Colon cancer screening tests include: a home stool test kit, sigmoidoscopy, double-contrast barium enema, and/or colonoscopy. These tests can be done alone or in combination, and are usually recommended for people aged 50 and older. However, people with an increased risk due to family history often start testing at age 40. Usually, a home stool test is done every year, sigmoidoscopy at least every 5 years, double-contrast barium enema at least every 5 years, and colonoscopy at least every 10 years. Talk to your health professional about your risk of colon cancer, the tests that are best for you, and when and how often you should be screened.

Risk Scenario 3.

If a subject has moderate familial risk for colon cancer and no personal history of colon cancer and age=41 and has not had FOBT or sigmoidoscopy or colonoscopy within past year; or age=42 and has not had FOBT within past year, or sigmoidoscopy or colonoscopy within past 1 to 2 years; or age=43 and has not had FOBT within past year, or sigmoidoscopy or colonoscopy within past 3 to 5 years; or age=44 and has not had FOBT within past year, or sigmoidoscopy or colonoscopy within past 3 to 5 years; or age=45 and has not had FOBT within past year, or sigmoidoscopy or colonoscopy in past 3 to 5 years; or age=46 and has not had FOBT within past year, or sigmoidoscopy within past 3 to 5 years, or colonoscopy within past 6 to 10 years; or age=47 and has not had FOBT within past year, or sigmoidoscopy within past 3 to 5 years, or colonoscopy in past 6 to 10 years; or age=48 and has not had FOBT within past year, or sigmoidoscopy within past 3 to 5 years, or colonoscopy within past 6 to 10 years; or age=49 and has not had FOBT within past year, or sigmoidoscopy within past 3 to 5 years, or colonoscopy within past 6 to 10 years, then the following recommendation is provided:

You may benefit from colon cancer screening tests at a younger age than usually is recommended. Talk to your health professional about your family history, how it affects your colon cancer risk, and your options for screening and prevention.

Colon cancer screening can help find colon cancer early, when it is most treatable. It also can detect polyps (small growths), which can be removed to prevent colon cancer. Colon cancer screening tests include: a home stool test kit, sigmoidoscopy, double-contrast barium enema, and/or colonoscopy. These tests can be done alone or in combination, and are usually recommended for people aged 50 and older. However, people with an increased risk due to family history often start testing at age 40. Usually, a home stool test is done every year, sigmoidoscopy at least every 5 years, double-contrast barium enema at least every 5 years, and colonoscopy at least every 10 years. Talk to your health professional about your risk of colon cancer, the tests that are best for you, and when and how often you should be screened.

Risk Scenario 4.

If a subject has moderate familial risk for colon cancer and no personal history of colon cancer and their age=or >50 and has not had FOBT within past year, or sigmoidoscopy within past 3 to 5 years, or colonoscopy within past 6 to 10 years then the following recommendation is provided:

Schedule a colon cancer screening test today. Talk to your health professional about your family history, how it affects your colon cancer risk, and your options for screening and prevention.

Colon cancer screening can help find colon cancer early, when it is most treatable. It also can detect polyps (small growths), which can be removed to prevent colon cancer. Colon cancer screening tests include: a home stool test kit, sigmoidoscopy, double-contrast barium enema, and/or colonoscopy. These tests can be done alone or in combination and are usually recommended for people aged 50 and older. Usually, a home stool test is done every year, sigmoidoscopy at least every 5 years, double-contrast barium enema at least every 5 years, and colonoscopy at least every 10 years. Talk to your health professional about your risk of colon cancer, the tests that are best for you, and how often you should be screened.

Risk Scenario 5.

If a subject has high (e.g., strong) familial risk for colon cancer and no personal history of colon cancer and age=20 to 30, then the following recommendation is provided:

You may benefit from colon cancer screening tests at a younger age than usually is recommended. Talk to your health professional about your family history, how it affects your colon cancer risk, and your options for screening and prevention.

Colon cancer screening can help find colon cancer early, when it is most treatable. It also can detect polyps (small growths), which can be removed to prevent colon cancer. Because of your high risk, colonoscopy may be the best screening test for you. Other screening tests include a home stool test kit, sigmoidoscopy, and double-contrast barium enema. While colon cancer screening is usually recommended for people aged 50 and older, people with an increased risk due to family history often start testing at age 40, and families with the highest risk sometimes start testing as early as age 20 to 30. Talk to your health professional about your risk of colon cancer, the tests that are best for you, and when and how often you should be screened.

Risk Scenario 6.

If a subject has high (e.g., strong) familial risk for colon cancer and no personal history of colon cancer and age=31 and has not had colonoscopy within past year; or age=32 and has not had colonoscopy within past 1 to 2 years; or age=33 and has not had colonoscopy within past 3 to 5 years; or age=34 and has not had colonoscopy within past 3 to 5 years; or age=or >35 and has not had colonoscopy within past 3 to 5 years, then the following recommendation is provided:

You may benefit from colon cancer screening tests at a younger age than usually is recommended. Talk to your health professional about your family history, how it affects your colon cancer risk, and your options for screening and prevention.

Colon cancer screening can help find colon cancer early, when it is most treatable. It also can detect polyps (small growths), which can be removed to prevent colon cancer. Because of your high risk, colonoscopy may be the best screening test for you. Other screening tests include a home stool test kit, sigmoidoscopy, and double-contrast barium enema. While colon cancer screening is usually recommended for people aged 50 and older, people with increased risk due to family history often start testing at age 40, and families with the highest risk sometimes start testing as early as age 20 to 30. Talk to your health professional about your risk of colon cancer, the tests that are best for you, and when and how often you should be screened.

The following two risk scenarios can occur if a subject has had screenings.

Risk Scenario 1.

If a subject has moderate familial risk for colon cancer and no personal history of colon cancer, and age=41 and has had FOBT or sigmoidoscopy or colonoscopy within past year; or age=42 and has had FOBT within past year, or sigmoidoscopy or colonoscopy within past 1 to 2 years; or age=43 and has had FOBT within past year, or sigmoidoscopy or colonoscopy within past 3 to 5 years; or age=44 and has had FOBT within past year, or sigmoidoscopy or colonoscopy within past 3 to 5 years; or age=45 and has had FOBT within past year, or sigmoidoscopy or colonoscopy within past 3 to 5 years; or age=46 and has had FOBT within past year, or sigmoidoscopy within past 3 to 5 years, or colonoscopy within past 6 to 10 years; or age=47 and has had FOBT within past year, or sigmoidoscopy within past 3 to 5 years, or colonoscopy within past 6 to 10 years; or age=48 and has had FOBT within past year, or sigmoidoscopy within past 3 to 5 years, or colonoscopy within past 6 to 10 years; or age=49 and has had FOBT within past year, or sigmoidoscopy within past 3 to 5 years, or colonoscopy within past 6 to 10 years; or age=or >50 and has had FOBT within past year, or sigmoidoscopy within past 3 to 5 years, or colonoscopy within past 6 to 10 years, then the following recommendation is provided:

Continue colon cancer screening. Talk to your health professional about your family history, how it affects your colon cancer risk, and your options for screening and prevention.

Colon cancer screening can help find colon cancer early, when it is most treatable. It also can detect polyps (small growths), which can be removed to prevent colon cancer. Colon cancer screening tests include: a home stool test kit, sigmoidoscopy, double-contrast barium enema, and/or colonoscopy. These tests can be done alone or in combination, and are usually recommended for people aged 50 and older. However, people with an increased risk due to family history often start testing at age 40. Usually, a home stool test is done every year, sigmoidoscopy at least every 5 years, double-contrast barium enema at least every 5 years, and colonoscopy at least every 10 years. Talk to your health professional about your risk of colon cancer, the screening tests that are best for you, and how often you should be screened.

Risk Scenario 2.

If a subject has high (e.g., strong) familial risk for colon cancer and no personal history of colon cancer, and age=31 and has had colonoscopy within past year; or age=32 and has had colonoscopy within past 1 to 2 years; or age=33 and has had colonoscopy within past 3 to 5 years; or age=34 and has had colonoscopy within past 3 to 5 years; or age=or >35 and has had colonoscopy within past 3 to 5 years, then the following recommendation is provided:

Continue colon cancer screening. Talk to your health professional about your family history, how it affects your colon cancer risk, and your options for screening and prevention.

Colon cancer screening can help find colon cancer early, when it is most treatable. It also can detect polyps (small growths), which can be removed to prevent colon cancer. Because of your high risk, colonoscopy may be the best screening test for you. Other screening tests include a home stool test kit, sigmoidoscopy, and double-contrast barium enema. While colon cancer screening is usually recommended for people aged 50 and older, people with increased risk due to family history often start testing at age 40, and families with the highest risk sometimes start testing as early as age 20 to 30. Talk to your health professional about your risk of colon cancer, the screening tests that are best for you, and how often you should be screened.

Example 32

Exemplary Coronary Heart Disease and Stroke Prevention Recommendations

An exemplary disease prevention plan (according to system 3600) based on coronary heart disease and/or stroke familial risk assessment and screening questions is shown below. A blood cholesterol screening question can include the following question:

1) Blood cholesterol is a fatty substance found in the blood. Have you had your blood cholesterol checked by a health professional?
_____ Never
_____ Yes, within the past year
_____ Yes, 1 to 2 years ago
_____ Yes, 3 to 5 years ago
_____ Yes, 6 to 10 years ago
_____ Yes, more than 10 years ago
_____ Don't know/Not sure The following three risk scenarios can occur if a subject has not had screenings.

Risk Scenario 1.

If a subject is a woman and has weak familial risk for coronary artery disease and stroke, and age=or >46 and has not had cholesterol test within the past year; or age=47 and has not had cholesterol tested in the past 2 years; or age=48 and has not had cholesterol tested in past 3 years; or age=49 and has not had cholesterol tested in past 4 years; or age=or >50 and has not had cholesterol tested in past 5 years, then the following recommendation is provided:

Get your cholesterol tested.

Your cholesterol testing should include a measure of your total cholesterol, low density lipoprotein (the "bad" cholesterol), high density lipoprotein (the "good" cholesterol), and triglycerides. If your cholesterol levels are high or abnormal, changing your lifestyle and/or taking medication can reduce your risk of coronary heart disease and stroke. Ask your health professional how often you should test your cholesterol. This will depend on your cholesterol levels, other risk factors, and if you already are being treated for cholesterol problems.

Risk Scenario 2.

If a subject is a man and has low (e.g., weak) familial risk for coronary artery disease and stroke, and age=or >36 and has not had cholesterol test within past year; or age=37 and has not had cholesterol tested in past 2 years; or age=38 and has not had cholesterol tested in past 3 years; or age=39 and has not had cholesterol tested in past 4 years; or age=or >40 and has not had cholesterol tested in past 5 years, then the following recommendation is provided:

Get your cholesterol tested.

Your cholesterol testing should include a measure of your total cholesterol, low density lipoprotein (the "bad" cholesterol), high density lipoprotein (the "good" cholesterol), and triglycerides. If your cholesterol levels are high or abnormal, changing your lifestyle and/or taking medication can reduce your risk of coronary heart disease and stroke. Ask your health professional how often you should test your cholesterol. This will depend on your cholesterol levels, other risk factors, and if you already are being treated for cholesterol problems.

Risk Scenario 3.

If a subject has moderate or high (e.g., strong) familial risk for coronary heart disease and no personal history of coronary heart disease, stroke or diabetes, and age=21 and has not had cholesterol test within the past year; or age=22 and has not had cholesterol test within past 1 to 2 years; or age=23 and has not had cholesterol test within past 2 to 5 years; or age=24 and has not had cholesterol test within past 2 to 5 years; or age=or >25 and has not had cholesterol test within past 5 years, then the following recommendation is provided:

Get your cholesterol tested. Talk to your health professional about your family history, how it affects your risk of coronary heart disease or stroke, and your options for screening and prevention.

Your cholesterol testing should include a measure of your total cholesterol, low density lipoprotein (the "bad" cholesterol), high density lipoprotein (the "good" cholesterol), and triglycerides. If your cholesterol levels are high or abnormal, changing your lifestyle and/or taking medication can reduce your risk of coronary heart disease and stroke. Due to your increased risk, you may need to test for other cardiovascular risk factors. Ask your health professional how often you should test your cholesterol. This will depend on your cholesterol levels, other risk factors, and if you already are being treated for cholesterol problems.

The following risk scenario can occur if a subject has had cholesterol screenings.

Risk Scenario 1.

If a subject has moderate or high (e.g., strong) familial risk for coronary heart disease or stroke and no personal history of coronary heart disease, stroke or diabetes, and age=21 and has had cholesterol test in past year; or age=22 and has had cholesterol test in past 2 years; or age=23 and has had cholesterol test in past 3 years; or age=24 and has had cholesterol test in past 4 years; or age=or >25 and has had cholesterol test in past 5 years, then the following recommendation is provided:

Continue cholesterol testing. Talk to your health professional about your family history, how it affects your risk of <coronary heart disease or stroke>, and your options for screening and prevention.

Your cholesterol testing should include a measure of your total cholesterol, low density lipoprotein (the "bad" cholesterol), high density lipoprotein (the "good" cholesterol), and triglycerides. If your cholesterol levels are high or abnormal, changing your lifestyle and/or taking medication can reduce your risk of coronary heart disease and stroke. Due to your increased risk, you may need to test for other cardiovascular risk factors. Ask your health professional how often you should test your cholesterol. This will depend on your cholesterol levels, other risk factors, and if you already are being treated for cholesterol problems.

Similarly, a blood screening question can include the following question:

1) Have you had your blood pressure checked by a health professional?

_____ Never
_____ Yes, within the past year
_____ Yes, 1 to 2 years ago
_____ Yes, 3 to 5 years ago
_____ Yes, 6 to 10 years ago
_____ Yes, more than 10 years ago
_____ Don't know/Not sure The following two risk scenarios can occur if a subject has had blood pressure screening:

Risk Scenario 1.

If a subject has low (e.g., weak) familial risk for coronary heart disease and stroke, and has not had blood pressure checked in past year, and age=or >19, then the following recommendation is provided:

Get your blood pressure checked.

If your blood pressure is high, changing your lifestyle and/or taking medication can lower your blood pressure and reduce your risk of coronary heart disease and stroke. Ask your health professional how often you should check your blood pressure. This will depend on your blood pressure levels, other health problems, and if you already are being treated for high blood pressure.

Risk Scenario 2.

If a subject has moderate or high (e.g., strong) familial risk for coronary heart disease or stroke and has no personal history of coronary heart disease, stroke or diabetes, and has not had blood pressure checked in past year, and age=or >19, then the following recommendation is provided:

Get your blood pressure checked. Talk to your health professional about your family history, how it affects your risk of <coronary heart disease or stroke>, and your options for screening and prevention.

If your blood pressure is high, changing your lifestyle and/or taking medication can lower your blood pressure and reduce your risk of coronary heart disease and stroke. Ask your health professional how often you should check your blood pressure. This will depend on your blood pressure levels, other health problems, and if you already are being treated for high blood pressure.

The following risk scenario can occur if a subject has had blood pressure screening:

Risk Scenario 1.

If a subject has moderate or high (e.g., strong) familial risk for coronary heart disease or stroke and has no personal history of coronary heart disease, stroke and diabetes, and has had blood pressure checked in past year, and age=or >19, then the following recommendation is provided:

Continue to check your blood pressure. Talk to your health professional about your family history, how it affects your risk of <coronary heart disease or stroke>, and your options for screening and prevention.

If your blood pressure is high, changing your lifestyle and/or taking medication can lower your blood pressure and reduce your risk of coronary heart disease and stroke. Ask your health professional how often you should check your blood pressure. This will depend on your blood pressure levels, other health problems, and if you already are being treated for high blood pressure.

Example 33

Exemplary Diabetes Prevention Recommendations

An exemplary disease prevention plan (according to system 3600) based on diabetes familial risk assessment and a screening question is shown below. A blood glucose screening question can include the following question:

1) A blood sugar test is a blood test that looks for and measures your blood glucose or blood sugar. Have you had your blood sugar tested by a health professional?

_____ Never
_____ Yes, within the past year
_____ Yes, 1 to 2 years ago
_____ Yes, 3 to 5 years ago
_____ Yes, 6 to 10 years ago
_____ Yes, more than 10 years ago
_____ Don't know/Not sure The following risk scenario can occur:

Risk Scenario 1.

If a subject has moderate or high (e.g., strong) familial risk for diabetes, coronary heart disease and/or stroke and no personal history of diabetes, coronary heart disease or stroke, and has not had their blood sugar tested in the past 2 years and age > or =22, then the following recommendation is provided:

You may benefit from blood sugar testing because of your family history. Talk to your health professional about your blood sugar and how it affects your risk of disease.

Elevated blood sugar is a sign of diabetes, and it can increase the risk of coronary heart disease and stroke. If you have elevated blood sugar, you can lower it by changing your lifestyle and/or taking medication. In addition, your health professional may closely monitor and manage other cardiovascular risk factors like blood pressure and cholesterol. These steps may reduce your chances of coronary heart disease and stroke. Ask your health professional about scheduling a blood sugar test.

Example 34

Exemplary General Screening Test Recommendations Based Upon Familial Risk Assessment Exemplary disease prevention plan (e.g. a disease prevention plan according to system 3600) general gender-specific screening test recommendations including when to begin and interval of screening based on familial risk assessment are shown in Table 1. Screening test recommendations can be further based on available guidelines (e.g., guidelines from the U.S. Preventive Services Task Force, National Cancer Institute, National Heart, Lung and Blood Institute, American Cancer Society, and the American Hearth Association and the like). The screening test recommendations provided can be presented as part of a complete overall disease prevention plan for a subject, or by one or more diseases of interest.

TABLE 1

| Disease | Screening Test | Risk Status | RECOMMENDEDATION PROVIDED |
|---|---|---|---|
| Heart Disease & Stroke | Cholesterol | Average/Weak | For women, screening should begin at age 45 with a frequency of at least every 5 years<br>For men, screening should begin at age 35 with a frequency of at least every 5 years |
| | | Moderate | For men and women, screening should begin at age 20 with a frequency of at least every 5 years |
| | | High/Strong | For men and women, screening should begin at age 20 with a frequency of at least every 5 years |
| | Blood Pressure | Average | For men and women, screening should begin at age 18 with a frequency of at least every year |
| | | Moderate | For men and women, screening should begin at age 18 with a frequency of at least every year |
| | | High | For men and women, screening should begin at age 18 with a frequency of at least every year |
| | Blood Glucose | Average | No message |
| | | Moderate | For men and women, screening should begin at age 20 with a frequency of at least every two years |
| | | High | For men and women, screening should begin at age 20 with a frequency of at least every two years |
| Diabetes | Blood Glucose | Average | No message |
| | | Moderate | For men and women, screening should begin at age 20 with a frequency of at least every two years |
| | | High | For men and women, screening should begin at age 20 with a frequency of at least every two years |
| Breast Cancer | CBE MG | Average | For women between ages 20 to 40, screening with CBE is an option beginning at age 20 with a frequency of every 1-2 years.<br>For women age 40 and older, screening with mammography should begin at age 40 with a frequency of every 1-2 years.<br>(CBE every 1 to 2 years is also suggested). |
| | | Moderate | For women between ages 20 to 40, screening with CBE and/or mammogram may be an option with a frequency of every 1-2 years<br>For women age 40 and older, screening with mammography should begin at age 40 with a frequency of every year. (CBE every 1 to 2 years is also suggested) |
| | | High | For women between ages 20 to 40, screening with CBE and/or mammography mat be an option with a frequency of every year.<br>For women age 40 and older, screening with mammography should begin at age 40 with a frequency of every year. |
| Ovarian Cancer | CA-125 Transvaginal Ultrasound | Average | No Message |
| | | Moderate | For women beginning age at 20, discuss screening (i.e., CA125, TVUS) with health professional. |
| | | High | For women beginning at age 20, discuss screening (i.e., CA125, TVUS) with health professional |
| Colon Cancer | FOBT Flex Sig DCBE Colonoscopy | Average | For men and women, begin screening at age 50. Frequency of screening with FOBT every year; with flexible sigmoidoscopy at least every 5 years; with DCBE at least every 5 years; and with colonoscopy at least every 10 years. |

TABLE 1-continued

| Disease | Screening Test | Risk Status | RECOMMENDEDATION PROVIDED |
|---|---|---|---|
| | | Moderate | For men and women between ages 20 to 40, discuss screening with health professional. For men and women, begin screening at age 40. Frequency of screening with FOBT every year; with flexible sigmoidoscopy at least every 5 years; with DCBE at least every 5 years; and with colonoscopy at least every 10 years. |
| | | High | For men and women between ages 20 to 30, discuss screening with health professional For men and women age 30 and older, begin screening with colonoscopy at age 30 with a frequency of at least every 5 years. (Other screening modalities are suggested as options.) |

Example 35

Exemplary General Lifestyle/Behavior Recommendations Based Upon Familial Risk Assessment and Personal Health History Exemplary disease prevention plan (e.g. a disease prevention plan according to system 3600) gender and age-based lifestyle/behavior recommendations based on familial risk assessment and personal health history are shown in Table 2. Lifestyle/Behavior recommendations can be further based on available guidelines (e.g., guidelines from the U.S. Preventive Services Task Force, National Cancer Institute, National Heart, Lung and Blood Institute, American Cancer Society, and the American Hearth Association and the like). The lifestyle/behavior recommendations provided can be presented as part of a complete overall disease prevention plan for a subject, or by one or more diseases of interest.

Example 36

Exemplary Lifestyle/Behavior Recommendations Based Upon Familial Risk Assessment and Personal Health History An exemplary disease prevention plan (according to system 3600) based on familial risk assessment and the screening questions is shown below. Body mass index (BMI) screening questions can include the following questions:

1) What is your current height? _____ feet _____ inches

2) What is your current weight (If you are pregnant, what was your weight prior to pregnancy) ? _____ pounds The following risk scenarios can occur based on familial risk for disease and the response to the above questions:

TABLE 2

| Lifestyle/ Behavior | Linked to Disease? | Risk Status | RECOMMENDATION PROVIDED |
|---|---|---|---|
| BMI | CHD, stroke, DM, | Average | BMI < 18.5 Underweight- Talk to doctor<br>BMI ≥ 25 Lose weight to reduce risk of CVD, diabetes and cancer |
| | Breast CA, Colon CA | Moderate or High | BMI < 18.5 Underweight- Talk to doctor<br>BMI ≥ 25 Lose weight to reduce risk of <disease>.<br>BMI = 18.5 to 24.9 Maintaining weight may reduce risk of <disease>. |
| Tobacco | CHD, stroke, Colon CA | Average | Smoker Quit smoking |
| | | Moderate or High | Smoker Quit smoking to reduce risk of <disease>.<br>Former Smoker Keep avoiding to reduce risk of <disease> |
| Physical Activity | CHD, stroke, DM, | Average | Does not Exercise (as recommended) ↑ physical activity . . . may improve health |
| | Breast CA, Colon CA | Moderate or High | Does not Exercise ↑ physical activity may reduce risk of <disease>.<br>Does Exercise Continue. May reduce risk of <disease>. |
| 5-A-Day (Diet) | CHD, stroke, Breast CA, Colon CA | Average | <5-a-day ↑ intake . . . may improve health |
| | | Moderate or High | <5-a-day ↑ intake . . . may reduce risk of <disease>.<br>≥5-a-day Continue. May reduce risk of <disease>. |
| Alcohol | Colon cancer, breast cancer | Any | Female & drinks Limit to one a day<br>Male & drinks Limit to one or two a day |
| Aspirin | CHD, stroke, Colon CA | Moderate or High | Uses less than 3x/wk Aspirin may reduce risk of <disease> . . . Talk to doctor.<br>Uses 3 or more times a week. Asp. may reduce risk of <disease>. Talk to doctor. |

Risk Scenario 1.

If BMI is <18.5 and if the subject has any familial risk for coronary heart disease, stroke, diabetes, colon cancer and breast cancer, and ovarian cancer, the following recommendation is provided:

You are underweight for your height. Talk to your health professional about your weight, and how it affects your health.

Based on your height, your ideal weight ranges from _____ to _____ pounds. Being underweight can be a sign of a health problem, especially if you have had an unplanned weight loss.

Risk Scenario 2.

If BMI is =or >25 and if the subject has weak familial risk for coronary heart disease, stroke, diabetes, colon cancer and breast cancer, and any familial risk for ovarian cancer, then the following recommendation is provided:

Losing weight may reduce your risk of getting cardiovascular disease, diabetes and cancer, and improve your overall health.

Based on your height, your ideal weight ranges from <_____ to _____ pounds>. Even a weight loss of a few pounds can make a difference. Talk to your health professional about a nutrition and physical activity program that is right for you.

Risk Scenario 3.

If BMI is =or >25 and if the subject has moderate or high (e.g., strong) familial risk for coronary heart disease, stroke, diabetes, colon cancer or breast cancer and no personal history of coronary heart disease, stroke, diabetes, colon cancer and breast cancer, then the following recommendation is provided:

Losing weight may reduce your risk of getting <diseases> and improve your overall health.

Based on your height, your ideal weight ranges from <_____ to _____ pounds>. Even a weight loss of a few pounds can make a difference. Talk to your health professional about a nutrition and physical activity program that is right for you.

Risk Scenario 4.

If BMI=18.5 to 24.9 and if the subject has moderate or high (e.g., strong) familial risk for coronary heart disease, stroke, diabetes, colon cancer or breast cancer and no personal history of coronary heart disease, stroke, diabetes, colon cancer and breast cancer, then the following recommendation is provided:

Your weight is appropriate for your height. Maintaining a healthy weight may reduce your risk of <diseases> and improve your overall health.

Based on your height, your ideal weight ranges from <_____ to _____ pounds>.

Tobacco use screening questions can include the following question:

1) Do you smoke tobacco including cigarettes, a pipe, or cigars?

_____ Yes, I currently smoke cigarettes, a pipe, or cigars

_____ No, but I used to smoke

_____ No, I have never smoked (or I have smoked less than 100 cigarettes in my lifetime)

The following risk scenarios can occur based on familial risk for disease and the response to the above questions:

Risk Scenario 1.

If a subject smokes and has weak familial risk for coronary heart disease, stroke, or colon cancer, and any level of familial risk for diabetes, breast and ovarian cancer, then the following recommendation is provided:

Quit smoking. Smoking increases your risk of cardiovascular disease, lung disease, cancer, and other health problems.

(For women) If you are pregnant and smoke, quitting now will help prevent health problems for you and your fetus. Talk to your health professional about programs to help you quit. Medication and counseling can help you quit. Make a plan and set a quit date. Tell your family, friends, and coworkers you are quitting and ask for their support.

Risk Scenario 2.

If a subject smokes and has moderate or high (e.g., strong) familial risk for coronary heart disease, stroke, or colon cancer and no personal history of coronary heart disease, stroke, diabetes, or colon cancer, then the following recommendation is provided:

Quit smoking to reduce your risk of <disease(s)> and to improve your overall health.

(For women) If you are pregnant and smoke, quitting now will help prevent health problems for you and your fetus. Talk to your health professional about programs to help you quit. Medication and counseling can help you quit. Make a plan and set a quit date. Tell your family, friends, and coworkers you are quitting and ask for their support.

Risk Scenario 3.

If a subject is a former smoker and has moderate or high (e.g., strong) familial risk for coronary heart disease, stroke or colon cancer and no personal history of coronary heart disease, stroke, diabetes or colon cancer, then the following recommendation is provided:

Congratulations for quitting smoking. Keep it up.

Continue to avoid smoking to reduce your risk of <disease(s)> and to improve your overall health. If you think you might start smoking again, ask your health professional for help.

Physical activity screening questions can include the following questions:

1) On average, how many times per week do you participate in physical activity such as running, golf, gardening, exercise classes, bicycling, swimming, walking, mowing the lawn, or dancing?

_____ Never

_____ Less than once a week

_____ 1 to 2 times a week

_____ 3 to 4 times a week

_____ 5 or more times a week

2) On average, how long do you do these activities each time?

_____ less than 10 minutes

_____ 10 to 19 minutes

_____ 20 to 29 minutes

_____ 30 to 39 minutes

_____ 40 or more minutes

The following risk scenarios can occur based on familial risk for disease and the response to the above questions:

Risk Scenario 1.

If a subject does not participate in physical activity at least 3 times a week and at least 20 minutes each time, and has weak familial risk for coronary heart disease, stroke, diabetes, colon cancer and breast cancer, and any familial risk for ovarian cancer, then the following recommendation is provided:

Increase your physical activity. This may improve your health and reduce your risk of cardiovascular disease, diabetes, cancer, and other health problems.

The ideal level of activity is at least 30 minutes of moderate activity on five or more days a week, or at least 20 minutes of vigorous activity on three or more days a week. If you need help getting more physical activity, ask your health professional for ideas or a referral.

Risk Scenario 2.

If a subject does not participate in physical activity at least 3 times a week and at least 20 minutes each time, and has moderate or high (e.g., strong) familial risk for coronary heart disease, stroke, diabetes, colon cancer or breast cancer and has no personal history of coronary heart disease, stroke, diabetes, colon cancer and breast cancer, then the following recommendation is provided:

Increase your physical activity. This may reduce your risk of <disease(s)> and improve your overall health.

The ideal level of activity is at least 30 minutes of moderate activity on five or more days a week, or at least 20 minutes of vigorous activity on three or more days a week. If you need help getting more physical activity, ask your health professional for ideas or a referral.

Risk Scenario 3.

If a subject does participate in physical activity at least 3 times a week and for at least 20 minutes each time, and has moderate or high (e.g., strong) familial risk for coronary heart disease, stroke, diabetes, colon cancer or breast cancer and no personal history of coronary heart disease, stroke, diabetes, colon cancer or breast cancer, then the following recommended is provided:

Keep getting regular physical activity. This may reduce your risk of <disease(s)> and improve your overall health.

The ideal level of activity is at least 30 minutes of moderate activity on five or more days a week, or at least 20 minutes of vigorous activity on three or more days a week. If you need help getting more physical activity, ask your health professional for ideas or a referral.

The following definitions of physical activity can also be provided with any recommendation provided:

Moderate physical activity—This level of activity generally refers to the level of effort that a healthy person might expend while walking briskly, mowing the lawn, dancing, swimming, or bicycling on a flat surface, for example. A person doing moderate physical activity will feel some exertion, but they will still be able to talk comfortably.

Vigorous physical activity—This level of activity generally refers to the level of effort that a healthy person might expend while jogging, mowing the lawn with a non-motorized push mower, chopping wood, swimming continuous laps, or bicycling uphill, for example. A person doing vigorous physical activity will feel physically challenged and their heart rate and breathing will increase significantly.

Dietary (e.g., 5-A-Day) screening questions can include the following questions:

1) On average, how many servings of fruits and vegetables do you eat each day? One serving is 1 medium piece of fruit, ½ cup fruit or vegetables (raw, cooked, canned, or frozen), 1 cup of leafy salad greens, ¼ cup of dried fruit, ¾ cup or 6 ounces of 100% juice, ½ cup cooked peas or beans.

_____ None
_____ 1 to 2 a day
_____ 3 to 4 a day
_____ 5 to 6 a day
_____ 7 to 8 a day
_____ 8 to 9 a day
_____ 10 or more a day The following risk scenarios can occur based on familial risk for disease and the response to the above question:

Risk Scenario 1.

If a subject eats less than 5 servings of fruits and vegetables per day and has weak familial risk for coronary heart disease, stroke, colon cancer and breast cancer, and any level of familial risk for diabetes and ovarian cancer, the following recommendation is provided:

Increase your daily intake of fruits and vegetables. This may improve your overall health and reduce your risk for cardiovascular disease and certain cancers.

Experts recommend eating 5 to 9 servings of fruits and vegetables a day. Try to eat a variety of different colored fruits and vegetables daily, especially darker green and yellow/orange choices. Fresh, frozen, chilled, canned, dried, and 100% fruit and vegetables juice all count. But limit or avoid fruits or vegetables that are high in added fat, sugar or salt, If you need help adding more fruits and vegetables to your diet, ask your health professional for ideas or a referral.

Risk Scenario 2.

If a subject eats less than 5 servings of fruits and vegetables per day and has moderate or high (e.g., strong) familial risk for coronary heart disease, stroke, colon cancer or breast cancer and no personal history of coronary heart disease, stroke, colon cancer and breast cancer, then the following recommendation is provided:

Increase your daily intake of fruits and vegetables. This may reduce your risk of <disease(s)> and improve your overall health.

Experts recommend eating 5 to 9 servings of fruits and vegetables a day. Try to eat a variety of different colored fruits and vegetables daily, especially darker green and yellow/orange choices. Fresh, frozen, chilled, canned, dried, and 100% fruit and vegetables juice all count. But limit or avoid fruits or vegetables that are high in added fat, sugar or salt, If you need help adding more fruits and vegetables to your diet, ask your health professional for ideas or a referral.

Risk Scenario 3.

If a subject eats more than 5 servings of fruits and vegetables per day and has moderate or high familial risk for coronary heart disease, stroke, colon cancer or breast cancer and has no personal history of coronary heart disease, stroke, colon cancer and breast cancer, then the following recommendation is provided:

Continue to eat 5 to 9 servings of fruits and vegetables a day. This may reduce your risk of <disease(s)> and improve your overall health.

Experts recommend eating 5 to 9 servings of fruits and vegetables a day. Try to eat a variety of different colored fruits and vegetables daily, especially darker green and yellow/orange choices. Fresh, frozen, chilled, canned, dried, and 100% fruit and vegetables juice all count. But limit or avoid fruits or vegetables that are high in added fat, sugar or salt, If you need help adding more fruits and vegetables to your diet, ask your health professional for ideas or a referral.

Alcohol screening questions can include the following question:

1) During the past month, did you drink one or more alcoholic beverages?

A standard drink is one 12-ounce bottle or can of beer or wine cooler, one 5-ounce glass of wine, or 1.5 ounces (one shot) of 80-proof distilled spirits.

_____ Yes
_____ No
_____ Don't know/Not sure

The following risk scenarios can occur based on familial risk for disease and the response to the above question:

Risk Scenario 1.

If a subject drinks alcoholic beverages or don't know/not sure and is a female who has weak familial risk for colon cancer and breast cancer, and any level of risk for coronary heart disease, stroke, diabetes and ovarian cancer, and user drinks alcoholic beverages, then the following recommendation is provided:

Limit your alcohol intake to no more than one drink a day.

Don't drink while you are pregnant. or if you are trying to become pregnant, because alcohol may harm the development of your fetus. Don't drink any alcohol if you have a history of alcoholism or are taking medications that may interact with alcohol. Talk to your health professional if you have questions about alcohol and how it affects your health, or if you have trouble limiting your alcohol intake.

Risk Scenario 2.

If a subject drinks alcoholic beverages and is a female who has moderate or high (e.g., strong) familial risk for colon cancer or breast cancer and no personal history of colon cancer and breast cancer, and user drinks alcoholic beverages, then the following recommendation is provided:

Limit your alcohol intake to no more than one drink a day. This may reduce your risk of getting <breast cancer and/or colon cancer>.

Don't drink while you are pregnant, or if you are trying to become pregnant, because alcohol may harm the development of your fetus. Don't drink any alcohol if you have a history of alcoholism or are taking medications that may interact with alcohol. Talk to your health professional if you have questions about alcohol and how it affects your health, or if you have trouble limiting your alcohol intake.

Risk Scenario 3.

If a subject drinks alcoholic beverages, and is a male who has moderate familial risk for colon cancer, or any level of risk for coronary heart disease, stroke, diabetes, breast cancer or ovarian cancer, and user drinks alcoholic beverages, then the following recommendation is provided:

Limit your alcohol intake to no more than one or two drinks a day.

Don't drink any alcohol if you have a history of alcoholism or are taking medications that may interact with alcohol. Talk to your health professional if you have questions about alcohol and how it affects your health, or if you have trouble limiting your alcohol intake.

Risk Scenario 4.

If a subject drinks alcoholic beverages, and is a male who has moderate or high (e.g., strong) familial risk for colon cancer and no personal history of colon cancer and breast cancer, then the following recommendation is provided:

Limit your alcohol intake to no more than one or two drinks a day. This may reduce your risk of getting colon cancer.

Don't drink any alcohol if you have a history of alcoholism or are taking medications that may interact with alcohol. Talk to your health professional if you have questions about alcohol and how it affects your health, or if you have trouble limiting your alcohol intake.

Aspirin screening questions can include the following question:

1) On average, how many days per week do you currently take aspirin?.

Do not include other pain relief medication.

_____ None
    _____ 1 day
    _____ 2 days
    _____ 3 days
    _____ 4 days
    _____ 5 days
    _____ 6 days
    _____ 7 days The following risk scenarios can occur based on familial risk for disease and the response to the above question:

Risk Scenario 1.

If a subject does not use aspirin 3 or more days a week, and has moderate or high (e.g., strong) familial risk for coronary heart disease, stroke or colon cancer, and has no personal history of coronary heart disease, stroke, diabetes and colon cancer, then the following recommendation is provided:

Talk to your health professional about the benefits and risk of aspirin.

Aspirin use may reduce your risk of <disease(s)>. However, aspirin use may have risks such as bruising more easily and bleeding from the gastrointestinal tract. If you are allergic to aspirin, you should not take it. Talk to your health professional about the possible benefits and risks of aspirin therapy. If you are taking other medications, ask your health professional if there are any harmful interactions with aspirin.

Risk Scenario 2.

If a subject uses aspirin at least 3 days a week, and has moderate or high (e.g., strong) familial risk for coronary heart disease, stroke or colon cancer and no personal history of coronary heart disease, then the following recommendation is provided:

If you have not already, talk to your health professional about the benefits and risk of aspirin therapy.

Aspirin therapy may reduce your risk of <disease(s)>. However, aspirin use may have risks such as bruising more easily and bleeding from the gastrointestinal tract. If you are allergic to aspirin, you should not take it. Talk to your health professional about the possible benefits and risks of aspirin therapy. If you are taking other medications, ask your health professional if there are any harmful interactions with aspirin.

Example 37

Exemplary Implementation of a Computer-Implemented Method for Both Determining the Familial Risk of One or More Disease of Interest and Determining a Disease Prevention Plan for a Subject FIGS. 38-58 are screen shots from an exemplary implementation of a computer-implemented method (e.g., an Internet based interactive method) for both determining the familial risk of one or more diseases of interest in a subject and determining a disease prevention plan for a subject. Such a technique can be used to collect and present information for use in any of the examples, herein. In practice, any one or more of the screen shots can be omitted, resulting in an abbreviated version of the exemplary implementation.

FIG. 37 is a screen shot 3700 of an opening page of the computer-implemented method. New users (e.g., subjects) can begin a new profile (e.g. health record), returning users can login to their password protected user profile. Additional background and informational materials are accessible via the opening page.

FIG. 38 is a screen shot 3800 of a page of the computer-implemented method for setting a user name and password in the creation of a new health record for a subject.

Figure 39:

FIG. 39 is a screen shot 3900 of a personal information page of the computer-implemented method for inputting (e.g., collecting) personal information about the subject. For example, name, date of birth, gender, adoption status, ethnicity, and the like can be collected.

FIG. 40 is a screen shot 4000 of a personal health history page of the computer-implemented method for inputting (e.g., collecting) personal health history information about the subject. For example, height, weight and disease status of common chronic diseases (e.g., coronary heart disease, stroke, diabetes, colon cancer, breast cancer, and ovarian cancer) can be collected.

Figure 41:

FIG. 41 is a screen shot 4100 of a personal health behaviors page of the computer-implemented method for inputting (e.g., collecting) personal health behavior information about the subject. For example, smoking status, physical activity regularity, dietary information, and the like can be collected.

FIG. 42 is a screen shot 4200 of a screening test page of the computer-implemented method for inputting (e.g., collecting) personal health history information about the subject. For example, information about screening exams include information about clinical breast exams, mammograms, fecal occult blood tests, sigmoidoscopies, colonoscopies, blood cholesterol tests, blood pressure tests, and blood sugar tests.

FIG. 43. is a screen shot 4300 of a page of the computer-implemented method for changing the user name and password for accessing a health record for a subject.

Figure 44:
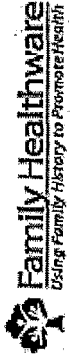

FIG. 44 is a screen shot 4400 of a family tree creation test page of the computer-implement method for inputting (e.g., collecting) family health history information for the subject's relatives. For example, the number of first and second degree relatives can be collected.

FIG. 45 is a screen shot 4500 of a family member page of the computer-implemented method for inputting (e.g., collecting) family health history information for a selected family member. For example, information about whether or not the selected family member ever had one or more disease of interest (e.g., coronary heart disease, stroke, diabetes, colon cancer, breast cancer, and/or ovarian cancer) is collected.

Figure 46:

FIG. 46 is a screen shot 4600 showing an exemplary example of information input in the family history page of FIG. 45. For example, the options related to whether or not the selected family member (e.g., My Mother, "Paula") ever had coronary heart disease is shown as part of a drop-down selection tool with the option, "Yes," and Age at first diagnosis at "20 to 24" selected.

Figure 47:

FIG. 47 is a screen shot 4700 showing an exemplary example of a completed information input page for the selected family member of FIG. 46. In, practice, "Yes," "No," or "Don't Know" can be selected for any of the diseases, with an age at first diagnosis if "Yes" is selected.

Figure 48:
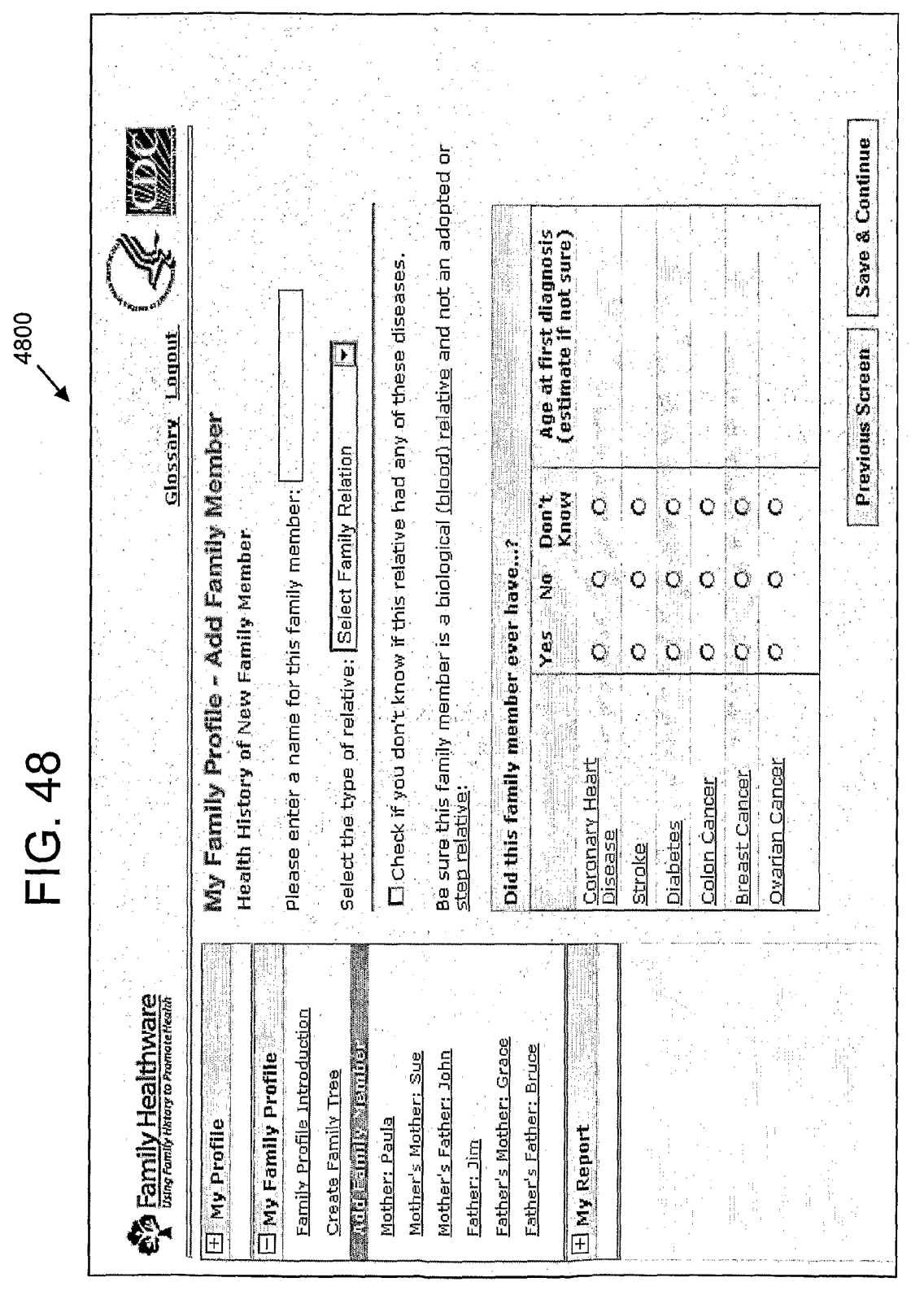

FIG. 48 is a screen shot 4800 showing an exemplary example of the computer-implemented method for inputting (e.g., collecting) family health history information for another family member by adding the family member to the family health history records.

Figure 49:

FIG. 49 is as screen shot 4900 showing an exemplary example of information input in the family health history profile of FIG. 48. For example, information about the new family member "Ed" or "my Father's Brother," (i.e. the subject's uncle) can be input.

Figure 50:

FIG. 50 is a screen shot 5000 showing an exemplary example of a confirmation pop-up warning confirming the desire to delete a relative's family health history profile from the health records.

Figure 51:
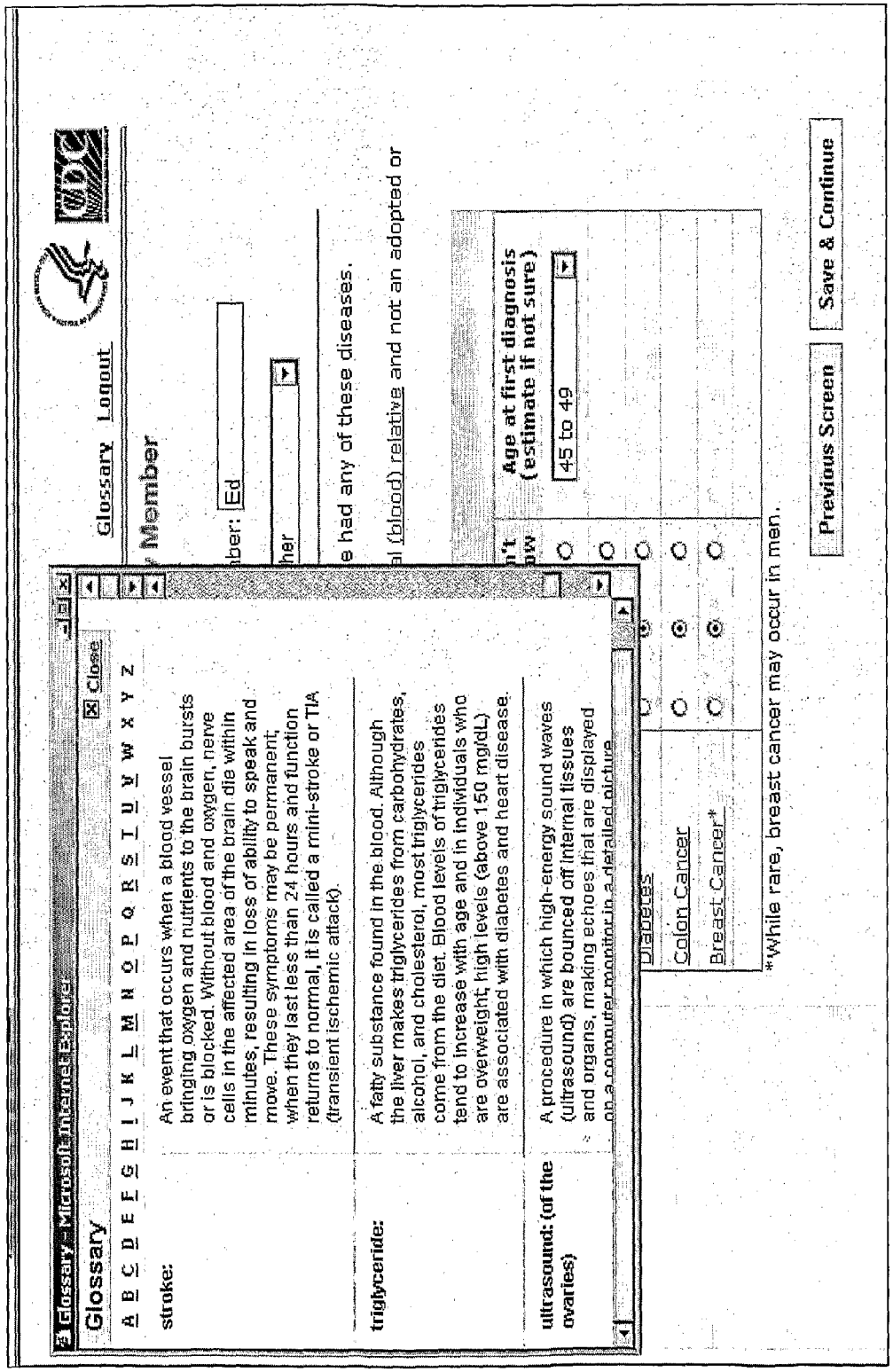

FIG. 51 is a screen shot 5100 showing an exemplary example of a glossary pop-up information guide accessible via a link of the selected disease of interest on the input page. For example, stroke was selected to access more information about stroke to help a user learn about the disease prior to inputting information about whether a relative had the selected disease or not.

Figure 52:
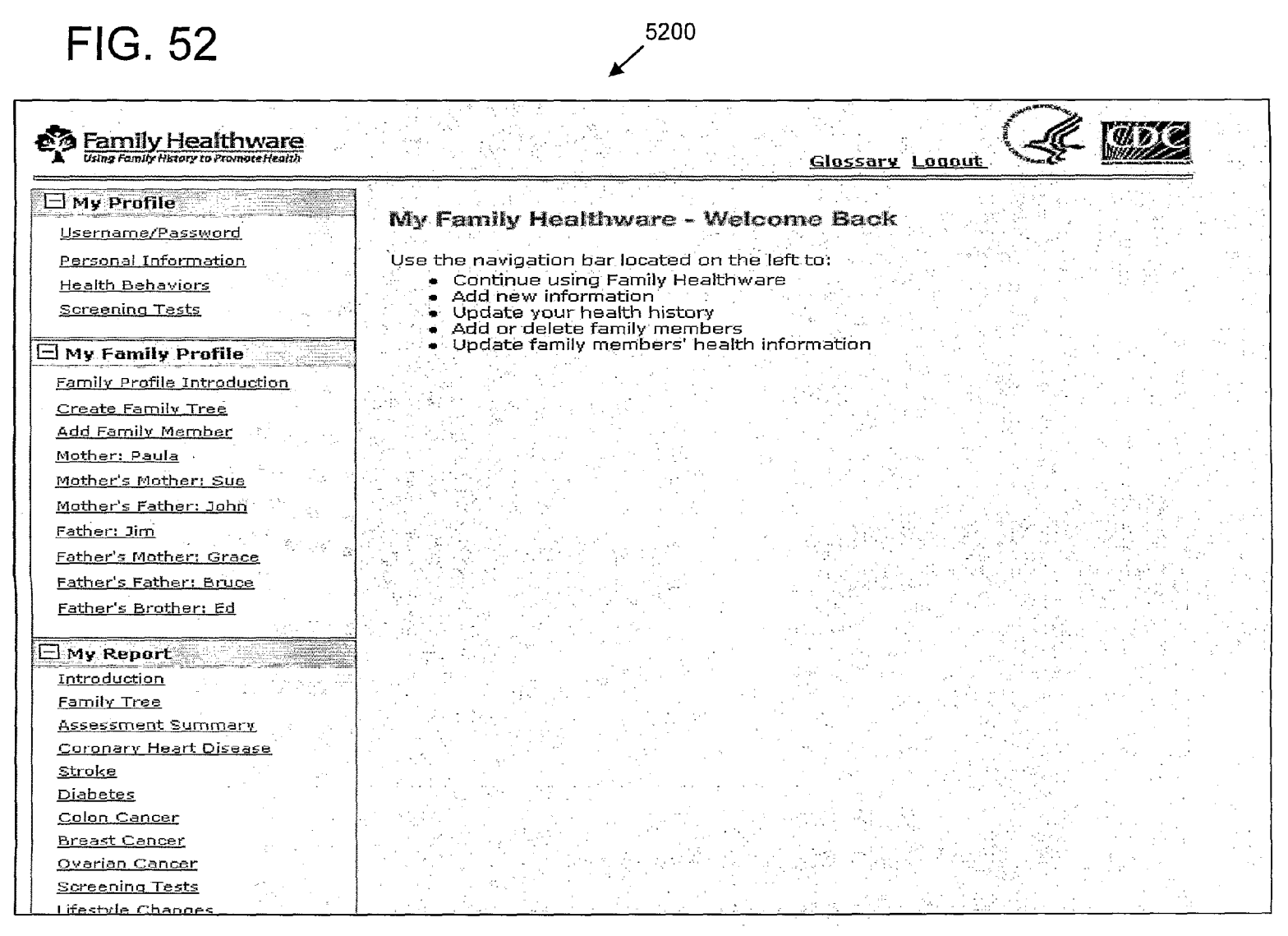

FIG. 52 is a screen shot 5200 showing an exemplary example of a welcome back page that allows the subject or user the opportunity to review, edit, update or delete information in the health records. For example, such a page can be useful for allowing the continuous updating and use of the technology.

Figure 53:

FIG. 53 is a screen shot 5300 showing an exemplary example of a report home page after the familial risk assessor has completed its assessment of risk and developed a personalized disease prevention plan.

Figure 54:
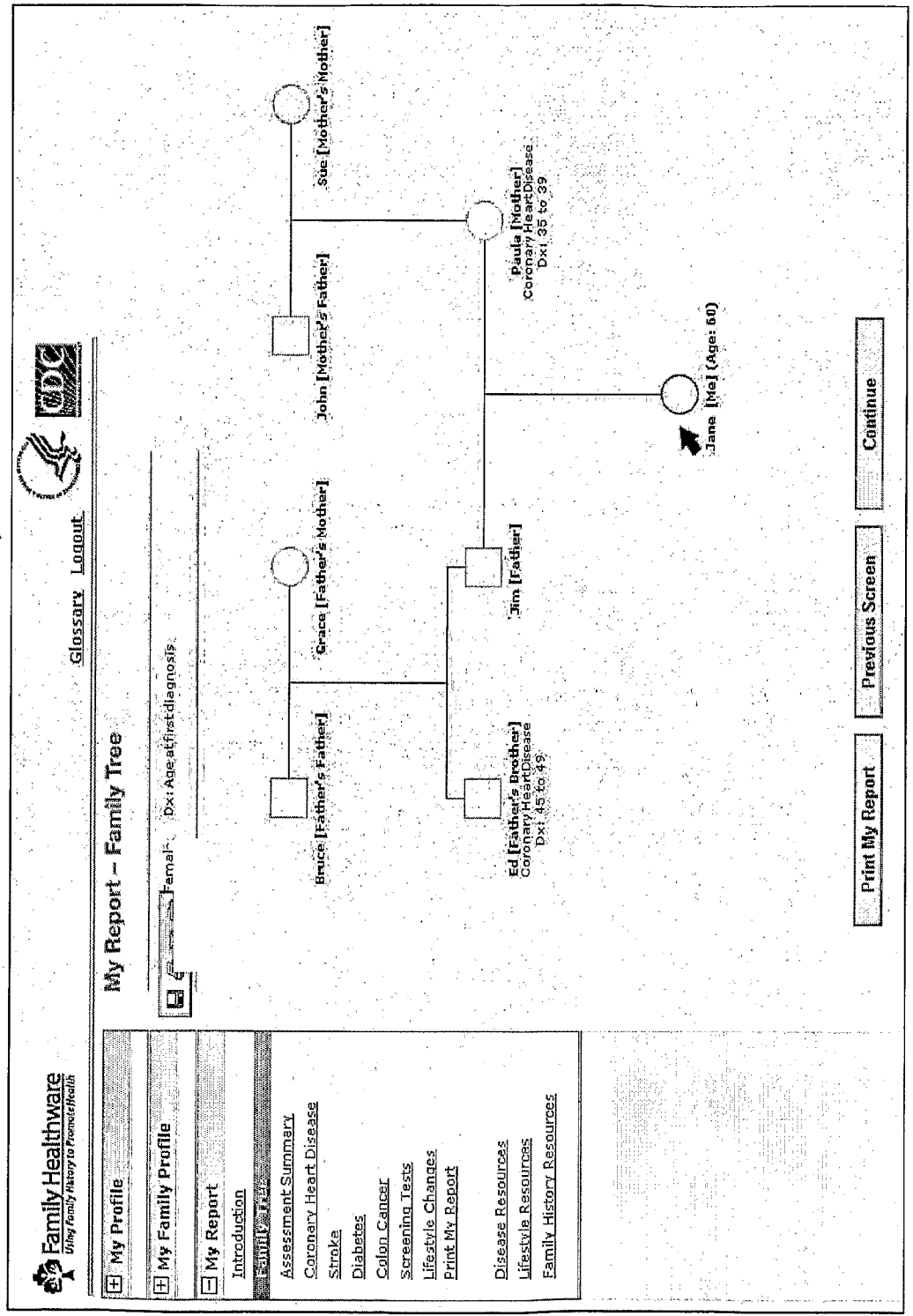

FIG. 54 is a screen shot 5400 showing an exemplary pedigree display (e.g., a family tree picture) page showing family disease history for a subject based on familial health records. In the example, an indication (e.g., legend) can be included to indicate that circles represent females and squares represent males.

FIG. 55 is a screen shot 5500 showing an exemplary familial risk assessment page for disease based on family health history. In the example, a risk assessment category (e.g., strong, medium, or weak) is displayed as a metric for the diseases.

Figure 56:
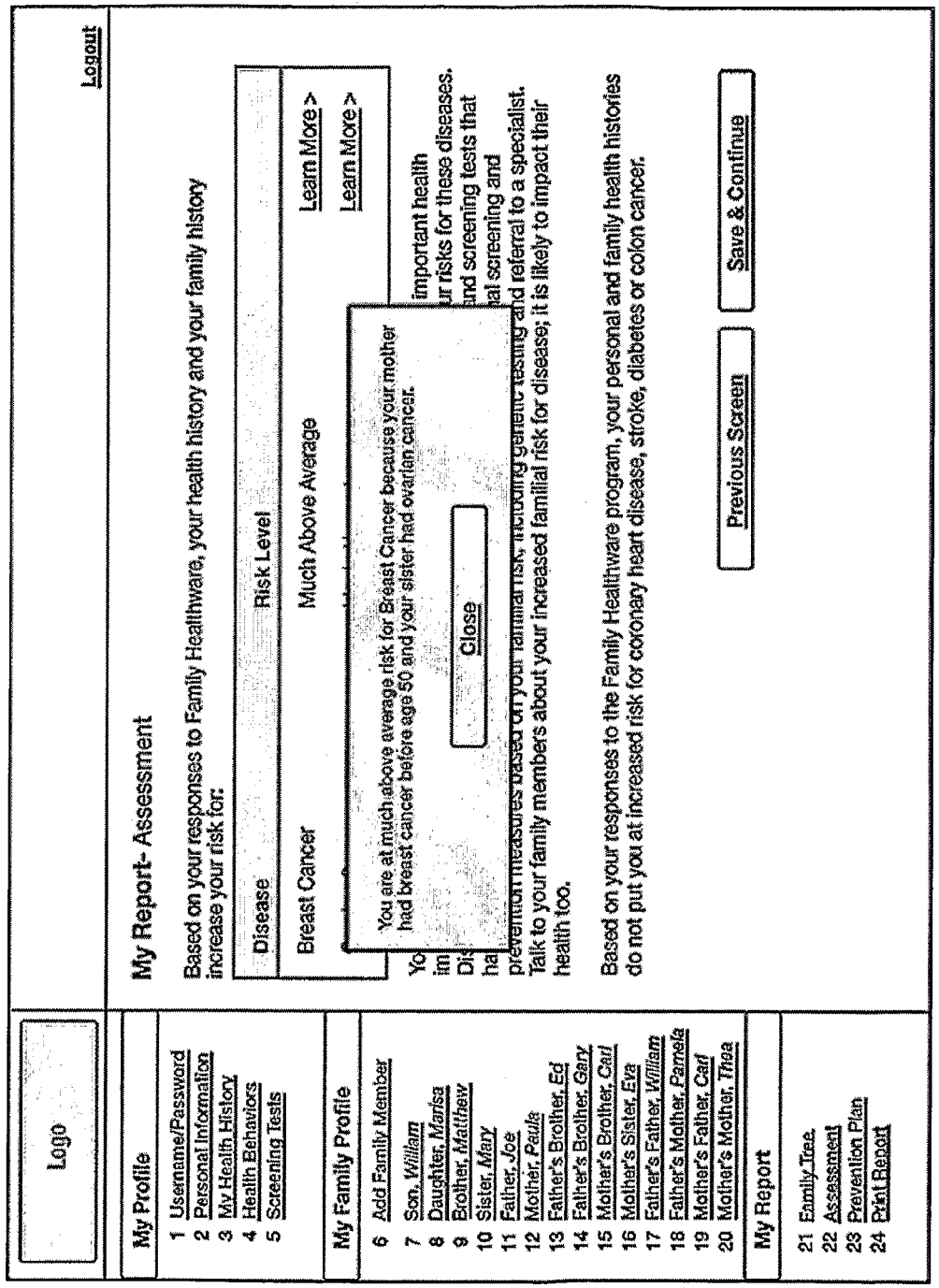

FIG. 56 is a screen shot 5600 showing the familial risk assessment page (e.g., similar to that of FIG. 55) with a pop-up familial risk clarifier further clarifying and indicating the risk assessment categories assigned.

FIG. 57 is a screen shot 5700 showing a disease prevention plan page specific to a disease of interest (e.g., coronary heart disease) based on familial health risk assessment and personal health history. In the example, recommendations are included. For example, screening tests and health behavior modifications can be recommended based on familial health risk assessment and personal health history.

Figure 58:

FIG. 58 is a screen shot 5800 showing a popup window that expounds upon a phrase (e.g., "continue cholesterol testing") when a hyperlink in the plan for the phrase is activated (e.g., clicked on).

Example 38

Another Exemplary Implementation of a Computer-Implemented Method for Both Determining the Familial Risk of One or More Disease of Interest and Determining a Disease Prevention Plan for a Subject An exemplary personalized disease prevention plan from an another exemplary implementation of a computer-implemented method (e.g., an Internet based interactive method) for both determining the familial risk of one or more diseases of interest in a subject and determining a disease prevention plan for a subject are shown below for a test case anonymously named "Two, Case.". Such a technique can be used to collect and present information for use in any of the examples, herein.

The plan can be displayed as pages in a web browser or printed out for later use. The underlined phrases shown therein can serve as hyperlinks to other places in the plan (e.g., to a location in the plan that expounds upon the underlined phrase). The underlined phrases shown therein can alternatively serve as hyperlinks to external web pages.

Name: Two, Case DOB: Jul. 6, 1935 Prepared On: Jan. 13, 2006

Thank you for using Family Healthware. Remember these important points:

Know your family history. It's one of the most important risk factors for the six diseases in this tool.

Understand that many factors influence your risk. A weak family history does not mean you won't get disease. And, a strong family history does not mean you will get disease. Other factors including your lifestyle, overall health and environment can influence your risk.

Talk to your health professional about your report. He or she is the best person to review the findings and discuss how to improve your health and reduce your risk for disease.

Discuss family history with your family. Your family history is shared by your family members. What you learned may help them.

Keep family history accurate and up to date. Try to confirm your family history, as the accuracy affects your risk rating. Update your family history every 1 to 2 years, and if you learn about changes.

<new page>

Name: Two, Case DOB: Jul. 6, 1935 Prepared On: Jan. 13, 2006

The impact of your family history on Coronary Heart Disease risk is: STRONG

Why your family history is a risk factor:
Three or more closely related family members with coronary heart disease.

The following can help reduce your overall risk:

Screening Tests
Continue testing your blood sugar.
Continue to check your blood pressure.
Continue cholesterol testing.

Lifestyle Changes
Maintain a healthy weight.
Increase your physical activity.
Increase your daily intake of fruits and vegetables.
Talk to your health professional about the benefits and risks of aspirin therapy.

Additional Risk Assessment
Your health professional may suggest additional steps to assess your risk, which might include specialized tests, a genetic evaluation, or genetic testing.

<new page>

Name: Two, Case DOB: Jul. 6, 1935 Prepared On: Jan. 13, 2006

The impact of your family history on Stroke risk is: WEAK
Although your family history risk is weak, there are other factors that can affect your risk of disease.

The following can help reduce your overall risk:

Screening Tests
Continue to check your blood pressure.
Continue cholesterol testing.

Lifestyle Changes
Increase your physical activity
Increase your daily intake of fruits and vegetables.

<new page>

Name: Two, Case DOB: Jul. 6, 1935 Prepared On: Jan. 13, 2006

The impact of your family history on Diabetes risk is: WEAK
Although your family history risk is weak, there are other factors that can affect your risk of disease.

The following can help reduce your overall risk:

Screening Tests
Based on your responses, you are following the recommendations for available screening tests for this disease. However, talk with your health professional about screening tests that may be appropriate in the future, and when and how often you should be screened.

Lifestyle Changes
Increase your physical activity.

<new page>

Name: Two, Case DOB: Jul. 6, 1935 Prepared On: Jan. 13, 2006

The impact of your family history on Colon Cancer risk is: MODERATE

Why your family history is a risk factor:
A family member with colon cancer.

The following can help reduce your overall risk:

Screening Tests
Schedule a colon cancer screening test today.

Lifestyle Changes
Maintain a healthy weight.
Increase your physical activity.
Increase your daily intake of fruits and vegetables.
Experts recommend no more than 1 drink per day for women.
Talk to your health professional about the benefits and risks of aspirin therapy.

<new page>

Name: Two, Case DOB: Jul. 6, 1935 Prepared On: Jan. 13, 2006

The impact of your family history on Breast Cancer risk is: MODERATE

Why your family history is a risk factor:
A family member with breast cancer at a later age.

The following can help reduce your overall risk:

Screening Tests
Continue breast cancer screening.

Lifestyle Changes
Maintain a healthy weight.
Increase your physical activity.
Increase your daily intake of fruits and vegetables.
Experts recommend no more than 1 drink per day for women.

Additional Risk Assessment
While your family history is a moderate risk factor for breast cancer, other factors can influence your risk. These include the age when you began menstruation, number of full-term pregnancies before age 30, or use of hormone replacement therapy. Talk to your health professional about these factors and how they might influence your risk.

<new page>

Name: Two, Case DOB: Jul. 6, 1935 Prepared On: Jan. 13, 2006

The impact of your family history on Ovarian Cancer risk is: WEAK
Although your family history risk is weak, there are other factors that can affect your risk of disease.

The following can help reduce your overall risk:

Screening Tests
No recommendations

Lifestyle Changes
No recommendations

<new page>

Name: Two, Case DOB: Jul. 6, 1935 Prepared On: Jan. 13, 2006

Screening tests that are important because of your family health history:

Cholesterol Testing
Continue cholesterol testing. Talk to your health professional about your family history, how it affects your risk of Coronary Heart Disease, and your options for screening and prevention. Your cholesterol testing should include a measure of your total cholesterol, low density lipoprotein (the "bad" cholesterol), high density lipoprotein (the "good" cholesterol), and triglyceride. If your cholesterol levels are high or abnormal, changing your lifestyle and/or taking medication can reduce your risk of coronary heart disease and stroke. Due to your increased risk, you may need to test for other cardiovascular. Ask your health professional how often you should test your cholesterol. This will depend on your cholesterol levels, other risk factors, and if you already are being treated for cholesterol problems.

Blood Glucose Testing
Continue testing your blood sugar. You may benefit from testing because of your family history. Talk to your health professional about your blood sugar and how it affects your risk of Coronary Heart Disease. Elevated blood sugar is a sign of diabetes, and it can increase your risk of coronary heart disease and stroke. If you have elevated blood sugar, you can lower it by changing your lifestyle and/or taking medication. In addition, your health professional may closely monitor and manage other cardiovascular like blood pressure and cholesterol. These steps may reduce your risk of coronary heart disease and stroke. Ask your health professional about scheduling a blood sugar test.

Blood Pressure Testing

Continue to check your blood pressure. Talk to your health professional about your family history, how it affects your risk of Coronary Heart Disease, and your options for screening and prevention. If your blood pressure is high, changing your lifestyle and/or taking medication can lower your blood pressure and reduce your risk of coronary heart disease and stroke. Ask your health professional how often you should check your blood pressure. This will depend on your blood pressure levels, other health problems, and if you already are being treated for high blood pressure.

Breast Cancer Testing

Continue breast cancer screening. Talk to your health professional about your family history, how it affects your breast cancer risk, and your options for screening and prevention. Mammograms and clinical breast exams are screening tests that can help detect breast cancer early, when it is most treatable. Due to your family history, other screening tests or prevention options may be helpful. Talk to your health professional about your risk of breast cancer, the best tests for you, and how often you should be screened.

Colon Cancer Testing

Schedule a colon cancer colon cancer today. Talk to your health professional about your family history, how it affects your colon cancer risk, and your options for screening and prevention. Colon cancer screening can help find colon cancer early, when it is most treatable. It also can detect polyp (small growths), which can be removed to prevent colon cancer. Colon cancer screening tests include: a home stool test kit, sigmoidoscopy, double-contrast barium enema, and/or colonoscopy. Usually, a home stool test is done every year, sigmoidoscopy at least every 5 years, double-contrast barium enema at least every 5 years, and colonoscopy at least every 10 years. These tests can be done alone or in combination and are usually recommended for people aged 50 and older. Talk to your health professional about your risk of colon cancer, the tests that are best for you, and how often you should be screened.
<new page>
Name: Two, Case DOB: Jul. 6, 1935 Prepared On: Jan. 13, 2006

Lifestyle changes that are important because of your family health history:

Physical Activity

Increase your physical activity. This may reduce your risk of Coronary Heart Disease, Colon Cancer and Breast Cancer and improve your overall health. The ideal level of activity is at least 30 minutes of moderate activity on five or more days a week, or at least 20 minutes of vigorous activity on three or more days a week. If you need help getting more physical activity, ask your health professional for ideas or a referral.

Weight

Your weight is appropriate for your height. Maintaining a healthy weight may reduce your risk of Coronary Heart Disease, Colon Cancer and Breast Cancer and improve your overall health. Based on your height, your ideal weight ranges from 107 to 145 pounds.

Fruits and Vegetables

Increase your daily intake of fruits and vegetables. This may reduce your risk of Coronary Heart Disease, Colon Cancer and Breast Cancer and improve your overall health. Experts recommend eating 5 to 9 servings of fruits and vegetables a day. Try to eat a variety of different colored fruits and vegetables daily, especially darker green and yellow/orange choices. Fresh, frozen, chilled, canned, dried, and 100% fruit and vegetables juice all count. But limit or avoid fruits or vegetables that are high in added fat, sugar or salt. If you need help adding more fruits and vegetables to your diet, ask your health professional for ideas or a referral.

Aspirin

Taking aspirin on a regular basis may reduce your risk of Coronary Heart Disease and Colon Cancer. Talk to your health professional about whether aspirin therapy is right for you. Aspirin use may reduce your risk of certain diseases, including coronary heart disease, stroke, and colon cancer. However, aspirin use may have risks such as bruising more easily and bleeding from the gastrointestinal tract. If you are allergic to aspirin, you should not take it. Talk to your health professional about the possible benefits and risks of aspirin therapy. If you are taking other medications, ask if there are any harmful interactions with aspirin.

Alcohol

Limit your alcohol intake to no more than one drink a day. This may reduce your risk of getting Colon Cancer and Breast Cancer. Don't drink any alcohol if you have a history of alcoholism or are taking medications that may interact with alcohol. Don't drink while you are pregnant, or if you are trying to become pregnant, because alcohol may harm the development of your fetus. Talk to your health professional if you have questions about alcohol and how it affects your health, or if you have trouble limiting your alcohol intake.

Example 39

Exemplary Disease Prevention Plan

In any of the examples herein, an electronic or paper-based report based on familial disease risk, and/or personal health information, and/or personal behavior information and/or the like can be a disease prevention plan. Such reports can include familial disease risk, familial risk clarifiers, and recommendations for screening tests, behavioral changes, and the like. Further, such reports can include pedigree analysis (e.g., family tree pictures and the like). Although particular disease prevention plans are shown in some examples, other disease prevention plans and formats can be used.

Example 40

Exemplary Advantages and Applications of Technologies

While family history is a risk factor for most chronic diseases of public health significance, it is underutilized in the practice of preventive medicine and public health for assessing disease risk and influencing early detection and prevention strategies. Geneticists have long recognized the value of family history for discovering inherited disorders, usually the result of single gene mutations. Although single gene disorders are typically associated with a large magnitude of risk, they account for only a small proportion of individuals with a genetic risk for common, chronic diseases. Most of the genetic susceptibility to these disorders is the result of multiple genes interacting with multiple environmental factors.

Family history therefore, is more than genetics; it reflects the consequences of inherited genetic susceptibilities, shared environment, shared cultures and common behaviors. All of these factors are important when estimating disease risk.

It is well known that people who have close relatives with certain diseases such as heart disease, diabetes, and cancers, are more likely to develop those diseases themselves. Studies suggest that having a first-degree relative with a chronic disease can at least double a person's risk of developing the same or a related disease. This risk generally increases with an increasing number of affected relatives, especially if their disease was diagnosed at an early age. Physicians usually collect information about a patient's family history, but often do not discuss, revisit or update it over time. Thus, they may miss opportunities to offer specific prevention recommendations for diseases that run in the family. Family medical history represents a "genomic tool" that can capture the interactions of genetic susceptibility, shared environment, and common behaviors in relation to disease risk. Determining risk of diseases for individuals based on family medical history can lead to lifestyle changes and preventive treatment, potentially saving lives and the need for intensive and expensive care treatments.

Healthcare information and resources are widely available to medical providers and patients via electronic and printed resources. Unfortunately, many informational sources provide only broad, generalized information. Preventive medicine should provide patients with feedback regarding individualized risk analysis and disease prevention information that is applicable to their own personalized health history, while also being simple and easy to use and interpret. Currently there is no standardized way to collect or interpret family health history data. Existing tools are usually paper-based, time-consuming for the patient, and difficult to interpret for the health care professional. Knowledge of increased risk for chronic diseases due to family history can influence the clinical management and prevention of a disease. Prevention strategies can include targeting lifestyle changes such as diet, exercise, and smoking cessation; screening at earlier ages, more frequently, and with more intensive methods than might be used for average risk individuals; use of chemoprevention such as aspirin; and referral to a specialist for assessment of genetic risk factors. Systems and methods for collecting information about a patient's family health history, determining risk analysis of disease based on personal and family health history, and providing a personalized disease prevention plan can influence the clinical management and prevention of disease.

Example 41

More Exemplary Advantages and Applications of Technologies

Familial risk assessment and disease plan prevention technologies can play a major role in preventive medicine by allowing primary care providers the ability to review their patients' family histories and make recommendations for early detection or intervention strategies and counseling on lifestyles. Similarly, patients have the ability to maintain and update their family history records at home and can discuss the implications with their providers during visits. The technology can be used on a standalone computer system or via networked computers via local networks and/or the Internet. Similarly, the technology can be integrated within electronic medical records or information systems allowing for increased data access and interchange. Such applications and technology also lend themselves to personalized medicine, home-based health management, as well as increasing the opportunities for evidence-based medicine to be integrated into medical practice on a daily basis.

Example 42

Exemplary Computer System for Conducting Analysis

Figure 59:
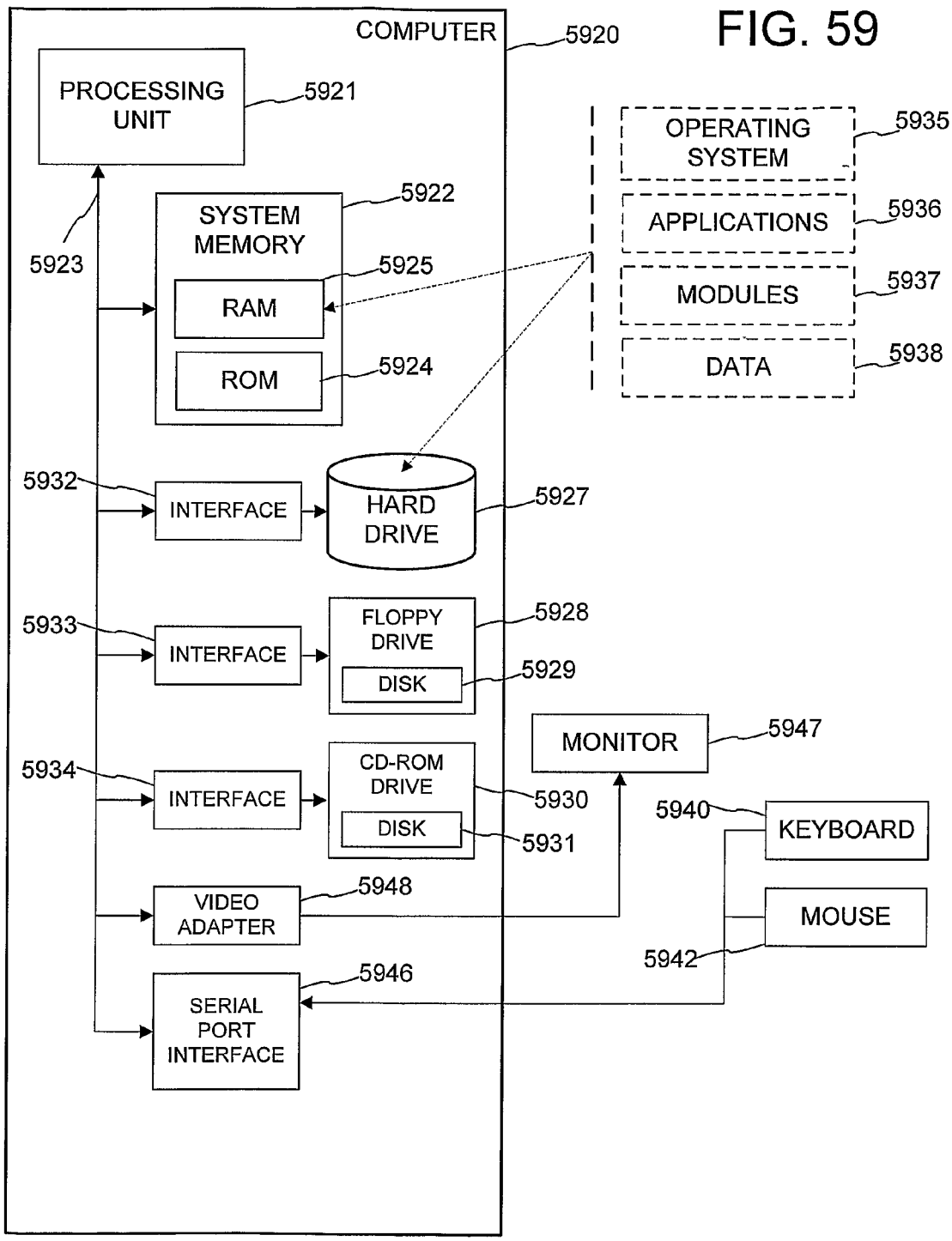
FIG. 59 is an exemplary computer system that can be implemented with the described technologies.

FIG. 59 and the following discussion provide a brief, general description of a suitable computing environment for the software (for example, computer programs) described above. The methods described above can be implemented in computer-executable instructions (for example, organized in program modules). The program modules can include the routines, programs, objects, components, and data structures that perform the tasks and implement the data types for implementing the techniques described above.

While FIG. 59 shows a typical configuration of a desktop computer, the technologies may be implemented in other computer system configurations, including multiprocessor systems, microprocessor-based or programmable consumer electronics, minicomputers, mainframe computers, and the like. The technologies may also be used in distributed computing environments where tasks are performed in parallel by processing devices to enhance performance. For example, tasks can be performed simultaneously on multiple computers, multiple processors in a single computer, or both. In a distributed computing environment, program modules may be located in both local and remote memory storage devices. For example, code can be stored on a local machine/server for access through the Internet, whereby data from assays can be uploaded and processed by the local machine/server and the results provided for printing and/or downloading.

The computer system shown in FIG. 59 is suitable for implementing the technologies described herein and includes a computer 5920, with a processing unit 5921, a system memory 5922, and a system bus 5923 that interconnects various system components, including the system memory to the processing unit 5921. The system bus may comprise any of several types of bus structures including a memory bus or memory controller, a peripheral bus, and a local bus using a bus architecture. The system memory includes read only memory (ROM) 5924 and random access memory (RAM) 5925. A nonvolatile system (for example, BIOS) can be stored in ROM 5924 and contains the basic routines for transferring information between elements within the personal computer 5920, such as during start-up. The personal computer 5920 can further include a hard disk drive 5927, a magnetic disk drive 5928, for example, to read from or write to a removable disk 5929, and an optical disk drive 5930, for example, for reading a CD-ROM disk 5931 or to read from or write to other optical media. The hard disk drive 5927, magnetic disk drive 5928, and optical disk drive 5930 are connected to the system bus 5923 by a hard disk drive interface 5932, a magnetic disk drive interface 5933, and an optical drive interface 5934, respectively. The drives and their associated computer-readable media provide nonvolatile storage of data, data structures, computer-executable instructions (including program code such as dynamic link libraries and executable files), and the like for the personal computer 5920. Although the description of computer-readable media above refers to a hard disk, a removable magnetic disk and a CD, it can also include other types of media that are readable by a computer, such as magnetic cassettes, flash memory cards, DVDs, and the like.

A number of program modules may be stored in the drives and RAM 5925, including an operating system 5935, one or more application programs 5936, other program modules 5937, and program data 5938. A user may enter commands and information into the personal computer 5920 through a keyboard 5940 and pointing device, such as a mouse 5942. Other input devices (not shown) may include a microphone, joystick, game pad, satellite dish, scanner, or the like. These and other input devices are often connected to the processing unit 5921 through a serial port interface 5946 that is coupled to the system bus, but may be connected by other interfaces, such as a parallel port, game port, or a universal serial bus (USB). A monitor 5947 or other type of display device is also connected to the system bus 5923 via an interface, such as a display controller or video adapter 5948. In addition to the monitor, personal computers typically include other peripheral output devices (not shown), such as speakers and printers.

The above computer system is provided merely as an example. The technologies can be implemented in a wide variety of other configurations. Further, a wide variety of approaches for collecting and analyzing family history data and personal health data are possible. For example, the data can be collected and analyzed, and the results presented on different computer systems as appropriate. In addition, various software aspects can be implemented in hardware, and vice versa. Further, paper-based approaches to the technologies are possible, including, for example, purely paper-based approaches that utilize instructions for interpretation of algorithms, as well as partially paper-based approaches that utilize scanning technologies and data analysis software.

Example 43

Exemplary Computer-Implemented Methods

Any of the computer-implemented methods described herein can be performed by software executed by software in an automated system (for example, a computer system). Fully-automatic (for example, without human intervention) or semi-automatic operation (for example, computer processing assisted by human intervention) can be supported. User intervention may be desired in some cases, such as to adjust parameters or consider results.

Such software can be stored on one or more computer-readable media comprising computer-executable instructions for performing the described actions.

For the sake of presentation, terms such as "determine," "generate," and "provide" are used to describe computer operations in a computing environment. These terms can be high-level abstractions for operations performed by a computer, and need not be acts performed by a human being. The actual computer operations corresponding to these terms can vary depending on implementation.

Alternatives

Having illustrated and described the principles of the invention in exemplary embodiments, it should be apparent to those skilled in the art that the described examples are illustrative embodiments and can be modified in arrangement and detail without departing from such principles. Techniques from any of the examples can be incorporated into one or more of any of the other examples (e.g., including the examples described in the claims).

In view of the many possible embodiments to which the principles of the invention may be applied, it should be understood that the illustrative embodiments are intended to teach these principles and are not intended to be a limitation on the scope of the invention. We therefore claim as our invention all that comes within the scope and spirit of the following claims and their equivalents.

We claim:

1. A computer-implemented method of providing a personalized disease prevention plan for a subject, the method comprising:
   receiving family health history information of the subject;
   receiving personal health behavior information of the subject;
   based at least on the family health history information of the subject, determining by a computer system, one or more metrics of familial risk for one or more diseases for the subject, wherein determining the one or more metrics of familial risk comprises consulting one or more familial risk matrices, wherein the consulting comprises determining whether an intersection of two familial disease history scenarios in the family health history information of the subject is present in the one or more familial risk matrices, and the intersection indicates a risk assessment category for the intersection of two familial disease history scenarios, and the one or more metrics of familial risk are determined as the risk assessment category;
   based at least on the one or more metrics of familial risk for the one or more diseases for the subject and the personal health behavior information of the subject, generating one or more personalized disease prevention recommendations for the subject; and
   presenting the one or more personalized disease prevention recommendations for the subject in the personalized disease prevention plan for the subject.

2. The method of claim 1 wherein familial risk is determined as a particular risk assessment category out of three or more risk assessment categories indicative of a risk level.

3. The method of claim 2 wherein the risk assessment category for at least one of the diseases is displayed in the personalized disease prevention plan for the subject.

4. The method of claim 1 further comprising:
   receiving personal health history information of the subject;
   wherein the one or more personalized disease prevention recommendations for the subject are based at least on the personal health history information of the subject.

5. The method of claim 1 wherein
   the personal health behavior information of the subject comprises information indicating whether the subject has had one or more screening tests performed; and
   the one or more personalized disease prevention recommendations of the subject are based at least on the information indicating whether the subject has had one or more screening tests performed.

6. The method of claim 5 wherein the information indicating whether the subject has had one or more screening tests performed indicates which of the one or more screening tests the subject has had performed.

7. The method of claim 5 wherein the one or more personalized disease prevention recommendations include a textual reference to recommended screening test practices of the subject based at least on the one or more metrics of familial risk for the one or more diseases.

8. The method of claim 5 wherein the one or more personalized disease prevention recommendations include a textual reference to present screening test practices of the subject based at least on the one or more metrics of familial risk for the one or more diseases.

9. The method of claim 5 wherein:
the personal health behavior information of the subject comprises information indicating health-related personal practices of the subject; and
the one or more personalized disease prevention recommendations of the subject are based at least on the information indicating the health-related personal practices of the subject.

10. The method of claim 9 wherein:
the health-related personal practices of the subject are one or more selected from the group consisting of:
tobacco use by the subject;
body mass index of the subject;
level of physical activity of the subject;
diet of the subject;
alcohol use by the subject; and
aspirin use by the subject.

11. The method of claim 1 wherein the personalized disease prevention plan comprises a recommendation to modify health-related personal practices of the subject based at least on the one or more metrics of familial risk for one or more diseases.

12. The method of claim 1 wherein the generating is based at least on identifying a risk scenario in information comprising the one or more metrics of familial risk for the one or more diseases for the subject and the personal health behavior information of the subject.

13. The method of claim 12 wherein the identifying identifies a risk scenario based further at least on information indicating whether the subject has had one or more screening tests performed.

14. The method of claim 1 wherein the personalized disease prevention plan comprises a recommendation to continue health-related personal practices of the subject based at least on the one or more metrics of familial risk for one or more diseases.

15. A method for determining familial risk in a subject of developing a disease of interest, the method comprising:
obtaining, from the subject, family health history information comprising:
(i) whether any first or second degree relatives have developed the disease of interest;
(ii) whether any first or second degree relatives have developed an indicator disease, other than the disease of interest, associated with an increased risk of developing the disease of interest;
obtaining for any first or second degree relative that developed the disease of interest or indicator disease information comprising:
(i) an age of onset at which the disease of interest or indicator disease developed;
(ii) a number of first degree relatives of the subject that developed the disease of interest or indicator disease;
(iii) a number of second degree relatives of the subject that developed the disease of interest or indicator disease; and
assigning, by a computer system, familial risk in the subject of developing the disease of interest based on:
(i) whether any relative that developed the disease of interest or indicator disease was a first or second degree relative;
(ii) the age of onset of the disease of interest or indicator disease in the relative;
(iii) the number of first degree relatives that developed the disease of interest or indicator disease; and
(iv) the number of second degree relatives that developed the disease of interest or indicator disease;
wherein assigning familial risk in the subject of developing the disease of interest comprises consulting one or more familial risk matrices, wherein the consulting comprises determining whether an intersection of two familial disease history scenarios in the family health history information is present in the one or more familial risk matrices, and the intersection indicates a risk assessment category for the intersection of two familial disease history scenarios, and the familial risk is determined as the risk assessment category.

16. The method of claim 15, wherein consulting one or more familial risk matrices comprises determining an intersection of two predetermined familial disease history scenarios within a familial risk matrix.

17. The method of claim 16, wherein the intersection of two predetermined familial disease history scenarios results in a categorization of familial risk as high, moderate, or low.

18. The method of claim 15, wherein the age of onset is an age range of onset.

19. The method of claim 15, wherein the disease of interest is a lineage associated disease in which lineage of the first or second degree relative is associated with different degrees of familial risk of developing the disease of interest, and assigning familial risk of developing the disease of interest comprises further assigning familial risk based on lineage of the first or second degree relative.

20. The method of claim 15, wherein the disease of interest is a gender associated disease in which gender of the first or second degree relative is associated with different degrees of familial risk of developing the disease of interest, and assigning familial risk of developing the disease of interest comprises further assigning familial risk based on gender of the first or second degree relative.

21. The method of claim 15, wherein assigning familial risk comprises categorizing risk as strong, moderate or weak.

22. The method of claim 15, wherein the disease of interest is breast cancer and the indicator disease is ovarian cancer.

23. The method of claim 20, wherein the disease of interest is breast cancer, and assigning risk based on gender of the first or second degree relative comprises assigning risk based on gender of the first or second degree relative with breast cancer.

24. The method of claim 15, wherein assigning familial risk based on the age of onset comprises assigning a higher risk responsive to determining that:
breast cancer or colon cancer age of onset was less than 50 years in men or women; or
stroke age of onset was less than 60 years in men or women; or
coronary heart disease age of onset was less than 55 years in men or less than 65 years in women; or
diabetes age of onset was 20 years or greater in men or women.

25. The method of claim 15, wherein the disease of interest is ovarian cancer and the indicator disease is breast cancer, colon cancer, or both breast and colon cancer.

26. The method of claim 15, wherein the disease of interest is colon cancer and the indicator disease is ovarian cancer.

27. The method of claim 15, wherein the disease of interest is coronary heart disease, and the indicator disease is diabetes, stroke, or both diabetes and stroke.

28. The method of claim 15, wherein the disease of interest is stroke and the indicator disease is coronary heart disease, diabetes, or both coronary heart disease and diabetes.

29. The method of claim 15, wherein the disease of interest is adult-onset diabetes.

30. The method of claim 15, further comprising determining a disease prevention plan based on the familial risk assigned and personal health history information.

31. The method of claim 15, wherein the method is an interactive computer implemented method for determining the familial risk of the subject developing the disease.

32. A computer-implemented method for determining familial risk in a subject of developing one or more diseases of interest, comprising:
   receiving family member health history information;
   in a computer system, determining familial risk in the subject of developing one or more diseases of interest based on:
   (i) whether any family member developed one or more diseases of interest or indicator diseases and was a first or second degree relative;
   (ii) an age of onset of the one or more diseases of interest or indicator diseases;
   (iii) a number of first degree relatives that developed one or more diseases of interest or indicator diseases;
   (iv) a number of second degree relatives that developed one or more diseases of interest or indicator diseases; and
   providing results indicating familial risk in the subject of developing one or more diseases of interest;
   wherein determining familial risk of developing one or more diseases comprises consulting one or more familial risk matrices, wherein the consulting comprises determining whether an intersection of two predetermined familial disease history scenarios in the family member health history information of the subject is present in the one or more familial risk matrices, and the intersection indicates a risk assessment category for the intersection of two predetermined familial disease history scenarios, and the familial risk is determined based on the risk assessment category.

33. The computer-implement method of claim 32, wherein consulting familial risk matrices comprises determining an intersection of two predetermined familial disease history scenarios within a familial risk matrix.

34. The computer-implemented method of claim 33, wherein the intersection of two predetermined familial disease history scenarios results in a categorization of familial risk as high, moderate, or low.

35. The computer-implemented method of claim 32, wherein determining familial risk of developing one or more diseases comprises categorizing risk as high, moderate, or low.

36. The computer-implemented method of claim 32, wherein:
   a given disease of interest of the one or more diseases of interest is a gender associated disease in which gender of the first of second degree relative is associated with different degrees of familial risk of developing the given disease of interest, and determining familial risk of developing the given disease of interest comprises further determining familial risk based on gender of the first or second degree relative.

37. The computer-implement method of claim 32, wherein:
   a given disease of interest of the one or more diseases of interest is breast cancer, ovarian cancer, colon cancer, stroke, coronary heart disease, or diabetes type 2 and a given indicator disease of the one or more indicator diseases is breast cancer, ovarian cancer, colon cancer, stroke, coronary heart disease, diabetes type 2, or any combination thereof.

38. The computer-implemented method of claim 37, wherein determining familial risk based on the age of the onset comprises assigning a higher risk responsive to determining that:
   breast cancer or colon cancer age of onset was less than 50 years in men or women; or
   stroke age of onset was less than 60 years in men or women; or
   coronary heart disease age of onset was less than 55 years in men or less than 65 years in women; or
   diabetes age of onset was 20 years or greater in men or women.

39. The computer-implemented method of claim 32, further comprising receiving personal health history information.

40. The computer-implemented method of claim 35, further comprising providing results indicating recommendations to lower risks of developing one or more diseases of interest.

41. The computer-implemented method of claim 40, wherein providing results indicating recommendations to lower risks of developing one or more diseases of interest comprises:
   providing standard public health prevention recommendations for low familial risk;
   providing personalized prevention recommendations for moderate familial risk; and
   providing personalized prevention recommendations and referral for genetic evaluation for high familial risk.

42. The computer-implemented method of claim 40, wherein providing results indicating recommendations to lower risks of developing one or more diseases of interest comprises:
   assessing familial risk determined for one or more diseases of interest;
   analyzing personal health history information; and
   providing personalized prevention recommendations based on the familial risk determined for one or more diseases of interest and personal health history information.

43. The computer-implemented method of claim 32, further comprising providing results indicating referral for genetic evaluation.

44. A system for determining a personalized disease prevention plan for a subject, comprising:
   a computer system comprising a processing unit and system memory;
   a health history collector for obtaining from the subject health information comprising:
   (i) a number of first or second degree relatives that have developed a disease of interest;
   (ii) a number of first or second degree relatives that have developed an indicator disease, other than the disease of interest, associated with an increased risk of developing the disease of interest;
   (iii) an age of onset at which the disease of interest or indicator disease developed for any first or second degree relative that developed the disease of interest or indicator disease;
   a familial risk assessor for assigning familial risk in the subject of developing the disease of interest based on:

(i) whether any relative that developed the disease of interest or indicator disease was a first or second degree relative;
(ii) the age of onset of the disease of interest or indicator disease in the relative;
(iii) the number of first degree relatives that developed the disease of interest or indicator disease; and
(iv) the number of second degree relatives that developed the disease of interest or indicator disease; and
a personalized disease prevention plan presenter for presenting the personalized disease prevention plan based on the familial risk in the subject;
wherein the familial risk assessor is configured to consult one or more familial risk matrices, wherein the familial risk assessor is further configured to determine whether an intersection of two familial disease history scenarios in the health information of the subject is present in the one or more familial risk matrices, and the intersection indicates a risk assessment category for the intersection of two familial disease history scenarios, and the familial risk is determined as the risk assessment category.

45. The system of claim 44, wherein health information further comprises personal health history information.

46. The system of claim 45, wherein assigning familial risk in the subject of developing the disease of interest is further based on the personal health history information of the subject.

47. The system of claim 44, wherein the personalized disease prevention plan comprises recommendations to lower risks of developing one or more diseases of interest.

48. The system of claim 44, wherein the personalized disease prevention plan comprises a pedigree display.

* * * * *

UNITED STATES PATENT AND TRADEMARK OFFICE
CERTIFICATE OF CORRECTION

| | | |
|---|---|---|
| PATENT NO. | : 8,719,045 B2 | Page 1 of 1 |
| APPLICATION NO. | : 11/815445 | |
| DATED | : May 6, 2014 | |
| INVENTOR(S) | : Yoon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1586 days.

Signed and Sealed this

Fourth Day of November, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,719,045 B2  
APPLICATION NO. : 11/815445  
DATED : May 6, 2014  
INVENTOR(S) : Yoon et al.

Page 1 of 1

It is certified that error appears in the above-identified patent and that said Letters Patent is hereby corrected as shown below:

In the Claims

Line 5 of Claim 36, Column 55, "first of second degree relative" should be --first or second degree relative--.

Line 1 of Claim 37, Column 55, "computer-implement" should be --computer-implemented--.

Signed and Sealed this  
Fourth Day of August, 2020

Andrei Iancu  
*Director of the United States Patent and Trademark Office*